US006548536B2

(12) United States Patent
Hara et al.

(10) Patent No.: US 6,548,536 B2
(45) Date of Patent: Apr. 15, 2003

(54) AGENT FOR INDUCING APOPTOSIS

(75) Inventors: Mitsunobu Hara, Sizuoka (JP); Takayuki Nakashima, Sizuoka (JP); Yutaka Kanda, Tokyo (JP); Masami Hamano, Kanagawa (JP); Shun-ichi Ikeda, Osaka (JP); Yuko Uosaki, Kanagawa (JP); Yoko Takata, Sizuoka (JP); Junji Kanazawa, Sizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/793,654

(22) Filed: Feb. 27, 2001

(65) Prior Publication Data
US 2002/0022598 A1 Feb. 21, 2002

Related U.S. Application Data

(63) Continuation-in-part of application No. PCT/JP99/04720, filed on Aug. 31, 1999.

(30) Foreign Application Priority Data

Aug. 31, 1998 (JP) ............................................ 10/246303
Feb. 26, 1999 (JP) ............................................. 11/50629

(51) Int. Cl.[7] ......................... A61K 31/34; C07G 11/00; C07D 307/77

(52) U.S. Cl. ....................... 514/461; 536/16.8; 549/297

(58) Field of Search ..................... 536/16.8; 514/461; 549/297

(56) References Cited

U.S. PATENT DOCUMENTS

| | | | | |
|---|---|---|---|---|
| 4,346,075 A | * | 8/1982 | Tomita et al. | 424/120 |
| 4,375,542 A | | 3/1983 | Waitz et al. | |
| 4,393,056 A | | 7/1983 | Tomita et al. | |
| 4,567,164 A | * | 1/1986 | Shimada et al. | |
| 5,082,933 A | | 1/1992 | Schroeder et al. | |
| 5,342,852 A | | 8/1994 | Hegde et al. | |

FOREIGN PATENT DOCUMENTS

| | | |
|---|---|---|
| EP | 0033840 | 8/1981 |
| JP | 54138501 | 10/1979 |
| JP | 55079322 | 6/1980 |
| JP | 56029595 | 3/1981 |
| JP | 56075500 | 6/1981 |
| JP | 56108719 | 8/1981 |
| JP | 56115794 | 9/1981 |
| JP | 56122392 | 9/1981 |
| JP | 56139498 | 10/1981 |
| JP | 56139500 | 10/1981 |
| JP | 57-7479 | 1/1982 |
| JP | 57-53498 | 3/1982 |
| JP | 57038796 | 3/1982 |

(List continued on next page.)

OTHER PUBLICATIONS

J.F.R. Kerr et al., "Apoptosis: A Basic Biological Phenomenon with Wide–Ranging Implications is Tissue Kinetics", Br. J. Cancer, vol. 26, pp. 239–257 (1972).

Naoto ITOH et al., "The Polypeptide Encoded by the cDNA for Human Cell Surface Antigen Fas Can Mediate Apoptosis", Cell, vol. 66, pp. 233–243 (1991).

Rie Watanabe–Fukunaga et al., "Lymphoproliferation Disorder in Mice Explained by Defects in Fas Antigen that Mediates Apoptosis", Nature, vol. 356, pp. 314–317 (1992).

(List continued on next page.)

Primary Examiner—Deborah C. Lambkin
(74) Attorney, Agent, or Firm—Greenblum & Bernstein, P.L.C.

(57) ABSTRACT

Agents for inducing apoptosis comprising a tetrocarcin derivative represented by the following formula (I) or a salt thereof as an active ingredient (---- represents a single bond or a double bond; j and k represent 0 or 1; $R^1$ to $R^3$, $R^7$ to $R^{10}$ and $R^{14}$ represent a hydrogen atom, a lower alkyl group and the like; $R^4$, $R^{11}$, $R^{12}$, $R^{13}$ and $R^{15}$ to $R^{18}$ represent a hydrogen atom, a hydroxyl group, a lower alkyl group and the like; $R^5$ and $R^6$ represents a hydrogen atom, a hydroxyl group, a lower alkyl group, a group represented by the following formula (B) ($R^{32}$ represents a formyl group and the like, $R^{33}$ to $R^{35}$ represent a hydrogen atom, a hydroxyl group, a lower alkyl group and the like); $R^{19}$ represents a hydroxyl group, a lower alkoxyl group, a lower alkanoyloxy group and the like). The agents are useful as medicaments for preventive and/or therapeutic treatment of diseases resulting from increased expression of Bcl-2 family proteins, for example, cancers, AIDS and the like.

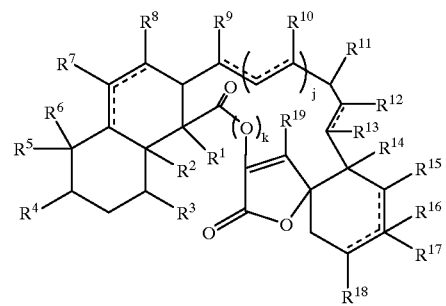

(I)

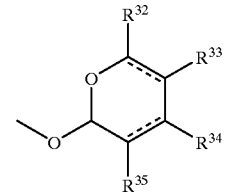

(B)

16 Claims, No Drawings

FOREIGN PATENT DOCUMENTS

| JP | 57171997 | 10/1982 |
|---|---|---|
| JP | 59161317 | 9/1984 |
| JP | 60001129 | 7/1985 |
| JP | 2174721 | 7/1990 |
| JP | 2275893 | 11/1990 |
| JP | 3-27559 | 4/1991 |
| JP | 8165286 | 6/1996 |
| JP | 9227587 | 9/1997 |
| JP | 10-57089 | 3/1998 |

OTHER PUBLICATIONS

A.H. Wyllie et al., "Cell Death: The Significance of Apoptosis", International Review of Cytology, vol. 68, pp. 251–306 (1980).

E. Duvall et al., "Death and the Cell", Immunology Today, vol. 7, No. 4, pp. 115–119 (1986).

Karen S. Sellins et al., "Gene Induction by γ–Irradiation Leads to DNA Fragmentation in Lymphocytes", The Journal of Immunology, vol. 139, No. 10, pp. 3199–3206 (1987).

T. Yamada et al., "Radiation–Induced Interphase Death of Rat Thymocytes is Internally Programmed (Apoptosis)", Int. J. Radiat. Biol., vol. 53, No. 1, pp. 65–75 (1988).

A.H. Wyllie, "Glucocorticoid–Induced Thymocyte Apoptosis is Associated with Endogenous Endonuclease Activation", Nature, vol. 284, pp. 555–556 (1980).

D. Scott Schmid et al., "DNA Fragmentation: Manifestation of Target Cell Destruction Mediated by Cytotoxic T–Cell Lines, Lymphotoxin–Secreting Helper T–Cell Clones, and Cell–Free Lymphotoxin–Containing Supernatant", Proc. Natl. Acad. Sci. USA, vol. 83, pp. 1881–1885 (1986).

John C. Hiserodt et al., "Characterization of the Cytolytic Reaction Mechanism of the Human Natural Killer (NK) Lymphocyte: Resolution into Binding, Programming, and Killer Cell–Independent Step", The Journal of Immunology, vol. 129, No. 4, pp. 1782–1787 (1982).

Donna M. Howell et al., "Nuclear Disintegration Induced by Cytotoxic T Lymphocytes: Evidence Against Damage to the Nuclear Envelope of the Target Cell", The Journal of Immunology, vol. 140, No. 3, pp. 689–692 (1988).

Gillian B. Dealtry et al., "DNA Fragmentation and Cytotoxicity Caused by Tumor Necrosis Factor is Enhanced by Interferon–γ", Eur. J. Immunol., vol. 17, pp. 689–693 (1987).

Bernhard C. Trauth et al., "Monoclonal Antibody–Mediated Tumor Regression by Induction of Apoptosis", Science, vol. 245, pp. 301–305 (1989).

Christopher A. Smith et al., "Antibodies to CD3/T–Cell Receptor Complex Induce Death by Apoptosis in Immature T cells in Thymic Culture", Nature, vol. 337, pp. 181–184 (1989).

Takushi Tadakuma et al., "CD4$^+$CD8$^+$ Thymocytes are Susceptible to DNA Fragmentation Induced by Phorbol Ester, Calcium Ionophore and Anti–CD3 Antibody", Eur. J. Immunol., vol. 20, pp. 779–784 (1990).

Masyuki Miura et al., "Induction of Apoptois in Fibroblasts by IL–1β–Converting Enzyme, a Mammalian Homolog of the C. Elegans Cell Death Gene ced–3", Cell, vol. 75, pp. 653–660 (1993).

Donald W. Nicholson et al., "Identification and Inhibition of the ICE/CED–3 Protease Necessary for Mammalian Apoptosis", Nature, vol. 376, pp. 37–43 (1995).

Masato Enari et al., "A Caspase–Activated DNase that Degrades DNA During Apoptosis, and its Inhibitor ICAD", Nature, vol. 391, pp. 43–50 (1998).

Hideki Sakahira et al., "Cleavage of CAD Inhibitor in CAD Activation and DNA Degradation During Apoptosis", Nature, vol. 391, pp. 96–99 (1998).

David M. Hockenbery, "bcl–2, A Novel Regulator of Cell Death", BioEssays, vol. 17, No. 7, pp. 631–638 (1995).

John C. Reed, "Mini–Review: Cellular Mechanisms of Disease Series: Bcl–2 and the regulation of Programmed Cell Death", The Journal of Cell Biology, vol. 124, pp. 1–6 (1994).

Hermann Steller, "Mechanisms and Genes of Cellular Suicide", Science, vol. 267, pp. 1445–1449 (1995).

M. Kasai et al., "Structure of New Antitumor Antibiotics, Tetrocarcins", 23rd Symposium of Naturally Occurring Substance, Abstract 584, pp. 584–591 (1980), accompanied by an English language abstract.

English Language Abstract of JP 2–174721, 1990.
English Language Abstract of JP 2–275893, 1990.
English Language Abstract of JP 8–165286, 1996.
English Language Abstract of JP 9–227587, 1997.
English Language Abstract of JP 10–57089, 1998.
English Language Abstract of JP 54–138501, 1979.
English Language Abstract of JP 55–079322, 1980.
English Language Abstract of JP 56–108719, 1981.
English Language Abstract of JP 56–115794, 1981.
English Language Abstract of JP 56–122392, 1981.
English Language Abstract of JP 56–139498, 1981.
English Language Abstract of JP 56–139500, 1981.
English Language Abstract of JP 56–029595, 1981.
English Language Abstract of JP 56–075500, 1981.
English Language Abstract of JP 57–171997, 1982.
English Language Abstract of JP 57–038796, 1982.
English Language Abstract of JP 60–001129, 1985.

Yoshihide Tsujimoto et al, "Involvement of the bcl–2 Gene in Human Follicular Lymphoma", Science, vol. 228, pp. 1440–1443 (1985).

Timothy J. McDonnell et al., "Expression of the Protooncogene bcl–2 in the Prostate and Its Association with Emergence of Androgen–Independent Prostate Cancer", Cancer Research, vol. 52, pp. 6940–6944 (1992).

Marc Colombel et al., "Detection of the Apoptosis–Suppressing Oncoprotein bcl–2 in Hormone–Refractory Human Prostate Cancers", American Journal of Pathology, vol. 143, No. 8, pp. 390–400 (1993).

Russell D. Leek et al., "bcl–2 in Normal Human Breast and Carcinoma, Association with Oestrogen Receptor–Positive, Epidermal Growth Factor Receptor–Negative Tumours and in situ Cancer", Br. J. Cancer, vol. 69, pp. 135–139 (1994).

Silvestrini et al., "The bcl–2 Protein: A Prognostic Indicator Strongly Related to p53 Protein in Lymph Node–Negative Breast Cancer Patients", Journal of the National Cancer Institute, vol. 86, No. 7, pp. 499–504 (1994).

Jorge J. Yunis et al., "bcl–2 and Other Genomic Alterations in the Prognosis of Large–Cell Lymphoma", New England Journal of Medicine, Nol. 320, No. 16, pp. 1047–1054 (1989).

Lydia Campos et al., "High Expression of bcl–2 Protein in Acute Myeloid Leukemia Cells is Associated with Poor Response to Chemotherapy", Blood, vol. 81, No. 11, pp. 3091–3096 (1993).

Matthew J. Pollman et al., "Inhibition of Neointimal Cell bcl–x Expression Induces Apoptosis and Regression of Vascular Disease", *Nature Medicine*, vol. 4, No. 2., pp. 222–227 (1998).

U. Muller–Ladner et al., *Arthritis and Rheumatism*, vol. 37 (Supplemental), pp. S163 (1994).

Gary S. Firestein et al., "Apoptosis in Rheumatoid Arthritis Synovium", *J. Clin. Invest.*, vol. 96, pp. 1631–1638 (1995).

Cunningham et al., "BCL–2 Antisense Therapy in Patients with Non–Hodgkin Lymphoma", *The Lancet*, vol. 349, pp. 1137–1141 (1997).

Ziegler et al., Induction of Apoptosis in Small–Cell Lung Cancer Cells by an Antisense Oligodeoxynucleotide Targeting the Bcl–2 Coding Sequence, *Journal of the National Cancer Institute*, vol. 89, No. 14, pp. 1027–1036 (1997).

Burkhard Jansen et al., "bcl–2 Antisense Therapy Chemosensitizes Human Melanoma in SCID Mice", *Nature Medicine*, vol. 4, No. 2, pp. 232–234 (1998);.

Makoto Matsumoto et al., "Isolation, Characterization and Structures of PA–46101 A and B", *The Journal of Antibiotics*, vol. 43, No. 7, pp. 739–737 (1990).

Rosanne Bonjouklian et al., "Structures of A88696 C, D and F: Gastric ATP–ase Inhibitors", *Tetrahedron Letters*, vol. 34, No. 49, pp. 7857–7860 (1993).

\* cited by examiner

AGENT FOR INDUCING APOPTOSIS

This application is a Continuation-In-Part of International Application No. PCT/JP99/04720, filed Aug. 31, 1999, which was not published in English, and which claims priority of Japanese Application Nos. 10/246303, filed Aug. 31, 1998, and 11/50629, filed Feb. 26, 1999. The entire disclosures of International Application No. PCT/JP99/04720, and Japanese Application Nos. 10/246303 and 11/50629 are incorporated by reference herein in their entireties.

TECHNICAL FIELD

The present invention relates to an agent for inducing apoptosis which comprises a tetrocarcin derivative as an active ingredient and which is useful for preventive and/or therapeutic treatment of cancers, AIDS or the like.

BACKGROUND ART

Cell death is considered to be caused by two types of mechanisms, and one of them is the cell death called necrosis. This process is morphologically characterized by marked expansion of mitochondria, swelling of cytoplasm, degeneration of nuclei and subsequent decay and autolysis of cells, and the process occurs passively and accidentally. Necrocytosis is generally observed when cells receive physical injury, chemical toxicoids or the like.

The other type is the cell death called apoptosis or programmed cell death (Kerr, J. F. and Wyllie, A. H., Br. J. Cancer, 26, pp.239–257, 1972). This cell death is considered to occur under various physiological conditions. The morphological characteristics thereof include absence of contact with neighboring cells, concentration of cytoplasm, pyknosis of chromatin participating in endonuclease activity and pyknosis of nuclei, segmentation of nuclei and so forth, and disappearance of microvilli of cell surfaces, smoothing of cell surfaces (membrane blebbing on cell surfaces) and the like are also observed. Further, a phenomenon is also observed in which nucleosome units of DNA are fragmented into DNAs of 180 to 200 base length by the endonuclease activity. The mechanism of apoptosis is explained as a mechanism of phagocytosis for final fragments of apoptic cells by neighboring cells.

Apoptosis is essential in many physiological processes including germ development and clonal selection in an immune system (Ito, N. et al., Cell, 66, pp.233–243, 1991), and the process is initiated by various stimulations such as removal of glucocorticoid hormones or certain types of growth factors in immature thymocytes (Watanabe-Fukunaga, R. et al., Nature, 356, pp.314–317, 1992). The apoptosis is also reported to be induced by cell damage by cytotoxic T cells, hormone-dependent tissue atrophy, irradiation with radiation, NK cells, killer cells, cytokines such as a tumor necrosis factor (TNF) and so forth (Wyllie, A. H. et al., Int. Rev. Cytol., 68, pp.251–306, 1980; Duvall, E. and Wyllie, A. H., Immunology Today, 7, pp.115–119, 1986; Sellins, K. S. et al., J. Immunol., 139, pp.3199–3206, 1987; Yamada, T. et al., Int. J. Radiat. Biol., 53, pp.65–75, 1988; Wyllie, A. H., Nature, 284, pp.555–556, 1980; Schmid, D. S. et al., Proc. Natl. Acad. Sci. USA, 83, pp.1881–1885, 1986; Hiserodt, J. C. et al., J. Immunol., 129, pp.1782–1787, 1982; Howell, D. M. et al., J. Immunol., 140, pp.689–692, 1988; Gillian, B. et al., Eur. J. Immunol. 17, pp.689–693, 1987).

In addition, certain kinds of antibodies such as anti-CD3 antibodies, anti-Apo-1 antibodies and anti-Fas antibodies also induce apoptosis (Trauth, B. C. et al., Science, 245, pp.301–305, 1989; Smith, C. A. et al., Nature, 337, pp.181–184, 1989; Tadakuma, T. et al., Eur. J. Immunol., 20, pp.779–784, 1990), and apoptosis has also been verified in findings of spontaneous regression of malignancies (Yasuo Nakamura et al., Rinsho Hifuka, 35, pp.289–295, 1981).

A series of cysteine proteases called caspase is known to be activated in the process of apoptosis, which is preserved over the species as a biochemical mechanism involved in the induction of apoptosis (Miura, M. et al., Cell, 75, pp.653–660, 1993; Nicholson, D. W. et al., Nature, 376, pp.37–43, 1995). It has been elucidated that degradation of plural protein substrates by the aforementioned caspase triggers the induction of apoptosis, and an increase of the enzymatic activity of caspase is a biochemical sign indicating induction of apoptosis (Enari, M. et al., Nature, 391, pp.43–50, 1998; Sakahira, H. et al., Nature, 391, pp.96–99, 1998).

It is known that the process of the aforementioned caspase activation is suppressed by proteins belonging to the Bcl-2 family, e.g., Bcl-2 and Bcl-$X_L$, and when the expression levels of the proteins of the Bcl-2 family increase, the activation of caspase due to various apoptosis inductive stimulations is suppressed, thereby apoptosis fails to be induced (Hockenbery, D. M., BioEssays, 17, pp.631–638, 1995; Reed, J. C., J. Cell. Biol., 124, pp.1–6, 1994; Steller, H., Science, 267, pp.1445–1449, 1995).

As diseases caused by resistance to apoptosis due to the increase of expression levels of the Bcl-2 family proteins, examples include human follicular B-type lymphoma (Tsujimoto, Y. et al., Science, 228, pp.1440–1443, 1985), non-hormone dependent prostatic cancer (McDonnell, T. et al., Cancer Res., 52, pp.6940–6944, 1992; Colombel, M. et al., Am. J. Pathlogy, 143, pp.390–400, 1993), hormonotherapy resistant breast cancer (Leek, R. D. et al., Br. J. Cancer, 69, pp.135–139, 1994; Silverstrini, R. et al., J. National Cancer Inst., 86, pp.499–504, 1994), anticancer agent-resistant tumor (Ynis, J. J. et al., N. Engl. J. Med., 320, pp.1047–1054, 1989; Campos, L. et al., Blood, 81, pp.3091–3096, 1993), arteriosclerosis (Pollman, M. J. et al., Nature Med., 4, pp.222–227, 1998), Rheumatoid arthritis (Mueller- Ladner, U. et al., Arthritis and Rheumatism, 37 (suppl.) S163, 1994; Firestein, G. S. et al., J. Clin. Invest., 96, pp.1631–1638, 1995) and so forth.

Therapies by administration of antisense RNA for bcl-2 or bcl-$X_L$ have been reported as remedies for diseases resulting from the increase of expression levels of Bcl-2. However, no effective pharmacotherapy using a low molecular organic compound has been known so far (Webb, A. et al. Lancet, 349, pp.1137–1141, 1997; Ziegler, A. et al., J. National Cancer Inst., 89, pp.1027–1036, 1997; Jansen, B. et al., Nature Med., 4, pp.232–234, 1998; Pollman, M. J. et al., Nature Med., 4, pp.222–227, 1998).

Tetrocarcins are a class of antibiotics and are known to have an antibacterial and anti-cancer activity. Among them, tetrocarcin A has the following structure.

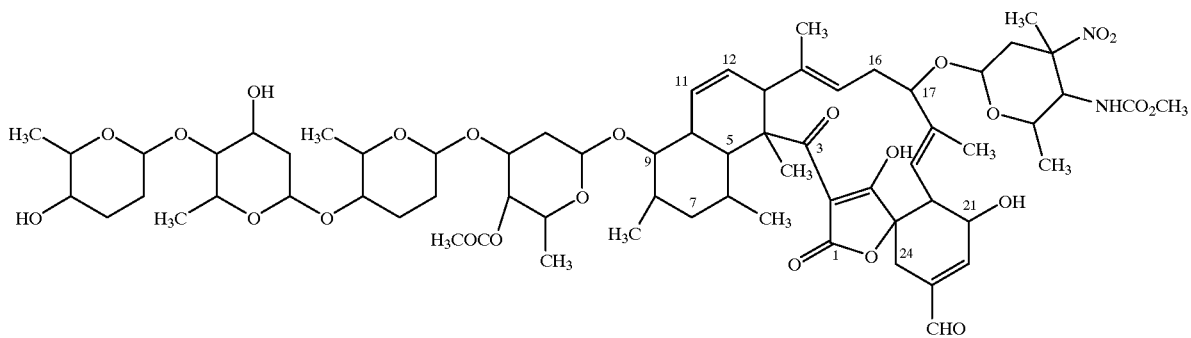

In addition to the above tetrocarcin A, tetrocarcins B, C, D, E1, E2, F, F-1, F-2, G, H, I, J, K, L, M and so forth having structures similar thereto are known. The aforementioned compounds wherein the 9- and 21-positions are substituted with lower alkanoyloxy groups or wherein the 9-, 17- and 21-positions are substituted with lower alkanoyloxy groups are also included in the tetrocarcins. These tetrocarcins are described in the following patent documents (they are occasionally referred to using DC-11 as DC-11-A, DC-11-B and so forth without using the name of tetrocarcin): Japanese Patent Unexamined Publication (Kokai) Nos. 54-138501/1979, 55-79322/1980, 56-139500/1981, U.S. Pat. No. 4,346,075 (all for tetrocarcin A), Japanese Patent Unexamined Publication Nos. 56-115794/1981, 56-122392/1981 (both for tetrocarcin B), Japanese Patent Unexamined Publication Nos. 56-75500/1981, 56-122392/1981 (both for tetrocarcin C), Japanese Patent Unexamined Publication No. 56-122392/1981 (tetrocarcin D), Japanese Patent Unexamined Publication No. 57-38796/1982 (tetrocarcins E1 and E2), Japanese Patent Unexamined Publication No. 57-53498/1982 (tetrocarcins F, G and H), Japanese Patent Unexamined Publication No. 57-171997/1982 (tetrocarcins I, J, K, L and M), Japanese Patent Unexamined Publication No. 57-7479/1982 (tetrocarcins F-1 and F-2), and Japanese Patent Unexamined Publication 57-7479/1982 (compounds having lower alkanoyloxy groups at the 9- and 21-positions, and compounds having lower alkanoyloxy groups at the 9-, 17- and 21-positions).

The tetrocarcins are also known to have anti-Piroplasma activity (Japanese Patent Unexamined Publication Nos. 59-161317/1984 and 60-1129/1985). Furthermore, there are known several compounds as analogues of tetrocarcins [the family of BE-45722 (Japanese Patent Unexamined Publication No. 9-227587/1997, antibacterial activity), tetromycins (tetromycins A and B (Japanese Patent Unexamined Publication No. 8-165286/1996), tetromycins C1 to C5 (Japanese Patent Unexamined Publication No. 10-057089/1998), antibacterial activity), kijanimicins (Japanese Patent Publication (Kokoku) No. 3-27559/1991, EP33840A2, U.S. Pat. No. 4,375,542, antibacterial, anti-cancer, anti-parasitic and anti-inflammatory activities), BMY-42448 (U.S. Pat. No. 5,082,933, anti-tumor activity), macrocyclic lactone produced by a microorganism, *S. aerocolongenes* sub sp. antibiotics SCC 1886, ATCC55003 (U.S. Pat. No. 5,342,852, antibacterial activity), chlorothricins (Japanese Patent Unexamined Publication Nos. 2-174721/1990 and 2-275893/1990, hypolipidemic action), anthramycins (Japanese Patent Unexamined Publication Nos. 56-29595/1981, 56-108719/1981 and 56-139498/1981, antibacterial and anti-cancer activity), A88696C, D and F (Tetrahedron Lett., 34, pp.7857–7860, 1993, gastric ATP-ase inhibitory action), and PA-46101A and B (J. Antibiot., 43, pp.739–747, 1990, antibiotics)]. However, apoptosis induction activity of said compounds has not been known.

DISCLOSURE OF THE INVENTION

An object of the present invention is to provide an agent for inducing apoptosis. More specifically, the object of the present invention is to provide an agent for inducing apoptosis that can exert desired pharmacological effects on various diseases by apoptosis inducing action resulting from Bcl-2 inhibition. Another object of the present invention is to provide a medicament which comprises a substance having the aforementioned action as an active ingredient. More specifically, the object of the present invention is to provide a medicament useful for preventive and/or therapeutic treatment of cancers, AIDS, ARC (AIDS related conditions), osteoarthritis, autoimmune diseases such as rheumatoid arthritis and systemic lupus erythematodes, collagenosis such as Sjögren's syndrome, arteriosclerosis or the like. A still further object of the present invention is to provide novel tetrocarcin derivatives useful as active ingredients of various medicaments such as anticancer agents and antibacterial agents.

The inventors of the present invention conducted various studies to achieve the aforementioned objects. As a result, they found that the compounds represented by the following general formula had action of inducing apoptosis and they were useful for preventive and/or therapeutic treatment of diseases including cancer and AIDS. The present invention was achieved on the basis of the aforementioned findings.

The present invention thus provides an agent for inducing apoptosis which comprises, as an active ingredient, a tetrocarcin derivative represented by the following general formula (I) or a physiologically acceptable salt thereof:

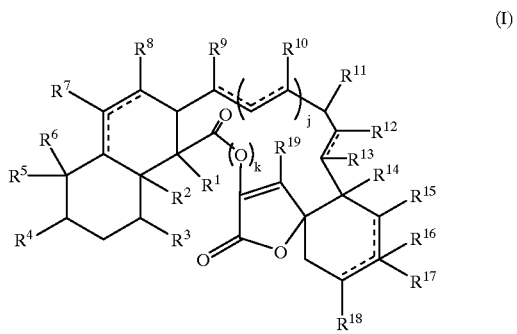

(I)

wherein ---- represents a single bond or a double bond provided that two adjacent bonds are not simultaneously double bonds;

j and k represent 0 or 1;

$R^1$, $R^2$, $R^3$, $R^7$, $R^8$, $R^9$, $R^{10}$, and $R^{14}$ independently represent a hydrogen atom, a substituted or unsubstituted lower alkyl group, a formyl group or a carboxyl group; $R^4$, $R^{12}$, $R^{13}$, and $R^{15}$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m and p independently represent an integer of from 0 to 8, and $R^{20}$, $R^{21}$, and $R^{22}$ independently represent a lower alkyl group or a substituted or unsubstituted aryl group);

$R^{16}$, $R^{17}$, and $R^{18}$ independently represent a hydrogen atom, a hydroxyl group, a substituted or unsubstituted lower alkyl group, a substituted or unsubstituted lower alkanoyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), a substituted or unsubstituted lower alkoxyalkyl group, a formyl group, a carboxyl group, a substituted or unsubstituted lower alkoxycarbonyl group, a substituted or unsubstituted lower alkanoyloxyalkyl group, a group represented by —(CH$_2$)$_r$OSi(R$^{23}$)(R$^{24}$)(R$^{25}$) (in the formula, r represents an integer of from 1 to 8, $R^{23}$, $R^{24}$, and $R^{25}$ independently represent a lower alkyl group or a substituted or unsubstituted aryl group), a group represented by —CH=CHR$^{26}$ (in the formula, $R^{26}$ represents a substituted or unsubstituted lower alkoxycarbonyl group), a group represented by —CH=NOR$^{27}$ (in the formula, $R^{27}$ represents a hydrogen atom or a substituted or unsubstituted lower alkyl group), or —CH(X$^1$R$^{28}$)$_2$ (in the formula, X$^1$ represents an oxygen atom or a sulfur atom, and $R^{28}$ represents a lower alkyl group or two of $R^{28}$ are combined together to represent —(CH$_2$)$_2$— or —(CH$_2$)$_3$—), or $R^{16}$ and $R^{17}$ are combined together to represent an oxygen atom;

$R^{11}$ represents a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), or a group represented by the following formula (A):

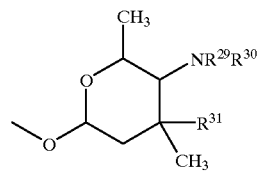

(A)

(in the formula, $R^{29}$ represents a hydrogen atom or a lower alkyl group, $R^{30}$ represents a hydrogen atom, a substituted or unsubstituted lower alkyl group, a substituted or unsubstituted lower alkanoyl group, or a substituted or unsubstituted lower alkoxycarbonyl group, and $R^{31}$ represents a nitro group, a nitroso group, a hydroxyl group, or an amino group);

$R^{19}$ represents a hydroxyl group, a substituted or unsubstituted lower alkoxyl group, or a substituted or unsubstituted lower alkanoyloxy group;

$R^5$ and $R^6$ are combined together to represent an oxygen atom or $R^5$ and $R^6$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted aroyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), or when $R^5$ represents a hydrogen atom, $R^6$ may be a group selected from the group consisting of the groups represented by the following formulas (B), (B-2), (C-1), (C-2), (D), and (E):

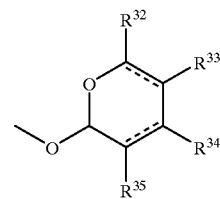

(B)

(in the formula, ---- represents a single bond or a double bond, $R^{32}$ represents a hydrogen atom, a formyl group, or a group represented by —CH$_2$R$^{32a}$, and $R^{33}$, $R^{34}$, $R^{35}$, and $R^{32a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20a}$)(R$^{21a}$)(R$^{22a}$) (in the formula, $R^{20a}$, $R^{21a}$, and $R^{22a}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

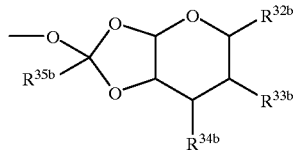
(B-2)

(in the formula, $R^{35b}$ represents a substituted or unsubstituted lower alkyl group, $R^{32b}$ represents a hydrogen atom, a formyl group, or a group represented by —$CH_2R^{32c}$, and $R^{33b}$, $R^{34b}$, and $R^{32c}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —$OSi(R^{20a1})(R^{21a1})(R^{22a1})$ (in the formula, $R^{20a1}$, $R^{21a1}$, and $R^{22a1}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

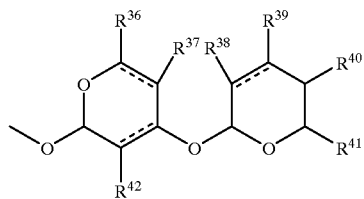
(C-1)

(in the formula, ---- represents a single bond or a double bond, $R^{36}$ represents a hydrogen atom, a formyl group, or a group represented by —$CH_2R^{36a}$, $R^{41}$ represents a hydrogen atom or a group represented by —$CH_2R^{41a}$, and $R^{37}$, $R^{38}$, $R^{39}$, $R^{40}$, $R^{41a}$, $R^{42}$, and $R^{36a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —$OSi(R^{20b})(R^{21b})(R^{22b})$ (in the formula, $R^{20b}$, $R^{21b}$, and $R^{22b}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

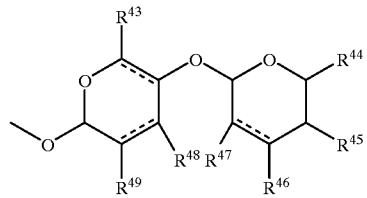
(C-2)

(in the formula, ---- represents a single bond or a double bond, $R^{43}$ represents a hydrogen atom, a formyl group or a group represented by —$CH_2R^{43a}$, $R^{44}$ represents a hydrogen atom or a group represented by —$CH_2R^{44a}$, and $R^{44a}$, $R^{45}$, $R^{46}$, $R^{47}$, $R^{48}$, $R^{49}$, and $R^{43a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —$OSi(R^{20c})(R^{21c})(R^{22c})$ (in the formula, $R^{20c}$, $R^{21c}$, and $R^{22c}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

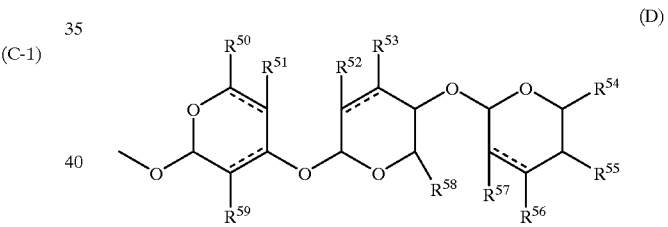
(D)

(in the formula, ---- represents a single bond or a double bond, $R^{50}$ represents a hydrogen atom, a formyl group or a group represented by —$CH_2R^{50a}$, $R^{58}$ represents a hydrogen atom or a group represented by —$CH_2R^{58a}$, $R^{54}$ represents a hydrogen atom or a group represented by —$CH_2R^{54a}$, and $R^{51}$, $R^{52}$, $R^{53}$, $R^{54a}$, $R^{55}$, $R^{56}$, $R^{57}$, $R^{58a}$, $R^{59}$, and $R^{50a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —$OSi(R^{20d})(R^{21d})(R^{22d})$ (in the formula, $R^{20d}$, $R^{21d}$, and $R^{22d}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)); and

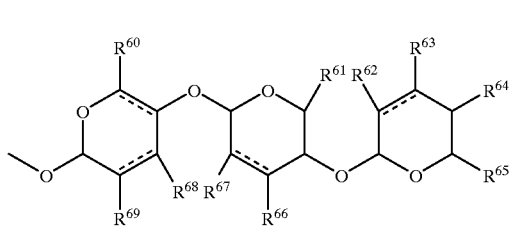

(E)

(in the formula, ---- represents a single bond or a double bond, $R^{60}$ represents a hydrogen atom, a formyl group or a group represented by —$CH_2R^{60a}$, $R^{61}$ represents a hydrogen atom or a group represented by —$CH_2R^{61a}$, $R^{65}$ represents a hydrogen atom or a group represented by —$CH_2R^{65a}$, and $R^{61a}$, $R^{62}$, $R^{63}$, $R^{64}$, $R^{65a}$, $R^{66}$, $R^{67}$, $R^{68}$, $R^{69}$, and $R^{60a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —$OSi(R^{20e})(R^{21e})(R^{22e})$ (in the formula, $R^{20e}$, $R^{21e}$, and $R^{22e}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)).

According to another aspect of the present invention, provided is a medicament which comprises the tetrocarcin derivative represented by the aforementioned formula (I) or a physiologically acceptable salt thereof as an active ingredient and which is used for preventive and/or therapeutic treatment of a disease which can be preventively and/or therapeutically treated by induction of apoptosis. Examples of the diseases include diseases resulting from increased expression of the Bcl-2 family proteins, for example, cancers, AIDS, ARC (AIDS related conditions), osteoarthritis, autoimmune diseases such as rheumatoid arthritis and systemic lupus erythematodes, collagenosis such as Sjögren's syndrome, arteriosclerosis and so forth.

The aforementioned inducer and medicament are preferably provided in the form of a pharmaceutical composition comprising the tetrocarcin derivative represented by the aforementioned formula (I) or a physiologically acceptable salt thereof together with an additive for a pharmaceutical preparation. According to the present invention, further provided are use of the tetrocarcin derivative represented by formula (I) or a physiologically acceptable salt thereof for the manufacture of the aforementioned agent for inducing apoptosis or the aforementioned medicament; and a method for preventive and/or therapeutic treatment of a disease resulting from increased expression of the Bcl-2 family proteins, which comprises the step of administering a preventively and/or therapeutically effective amount of the tetrocarcin derivative represented by formula (I) or a physiologically acceptable salt thereof to a mammal including human.

According to a further aspect of the present invention, provided is a tetrocarcin derivative represented by the following formula (Ia) or a salt thereof:

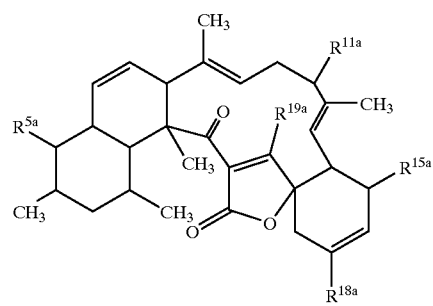

(Ia)

wherein $R^{15a}$ represents a hydroxyl group, —$OSi(R^{70})(R^{71})(R^{72})$ (in the formula, $R^{70}$, $R^{71}$, and $R^{72}$ independently represent a lower alkyl group or a substituted or unsubstituted aryl group), a substituted or unsubstituted lower alkoxyl group, a substituted or unsubstituted aralkyloxy group, a substituted or unsubstituted aryloxy group, a substituted or unsubstituted lower alkanoyloxy group, a substituted or unsubstituted lower alkenoyloxy group or a substituted or unsubstituted aroyloxy group; $R^{11a}$ represents any one of the substituents defined for the aforementioned $R^{15a}$, or a group represented by the following formula (F):

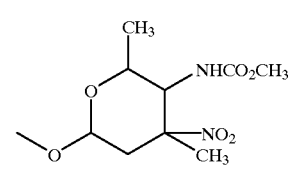

(F)

$R^{5a}$ represents any one of the substituents defined for the aforementioned $R^{15a}$, or a group selected from the group consisting of a group represented by the following formula (G):

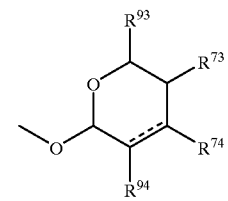

(G)

(in the formula, ---- represents a single bond or a double bond, $R^{93}$ represents a hydrogen atom or a group represented by —$CH_2R^{93a}$, and $R^{73}$, $R^{74}$, $R^{94}$, and $R^{93a}$ independently represent a hydrogen atom or any one of the substituents defined for the aforementioned $R^{15a}$), a group represented by the following formula (G-2):

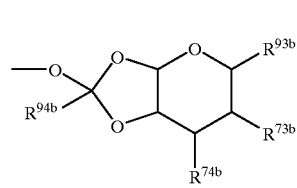

(G-2)

(in the formula, $R^{94b}$ represents a substituted or unsubstituted lower alkyl group, $R^{93b}$ represents a hydrogen atom or a group represented by —CH$_2$R$^{93c}$, and R$^{73b}$, R$^{74b}$ and R$^{93c}$ independently represent a hydrogen atom or any one of the substituents defined for the aforementioned R$^{15a}$), a group represented by the following formula (H):

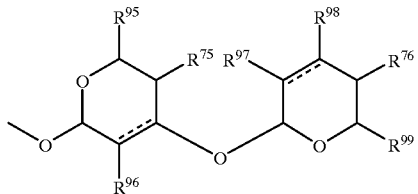

(H)

(in the formula, ---- represents a single bond or a double bond, R$^{95}$ represents a hydrogen atom or a group represented by —CH$_2$R$^{95a}$, R$^{99}$ represents a hydrogen atom or a group represented by —CH$_2$R$^{99a}$, and R$^{95a}$, R$^{75}$, R$^{96}$, R$^{97}$, R$^{98}$, R$^{76}$ and R$^{99a}$ independently represent a hydrogen atom or any one of the substituents defined for the aforementioned R$^{15a}$), a group represented by the following formula (J):

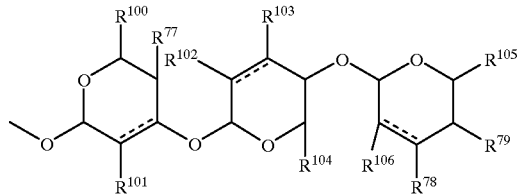

(J)

(in the formula, ---- represents a single bond or a double bond, R$^\Phi$ represents a hydrogen atom or a group represented by —CH$_2$R$^{100a}$, R$^{104}$ represents a hydrogen atom or a group represented by —CH$_2$R$^{104a}$, R$^{105}$ represents a hydrogen atom or a group represented by —CH$_2$R$^{105a}$, and R$^{100a}$, R$^{77}$, R$^{101}$, R$^{102}$, R$^{103}$, R$^{104a}$, R$^{105a}$, R$^{79}$, R$^{78}$, and R$^{106}$ independently represent a hydrogen atom or any one of the substituents defined for the aforementioned R$^{15a}$), and a group represented by the following formula (K):

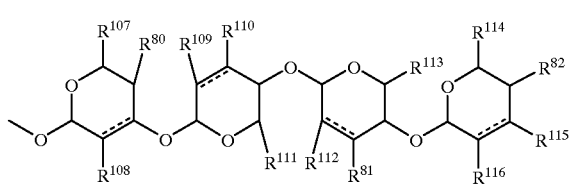

(K)

(in the formula, ---- represents a single bond or a double bond, R$^{107}$ represents a hydrogen atom or a group represented by —CH$_2$R$^{107a}$, R$^{111}$ represents a hydrogen atom or a group represented by —CH$_2$R$^{111a}$, R$^{113}$ represents a hydrogen atom or a group represented by —CH$_2$R$^{113a}$, R$^{114}$ represents a hydrogen atom or a group represented by —CH$_2$R$^{114a}$, and R$^{107a}$, R$^{80}$, R$^{108}$, R$^{109}$, R$^{110}$, R$^{111a}$, R$^{113a}$, R$^{81}$, R$^{112}$, R$^{114a}$, R$^{82}$, R$^{115}$, and R$^{116}$ independently represent a hydrogen atom or any one of the substituents defined for the aforementioned R$^{15a}$);

R$^{18a}$ represents a formyl group, a group represented by —CH=CHR$^{83}$ (in the formula, R$^{83}$ represents any one of the substituents defined for the above R$^{26}$), a group represented by —CH=NOR$^{84}$ (in the formula, R$^{84}$ represents any one of the substituents defined for the above R$^{27}$), or a group represented by —CH(X$^2$R$^{85}$)$_2$ (in the formula, X$^2$ represents any one of the substituents defined for the above X$^1$, and R$^{85}$ represents any one of the substituents defined for the above R$^{28}$); and R$^{19a}$ represents a hydroxyl group or a substituted or unsubstituted lower alkoxyl group:

provided that:

the aforementioned derivative wherein R$^{15a}$, R$^{11a}$, and R$^{5a}$ represent a hydroxyl group, R$^{18a}$ represents a formyl group, and R$^{19a}$ represents a methoxy group is excluded; the aforementioned derivative wherein R$^{15a}$ and R$^{5a}$ independently represent a hydroxyl group or a lower alkanoyloxy group, R$^{11a}$ represents a hydroxyl group, a lower alkanoyloxy group, or a group represented by formula (F), R$^{18a}$ represents a formyl group, and R$^{19a}$ represents a hydroxyl group is excluded; a compound represented by the following formula (Ib):

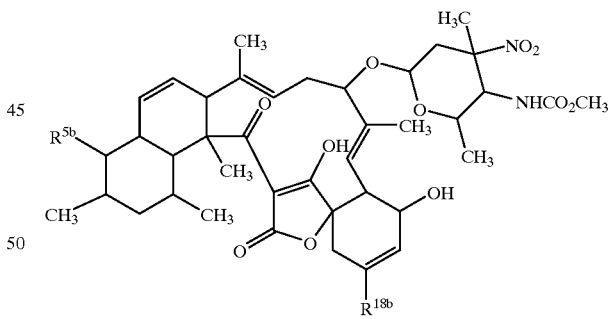

(Ib)

-continued

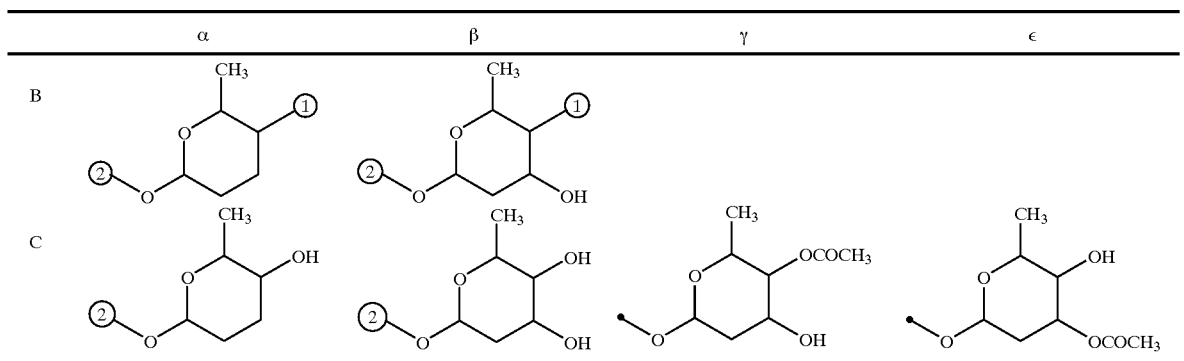

(in the formula,
$R^{5b}$ represents a group represented by Aα-Bα-Bβ-Cα (A α substitutes for $R^{5b}$ at ●, Aα-Bα means that ① of Aα and ② of Bβ are bound to each other, and in the other definitions, ① and ② are bound to each other in the same manner) and $R^{18b}$ represents a formyl group;
$R^{5b}$ represents a group represented by Aα-Bα-Cβ and $R^{18b}$ represents a formyl group;
$R^{5b}$ represents a group represented by Cγ (Cγ substitutes for $R^{5b}$ at ●) and $R^{18b}$ represents a formyl group;
$R^{5b}$ represents a group represented by Cε (CE substitutes for $R^{5b}$ at ●) and $R^{18b}$ represents a formyl group;
$R^{5b}$ represents a group represented by Aα-Cα and $R^{18b}$ represents a formyl group;
$R^{5b}$ represents a group represented by Aα-Bβ-Cβ and $R^{18b}$ represents a formyl group; or
$R^{5b}$ represents a group represented by Aα-Bβ-Bβ-Cα and $R^{18b}$ represents a formyl group) is excluded; and
a compound represented by the following formula (Ic):

alkyl portion or an alkylene, or a lower alkyl portion or a lower alkylene portion of the lower alkanoyloxy group, lower alkoxyl group, lower alkoxycarbonyloxy group, aroyloxyalkyl group, lower alkoxyalkyl group, lower alkoxycarbonyl group, lower alkanoyloxyalkyl group, lower alkanoyl group, aralkyloxy group, lower alkylamino group, lower alkanoylamino group, or aralkylamino group containing an alkylene portion or a lower alkylene portion may be linear or branched.

The alkyl group or an alkyl portion of a substituent containing the alkyl portion which is not specifically referred to as "lower" is herein used to mean those including a linear or branched alkyl group having 1 to 20 carbon atoms. As the alkyl portion or alkylene of the lower alkoxyalkyl group, aroyloxyalkyl group, or lower alkanoyloxyalkyl group, a linear or branched alkyl group having 1 to 20 carbon atoms may be used. More specifically, a methyl group, an ethyl group, a n-propyl group, an isopropyl group, a n-butyl group, an isobutyl group, a sec-butyl group, a tert-butyl group, a n-pentyl group, an isopentyl group, a (Ic)

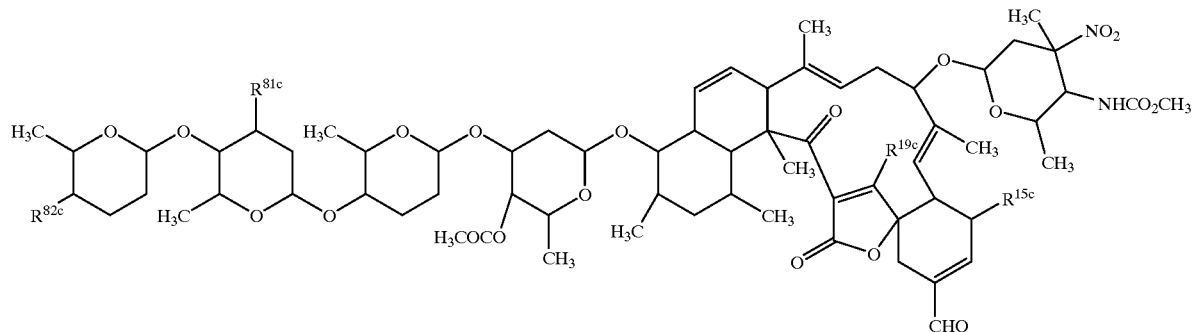

(in the formula, $R^{15c}$, $R^{81c}$, and $R^{82c}$ represents an acetoxy group and $R^{19c}$ represents a hydroxyl group, or $R^{15c}$, $R^{19c}$, $R^{81c}$, and $R^{82c}$ represent a methoxy group) is excluded. The compound represented by the aforementioned formula (Ia) or a salt thereof is useful as, for example, an active ingredient of a medicament, preferably an active ingredient of an antibacterial agent, an anticancer agent, an anti-Piroplasma agent, an anti-parasitic agent, an anti-inflammatory agent, a hypolipidemic agent, an agent for inducing apoptosis or the like.

BEST MODE FOR CARRYING OUT THE INVENTION

The meanings of the terms used in the specification are as follows. An alkyl group or a lower alkyl group as well as an n-hexyl group, a n-heptyl group, a n-octyl group, a n-nonyl group, a n-decyl group, a n-undecyl group, n-octadecyl group, corresponding alkylenes and so forth may be used.

The alkyl group or an alkyl portion of a substituent containing the alkyl portion which is specifically referred to as "lower" is herein used to mean those including a linear or branched alkyl group having 1 to 8 carbon atoms. As the lower alkyl portion of the lower alkyl group, lower alkylamino group, lower alkoxyl group, lower alkoxycarbonyloxy group, lower alkoxyalkyl group, lower alkoxycarbonyl group, lower alkanoyl group, lower alkanoyloxy group, lower alkanoyloxyalkyl group, and lower alkanoylamino group, a straight or branched alkyl group having 1 to 8 carbon atoms is preferred. More specifically, a methyl group, an ethyl group, a n-propyl group, an isopropyl group, a n-butyl group, an isobutyl group, a sec-butyl group, a tert-butyl group, a n-pentyl group, an isopentyl group, a n-hexyl group, a n-heptyl group, a n-octyl group and so forth may be used.

As a lower alkenyl portion of the lower alkenoyloxy group, a linear or branched alkenyl group having 2 to 8 carbon atoms may be used. More specifically, for example, a vinyl group, an allyl group, a crotyl group, a prenyl group, a 3-butenyl group, a 2-pentenyl group, a 4-pentenyl group, a 2-hexenyl group, a 5-hexenyl group and so forth may be used as the lower alkenyl portion.

As an aryl portion of the aryl group or a substituent containing an aryl portion (the aryloxy group, arylamino group, arylsulfonyloxy group, aroyloxy group, aroyloxyalkyl group, aroylamino group), monocyclic or bi- or tricyclic aryl groups may be used. The ring may be a condensed ring. The number of carbon atoms constituting the ring is preferably about 6 to 14. More specifically, examples of the aryl group include, for example, a phenyl group, a naphthyl group, an antholyl group and so forth.

As an aralkyl portion of the aralkyloxy group or aralkylamino group, an aralkyl group consisting of a combination of the aforementioned lower alkylene group and the aryl group may be used. Aralkyl groups having 7 to 15 carbon atoms, for example, a benzyl group, a phenethyl group, a benzhydryl group, a naphthylmethyl group and so forth may be suitably used. As an heteroaryl portion of the heteroarylamino group, a monocyclic or bi- or tricyclic heteroaryl group may be used, and the ring may be a condensed ring. The number of ring-constituting atoms is preferably about 5 to 14, and the ring may contain one or more hetero atoms selected from, for example, the group consisting of an oxygen atom, a nitrogen atom, and a sulfur atom. As the heteroaryl portion, for example, a furyl group, a thienyl group, a pyrrolyl group, an imidazolyl group, a triazolyl group, a tetrazolyl group, a thiadiazolyl group, a pyridyl group, an indolyl group, a quinolyl group, an isoquinolyl group, a quinoxalinyl group, a quinazolinyl group, a thiazolyl group, a benzothiazolyl group, a benzimidazolyl group, an oxazolyl group and so forth may be used.

Where a functional group is referred to as "substituted or unsubstituted", the definition is herein used to mean that the functional group may have one or more substituents which may be the same or different. Examples of substituents substituting on an alkyl portion or an alkylene portion, a lower alkyl portion or a lower alkylene portion, or the lower alkyl group, lower alkanoyloxy group, lower alkoxyl group, lower alkoxycarbonyloxy group, lower alkenoyloxy group, lower alkoxyalkyl group, lower alkoxycarbonyl group, lower alkanoyloxyalkyl group, lower alkanoyl group, lower alkylamino group, or lower alkanoylamino group are one to three substituents selected from the group consisting of a halogen atom ("halogen atom" used in this specification may be any of a fluorine atom, a chlorine atom, a bromine atom and an iodine atom), a hydroxyl group, a formyl group, a carboxyl group, a carbamoyl group, a mercapto group, an amino group, a mono- or di(loweralkyl)amino group, a nitro group, a lower alkyl group, a lower alkoxyl group, a lower alkoxyalkoxy group, a lower alkoxyalkoxyalkoxy group, a lower alkoxycarbonyl group, a lower alkylthio group (a lower alkyl portion of the lower alkylthio group is the same as that defined above), a lower alkanoyl group, and a lower alkanoyloxy group. The lower alkyl group of the mono- or di(loweralkyl)amino group is the same as the aforementioned lower alkyl group. The lower alkyl group, lower alkoxyl group, lower alkoxycarbonyl group, lower alkanoyl group, and lower alkanoyloxy group are the same as those defined above. An lower alkoxy portion of the lower alkoxyalkoxy group and lower alkoxyalkoxyalkoxy group is the same as the aforementioned lower alkoxyl group, and an alkoxy portion and an alkoxy portion of an alkoxyalkoxy portion mean a linear or branched alkoxy having 1 to 20 carbon atoms derived from a linear or branched alkyl group having 1 to 20 carbon atoms.

Examples of substituents that substitute on ring moieties of the substituted aroylamino group, substituted aroyloxy group, substituted aroyloxyalkyl group, substituted aryl group, substituted arylamino group, substituted aryloxy group, substituted arylsulfonyloxy group, substituted aralkylamino group, substituted aralkyloxy group, substituted heteroaroylamino group and so forth are one to four substituents selected from the group consisting of a halogen atom, a hydroxyl group, a formyl group, a carboxyl group, a carbamoyl group, a mercapto group, an amino group, a mono- or di(loweralkyl)amino group, a nitro group, a lower alkyl group, a lower alkoxyl group, a lower alkoxycarbonyl group, a lower alkylthio group, a lower alkanoyl group, an aryl group, and a lower alkanoyloxy group. When the rings have two or more substituents, they may be the same or different. The lower alkyl in the mono- or di(loweralkyl) amino group is the same as the aforementioned lower alkyl. The lower alkyl group, lower alkoxyl group, lower alkoxycarbonyl group, lower alkylthio group, lower alkanoyl group, aryl group, and lower alkanoyloxy group are the same as those defined above.

As the active ingredient of the medicament of the present invention, the compound represented by the aforementioned formula (I) in the free form as well as a physiologically acceptable salt thereof may be used. Examples of the salts include acid addition salts such as inorganic acid salts and organic acid salts; base addition salts such as metal salts, ammonium salts, and organic ammonium salts; and amino acid addition salts. Examples of the acid addition salts include inorganic acid salts such as hydrochlorides, hydrobromides, sulfates, and phosphates, and organic acid salts such as formates, acetates, benzoates, maleates, fumarates, succinates, tartrates, citrates, oxalates, methanesulfonates, p-toluenesulfonates, aspartates, and glutamates. Examples of the metal salts include, for example, alkali metal salts such as lithium salts, sodium salts and potassium salts, alkaline earth metal salts such as magnesium salts and calcium salts, aluminum salts, zinc salts and so forth. Examples of the ammonium salts include an ammonium, a tetramethylammonium and so forth, and examples of the organic ammonium salts include addition salts of morpholine, piperidine and so forth. Examples of the amino acid addition salts include, for example, addition salts of glycine, phenylalanine, lysine and so forth.

The compounds represented by the aforementioned formulas (I) and (Ia) have asymmetric carbon atoms, and accordingly, stereoisomers such as optically active compounds and diastereoisomers exist. As the active ingredients of the medicaments of the present invention, any substances including stereoisomers in pure forms, any mixtures of stereoisomers, racemates and so forth may be used. Where the compounds represented by the formulas (I) and (Ia) have an alkenyl group, the group may be in either of Z- or E-configuration. Where the compounds have a carbon/nitrogen double bond, they may be either a syn-isomer or anti-isomer as for the syn/anti isomerism resulting from the carbon/nitrogen double bond. As the active ingredients of the medicaments of the present invention, any of the geometrical isomers in pure forms and mixtures of the geometrical isomers may be used. As the active ingredients of the medicaments of the present invention, the compounds represented by the aforementioned formulas (I) and (Ia) and salts thereof, as well as any hydrates thereof and any solvates thereof may be used. Although the types of solvents that form the solvates are not particularly limited so long as they are physiologically acceptable solvents. For example, ethanol and so forth may be used.

Typical compounds of formula (I) and formula (Ia) preferably used as the active ingredients of the medicaments of the present invention will be shown below. However, the active ingredients of the medicaments of the present invention are not limited to these compounds.

TABLE 1(1)

Specific examples of compounds of formula (I)

| Compound No. | $R^{15}$ | $R^{16}$ | $R^{19}$ | $R^{33}$ | $R^{56}$ |
|---|---|---|---|---|---|
| 1 | OH | CHO | OH | OH | OH |
| 2 | OCOCH$_3$ | CHO | OH | OCOCH$_3$ | OCOCH$_3$ |
| 3 | OCH$_3$ | CHO | OCH$_3$ | OCH$_3$ | OCH$_3$ |
| 4 | OH | CH$_2$OH | OH | OH | OH |
| 5 | OH | COOH | OH | OH | OH |

TABLE 1(2)

Specific examples of compounds of formula (I)

| Compound No. | $R^5$ | $R^{11}$ | $R^{15}$ | $R^{18}$ |
|---|---|---|---|---|
| 6 | (trisaccharide structure) | A | OH | CHO |
| 7 | (disaccharide structure) | A | OH | CHO |
| 8 | (monosaccharide structure) | A | OH | CHO |
| 9 | OH | A | OH | CHO |

TABLE 1(2)-continued
Specific examples of compounds of formula (I)
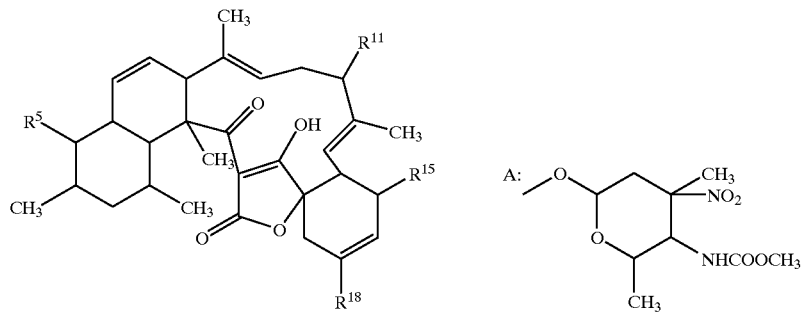
| Compound No. | $R^5$ | $R^{11}$ | $R^{15}$ | $R^{18}$ |
|---|---|---|---|---|
| 10 | OH | A | $OCOCH_3$ | CHO |
| 11 | OH | OH | OH | CHO |
TABLE 1(3)
Specific examples of compounds of formula (I)
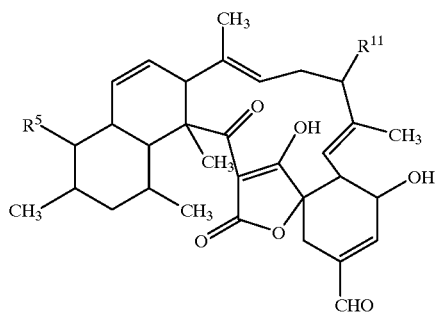
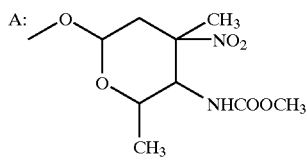
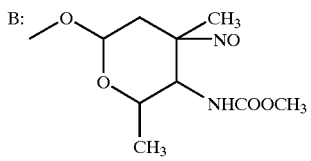
| Compound No. | $R^5$ | $R^{11}$ |
|---|---|---|
| 12 |  | A |

TABLE 1(3)-continued
Specific examples of compounds of formula (I)
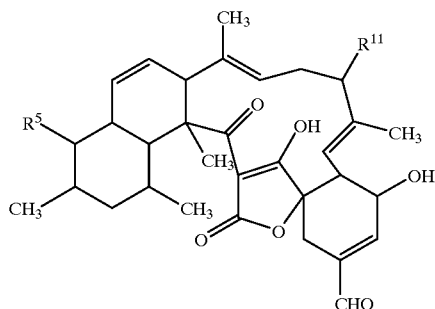
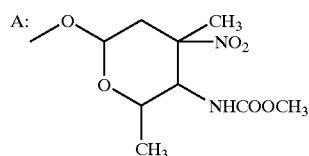
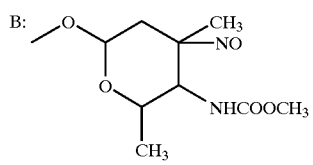
| Compound No. | $R^5$ | $R^{11}$ |
|---|---|---|
| 13 | ![structure] | A |
| 14 | ![structure] | A |
| 15 | ![structure] | A |

TABLE 1(3)-continued
Specific examples of compounds of formula (I)
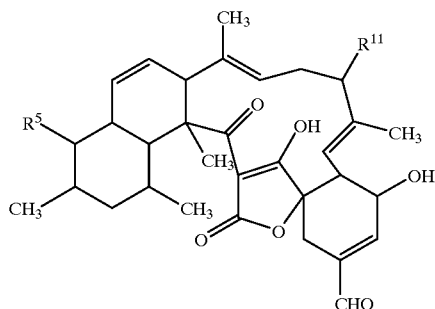
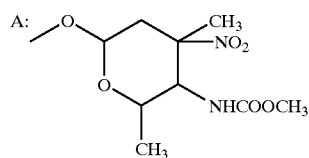
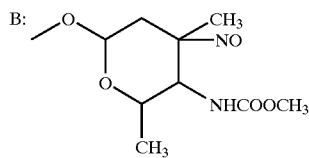
| Compound No. | $R^5$ | $R^{11}$ |
|---|---|---|
| 16 | | A |
| 17 | | B |

TABLE 1(4)

Specific examples of compounds of formula (I)

[Structure of formula (I) with R¹⁸ substituent position]

| Compound No. | R¹⁸ |
|---|---|
| 18 | CHO |
| 19 | H |

TABLE 1(5)

Specific examples of compounds of formula (Ia)

[Structure of formula (Ia) with R⁵ᵃ, R¹⁵ᵃ, R¹⁸ᵃ substituent positions]

| Compound No. | R⁵ᵃ | R¹⁵ᵃ | R¹⁸ᵃ |
|---|---|---|---|
| 20 | CH₃O-C(O)-CH₂-(OCH₂CH₂)₂-OCH₃ (via ester linkage) | CH₃O-C(O)-CH₂-(OCH₂CH₂)₂-OCH₃ (via ester linkage) | CHO |
| 21 | OSi(CH₃)₂C(CH₃)₃ | OSi(CH₃)₂C(CH₃)₃ | CHO |
| 22 | OSi(CH₃)₂C(CH₃)₃ | OH | CHO |
| 23 | OH | OSi(CH₃)₂C(CH₃)₃ | CHO |
| 24 | [trisaccharide group: methoxy-pyranose-O-pyranose(OCOCH₃,CH₃)-O-pyranose(OH,OH,CH₃)] | OH | CH=NOH |
| 25 | [disaccharide group: methoxy-pyranose(OCOCH₃,CH₃)-O-pyranose(OH,CH₃)] | OH | CH=NOH |

TABLE 1(5)-continued

Specific examples of compounds of formula (Ia)

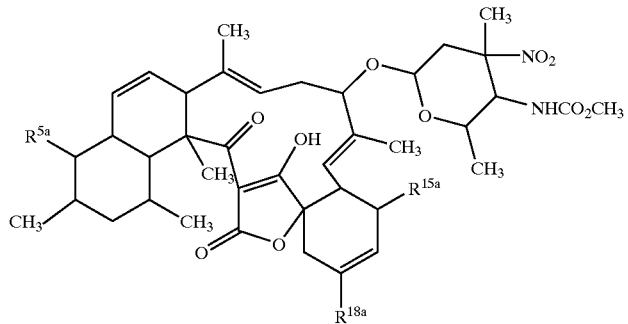

| Compound No. | $R^{5a}$ | $R^{15a}$ | $R^{18a}$ |
|---|---|---|---|
| 26 | 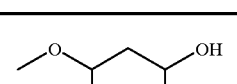 | OH | CH=NOH |

TABLE 1(6)

Specific examples of compounds of formula (Ia)

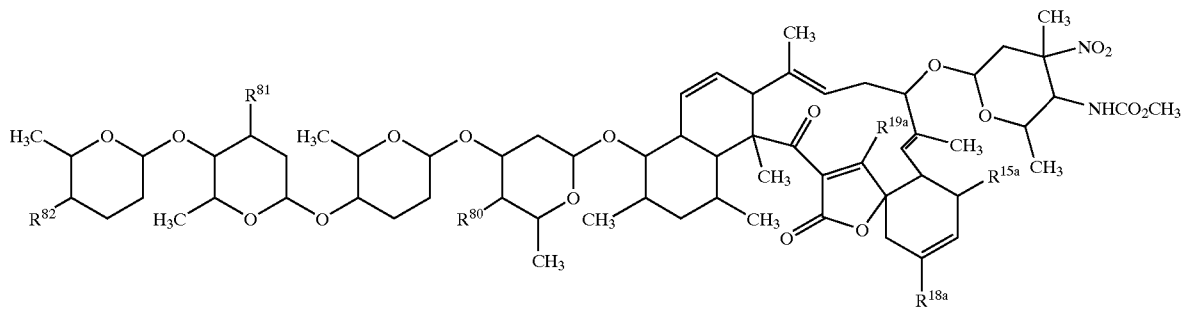

| Compound No. | $R^{15a}$ | $R^{18a}$ | $R^{19a}$ | $R^{80}$ | $R^{81}$ | $R^{82}$ |
|---|---|---|---|---|---|---|
| 27 | OH | CHO | OH | OH | OH | OH |
| 28 | OH | CHO | OH | OCOCH$_3$ | OCOCH$_3$ | OH |
| 29 | OH | CHO | OCH$_3$ | OCOCH$_3$ | OH | OH |
| 30 | OCOCH$_3$ | CHO | OCH$_3$ | OCOCH$_3$ | OCOCH$_3$ | OCOCH$_3$ |
| 31 | OH | CHO | OH | OCOCH$_3$ | OH | OSi(CH$_3$)$_2$C(CH$_3$)$_3$ |
| 32 | OSi(CH$_3$)$_2$C(CH$_3$)$_3$ | CHO | OH | OCOCH$_3$ | OH | OH |
| 33 | OSi(CH$_3$)$_2$C(CH$_3$)$_3$ | CHO | OH | OCOCH$_3$ | OH | OSi(CH$_3$)$_2$C(CH$_3$)$_3$ |
| 34 | OSi(CH$_3$)$_2$C(CH$_3$)$_3$ | CHO | OH | OCOCH$_3$ | OSi(CH$_3$)$_2$C(CH$_3$)$_3$ | OSi(CH$_3$)$_2$C(CH$_3$)$_3$ |
| 35 | OSi(CH$_3$)$_2$C(CH$_3$)$_3$ | CHO | OH | OCOCH$_3$ | OCOCH$_3$ | OSi(CH$_3$)$_2$C(CH$_3$)$_3$ |
| 36 | OSi(CH$_3$)$_2$C(CH$_3$)$_3$ | CHO | OH | OH | OH | OSi(CH$_3$)$_2$C(CH$_3$)$_3$ |
| 37 | OH | CH=CHCO$_2$CH$_3$ | OH | OCOCH$_3$ | OH | OH |
| 38 | OH | CH(OCH$_2$CH$_3$)$_2$ | OCH$_3$ | OCOCH$_3$ | OH | OH |

TABLE 1(7)

Specific examples of compounds of formula (Ia)

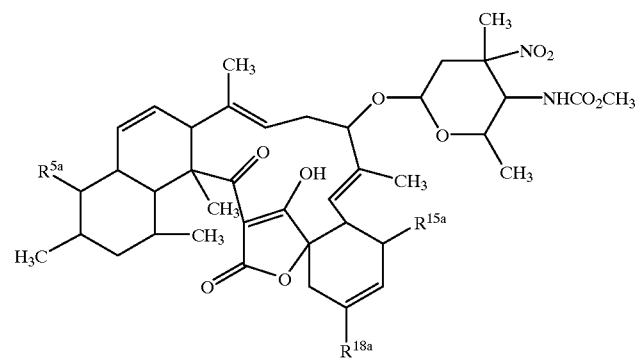

| Compound No. | $R^{15a}$ | $R^{18a}$ | $R^{19a}$ | $R^{81}$ | $R^{82}$ |
|---|---|---|---|---|---|
| 39 | $OSi(CH_3)_2C(CH_3)_3$ | CHO | $OCH_3$ | $OCH_3$ | $OSi(CH_3)_2C(CH_3)_3$ |
| 40 | OH | CHO | OH | OH | $OCH_2OCH_3$ |
| 41 | OH | CHO | OH | $OCH_2OCH_3$ | $OCH_2OCH_3$ |
| 42 | OH | CHO | OH | $OCH_2O(CH_2)_7CH_3$ | $OCH_2O(CH_2)_7CH_3$ |
| 43 | $OCH_2O(CH_2)_7CH_3$ | CHO | OH | $OCH_2O(CH_2)_7CH_3$ | $OCH_2O(CH_2)_7CH_3$ |
| 44 | $OCH_2O(CH_2)_7CH_3$ | CHO | OH | OH | $OCH_2O(CH_2)_7CH_3$ |
| 45 | OH | $CH(OCH_3)_2$ | OH | OH | OH |

TABLE 1(8)

Specific examples of compounds of formula (Ia)

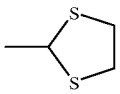

| Compound No. | $R^{5a}$ | $R^{15a}$ | $R^{18a}$ |
|---|---|---|---|
| 46 | $OCOCH_2(OCH_2CH_2)_2OCH_3$ | $OSi(CH_3)_2C(CH_3)_3$ | CHO |
| 47 | $OCOCH_2(OCH_2CH_2)_2OCH_3$ | OH | CHO |
| 48 | OH | OH | 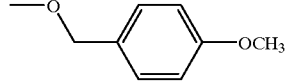 |
| 49 | 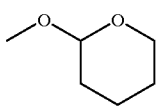 | $OCOCH_3$ | CHO |
| 50 |  | OH | CHO |

TABLE 1(8)-continued
Specific examples of compounds of formula (Ia)
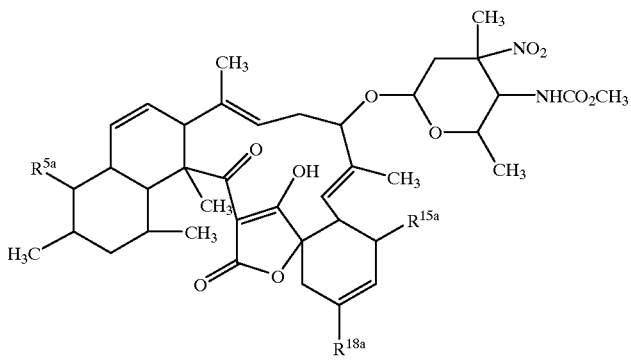
| Compound No. | $R^{5a}$ | $R^{15a}$ | $R^{18a}$ |
|---|---|---|---|
| 51 |  | OCOCH$_3$ | CHO |
TABLE 1(9)
Specific examples of compounds of formula (Ia)
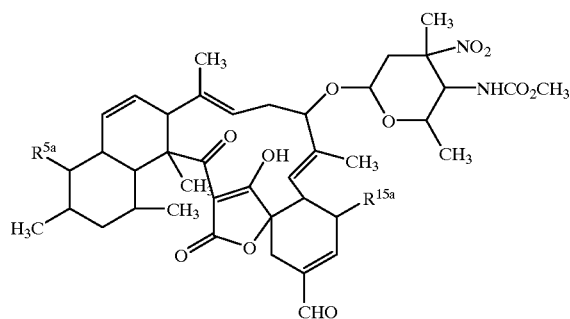
| Compound No. | $R^{5a}$ | $R^{15a}$ |
|---|---|---|
| 52 |  | OH |
| 53 | 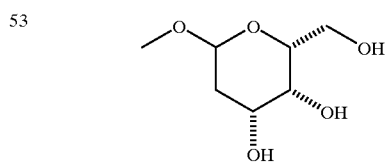 | OH |
TABLE 1(9)-continued
Specific examples of compounds of formula (Ia)
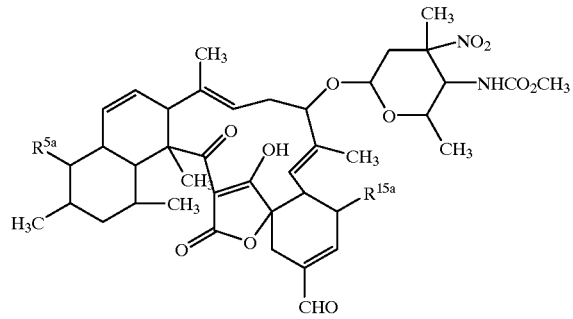
| Compound No. | $R^{5a}$ | $R^{15a}$ |
|---|---|---|
| 54 | | OCOCH$_3$ |
| 55 | | OH |

TABLE 1(9)-continued

Specific examples of compounds of formula (Ia)

| Compound No. | R$^{5a}$ | R$^{15a}$ |
|---|---|---|
| 56 | methyl 2,3,4-tri-O-benzyl pyranoside group (OCH$_3$, OCH$_2$C$_6$H$_5$, OCH$_2$C$_6$H$_5$, OCH$_2$C$_6$H$_5$) | OCOCH$_3$ |
| 57 | methyl 2,3,4-tri-O-acetyl pyranoside group (OCH$_3$, OCOCH$_3$, OCOCH$_3$, OCOCH$_3$) | OCOCH$_3$ |
| 58 | methyl 2,3,4-tri-O-acetyl pyranoside group (OCH$_3$, OCOCH$_3$, OCOCH$_3$, OCOCH$_3$) | OCOCH$_3$ |

TABLE 1 (10)

Specific examples of compounds of formula (Ia)

| Compound No. | R$^{5a}$ | R$^{15a}$ |
|---|---|---|
| 59 | methyl 2,3-di-O-acetyl-6-deoxy pyranoside group (OCH$_3$, CH$_3$, OCOCH$_3$, OCOCH$_3$) | OCOCH$_3$ |

TABLE 1 (10)-continued

Specific examples of compounds of formula (Ia)

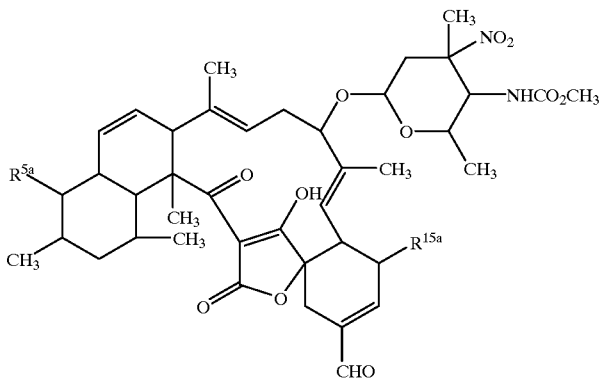

| Compound No. | R$^{5a}$ | R$^{15a}$ |
|---|---|---|
| 60 | (2-methoxy-6-methyl-5-hydroxy-5,6-dihydro-2H-pyran-3-yl) | OCOCH$_3$ |
| 61 | (2-methoxy-6-methyl-5-acetoxy-5,6-dihydro-2H-pyran-3-yl) | OCOCH$_3$ |
| 62 | (2-methoxy-6-methyl-5-triethylsilyloxy-5,6-dihydro-2H-pyran-3-yl) | OH |
| 63 | (2-methoxy-6-methyl-5-triethylsilyloxy-5,6-dihydro-2H-pyran-3-yl) | OCOCH$_3$ |
| 64 | (2-methoxy-6-(triethylsilyloxymethyl)-5-triethylsilyloxy-5,6-dihydro-2H-pyran-3-yl) | OCOCH$_3$ |
| 65 | (trisaccharide with OCOCH$_3$, OH, OCOCH$_3$, CH$_3$ groups) | OCOCH$_3$ |
| 66 | (methyl orthoester sugar with three OCOCH$_3$ groups) | OCOCH$_3$ |

TABLE 1 (11)

Specific examples of compounds of formula (Ia)

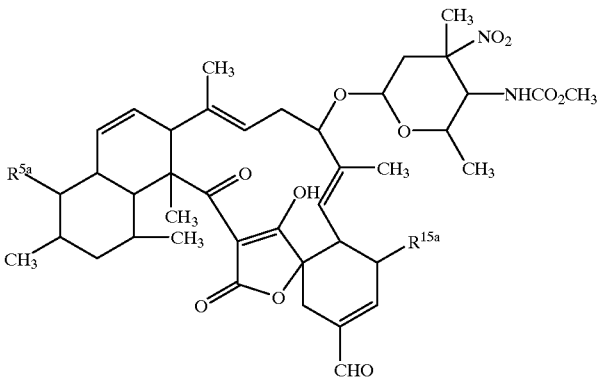

| Compound No. | $R^{5a}$ | $R^{15a}$ |
|---|---|---|
| 67 | 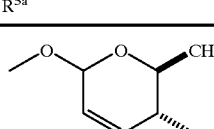 | OH |
| 68 | 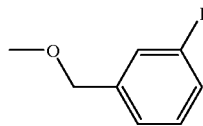 | OCOCH$_3$ |

Compounds 1, 6, 8, and 12 are disclosed in Japanese Patent Unexamined Publication No. 57-38796/1982, and Compounds 2, 9, 10, and 11 are disclosed in Japanese Patent Unexamined Publication No. 57-7479/1982. Further, Compound 3 is disclosed in the 23rd Symposium of Naturally Occurring Substances, Abstract 584 (1980), and Compounds 4, 5, and 7 are disclosed in Japanese Patent Unexamined Publication No. 57-53498/1982. Compounds 13, 14, 15, 18, and 19 are disclosed in Japanese Patent Unexamined Publication No. 57-171997/1982, and Compounds 16 and 17 are disclosed in Japanese Patent Unexamined Publication No. 56-122392/1981. Further, methods for producing novel compounds of formula (Ia) falling within the scope of formula (I) are explained in the specification, and specific methods for producing said novel compounds are described in detail in Examples. Therefore, those skilled in the art can easily prepare any compounds falling within the scope of formula (I).

The compounds represented by the aforementioned formula (I) and the physiologically acceptable salts thereof have an apoptosis inducing action, and they may be used as medicaments for preventive and/or therapeutic treatment of diseases that can be preventively and/or therapeutically treated by the induction of apoptosis. Further, they can also be used as reagents for inducing apoptosis in the fields of biochemistry, genetic engineering and so forth. While it is not intended to be bound by any specific theory, the medicaments of the present invention have an action for inducing apoptosis by activating caspase, which is suppressed by increased expression of proteins belonging to the Bcl-2 family. The apoptosis inducing action of the compounds represented by the aforementioned formula (I) or physiologically acceptable salts thereof can easily be confirmed by the methods specifically shown in Examples of the specification.

The term "apoptosis inducing action" or similar terminologies thereof herein used should be construed in their broadest sense including an apoptosis inducing action of the compound represented by formula (I) or a physiologically acceptable salt thereof, per se, as well as an enhancing action on apoptosis induction by various anticancer agents or anti-Fas antibodies, an enhancing action on the process of already induced apoptosis and so forth. The medicaments of the present invention may be used for preventive and/or therapeutic treatment of diseases resulting from increased expression of the Bcl-2 family proteins, for example, cancers, AIDS, ARC (AIDS related conditions), osteoarthritis, autoimmune diseases such as rheumatoid arthritis and systemic lupus erythematodes, collagenosis such as Sjögren's syndrome, arteriosclerosis and so forth. However, diseases treatable by the medicaments of the present invention are not limited to the diseases exemplified above.

One or more of substances, per se, selected from the group consisting of the compounds of formula (I) and physiologically acceptable salts thereof, and hydrates thereof and solvates thereof may be administered as the medicaments of the present invention. It is generally desirable, however, that they are administered as a pharmaceutical composition comprising the aforementioned substance as the active ingredient together with one or more kinds of pharmaceutical additives. Types of the pharmaceutical compositions can be suitably chosen from various kinds of formulations suitable for oral administration or parenteral administration depending on the type of the active ingredient, purpose of administration and so forth. Although doses and administration frequencies of the medicaments of the present invention are not particularly limited, it is desirable to appropriately increase or decrease the dose or frequency depending on a dosage form, the age, body weight and conditions of a patient and so forth. In general, they are preferably administered once to four times a day in an amount of 0.01 to 20 mg/kg per day for adults. The medicaments of the present invention may be used in combination with other drugs such as anticancer agents, antibacterial agents, anti-inflammatory agents or the like. Pharmaceutical compositions containing the active ingredient of the present invention and an active ingredient having the aforementioned efficacy may be administered.

Examples of formulations suitable for oral administration include, for example, tablets, capsules, powders, granules, subtilized granules, solutions, suspensions, syrups, chewable tablets and so forth. Examples of formulations suitable for parenteral administration include, for example, injections for intravenous administration, intramuscular administration, or subcutaneous administration, drip infusions, eye drops, ear drops, suppositories, ointments, creams, transdermal preparations, transmucosal preparations, inhalants, patches and so forth. However, formulations of the medicaments of the present invention are not limited to these examples. These formulations are preferably prepared as unit dosage forms.

For the manufacture of the pharmaceutical compositions, one or more kinds of pharmaceutical additives widely used in the art may be used. The pharmaceutical additives may be chosen by those skilled in the art depending on the forms of formulations, and the formulations can be prepared in a conventional manner. For the manufacture of tablets, for example, excipients such as lactose, glucose, sucrose, mannitol and methylcellulose, disintegrating agents such as starch, sodium arginate, carboxymethylcellulose calcium and crystalline cellulose, lubricants such as magnesium stearate and talc, binders such as gelatin, polyvinyl alcohol, polyvinylpyrrolidone, hydroxypropylcellulose and methylcellulose, surfactants such as sucrose fatty acid esters and sorbit fatty acid esters and so forth may be used in a conventional manner. Tablets containing 15 to 300 mg of the active ingredient per tablet are preferred.

For the manufacture of granules, for example, excipients such as lactose and sucrose, disintegrating agents such as starch, binders such as gelatin and so forth may be used in a conventional manner. For the manufacture of powdered drugs including powders, for example, excipients such as lactose and mannitol and so forth may be used in a conventional manner. For the manufacture of capsules, for example, gelatin, water, sucrose, gum arabic, sorbit, glycerol, crystalline cellulose, magnesium stearate, talc and so forth may be used in a conventional manner. Capsules containing 15 to 300 mg of the active ingredient per capsule are preferred. For the manufacture of syrups, for example, saccharides such as sucrose, water, ethanol and so forth may be used in a conventional manner.

For the manufacture of ointments, for example, ointment base materials such as Vaseline, liquid paraffin, lanolin, and macrogol, emulsifiers such as sodium lauryl lactate, benzalkonium chloride, sorbitan mono-fatty acid esters, carboxymethylcellulose sodium, gum arabic and so forth may be used in a conventional manner. For the manufacture of injections, for example, solvents such as water, physiological saline, vegetable oils (e.g., olive oil, peanut oil and the like), ethyl oleate, and propylene glycol, solubilizers such as sodium benzoate, sodium salicylate, and urethane, isotonic agents such as sodium chloride and glucose, preservatives such as phenol, cresol, p-hydroxybenzoate, and chlorobutanol, antioxidants such as ascorbic acid and sodium pyrosulfite and so forth may be used in a conventional manner.

According to the another aspect of the present invention, novel compounds represented by formula (Ia) are provided. Methods for producing the compounds of the present invention are not particularly limited. For example, they can be synthesized according to the reaction steps explained below, and specific examples are specifically explained in detail in Examples of the specification. As for the preparation methods explained below, where the defined groups are reactive under conditions for carrying out the methods or they are not suitable for carrying out the methods, the preparation of desired compounds may be facilitated by introduction and removal of protective groups which are conventionally used in the field of synthetic organic chemistry (see, for example, T. W. Greene, Protective Groups in Organic Synthesis, John Wiley & Sons, Inc. (1981)). Further, the order of the reaction steps such as steps of introducing functional groups may be changed as required.

Preparation Method 1

The compounds of formula (Ia-2), which correspond to the compounds of formula (Ia) wherein at least one substituent selected from the group consisting of $R^{11a}$ and $R^{15a}$, and $R^{73}$ to $R^{82}$ and $R^{93}$ to $R^{116}$ in $R^{5a}$ is a group represented by $-OSi(R^{86})(R^{87})(R^{88})$ ($R^{86}$, $R^{87}$ and $R^{88}$ have the same meanings as the above defined $R^{20}$, $R^{21}$, and $R^{22}$, respectively);

the compounds of formula (Ia-3), which correspond to the compounds of formula (Ia) wherein at least one substituent selected from the group consisting of $R^{11a}$ and $R^{15a}$, and $R^{73}$ to $R^{82}$ and $R^{93}$ to $R^{116}$ in $R^{5a}$ is an acyloxy group (the acyloxy group is a substituted or unsubstituted lower alkanoyloxy group, a substituted or unsubstituted aroyloxy group, or a substituted or unsubstituted lower alkenoyloxy group); and the compounds of formula (Ia-4), which correspond to the compounds of formula (Ia) wherein at least one substituent selected from the group consisting of $R^{11a}$ and $R^{15a}$, and $R^{73}$ to $R^{82}$ and $R^{93}$ to $R^{116}$ in $R^{5a}$ is a substituted or unsubstituted lower alkoxyl group, a substituted or unsubstituted aralkyloxy group, or a substituted or unsubstituted aryloxy group, or $R^{19a}$ is a substituted or unsubstituted lower alkoxyl group can be synthesized from the compounds of formula (Ia-1) wherein at least one substituent selected from the group consisting of $R^{11a}$, $R^{15a}$, and $R^{19a}$, and $R^{73}$ to $R^{82}$ and $R^{93}$ to $R^{116}$ in $R^{5a}$ is a hydroxyl group.

Further, compounds wherein $R^{5a}$ is a group represented by $-OSi(R^{86})(R^{87})(R^{88})$ ($R^{86}$, $R^{87}$, and $R^{88}$ have the same meanings as the above defined $R^{20}$, $R^{21}$ and $R^{22}$, respectively), an acyloxy group (the acyloxy group is a substituted or unsubstituted lower alkanoyloxy group, a substituted or unsubstituted aroyloxy group, or a substituted or unsubstituted lower alkenoyloxy group), a substituted or unsubstituted lower alkoxyl group, a substituted or unsubstituted aralkyloxy group, or a substituted or unsubstituted aryloxy group can be synthesized from a corresponding compound wherein $R^{5a}$ is a hydroxyl group.

In the reaction formulas shown in the following steps 1 to 3, a series of compounds wherein $R^{5a}$ is the same as the group of (K) as defined above are shown as examples of the compounds of formulas (Ia-1), (Ia-2), (Ia-3), and (Ia-4) ($R^{107}$, $R^{111}$, $R^{113}$, and $R^{114}$ are methyl groups, $R^{108}$, $R^{109}$, $R^{110}$, $R^{112}$, $R^{115}$, and $R^{116}$ are hydrogen atoms, and ---- in formula (K) is a single bond).

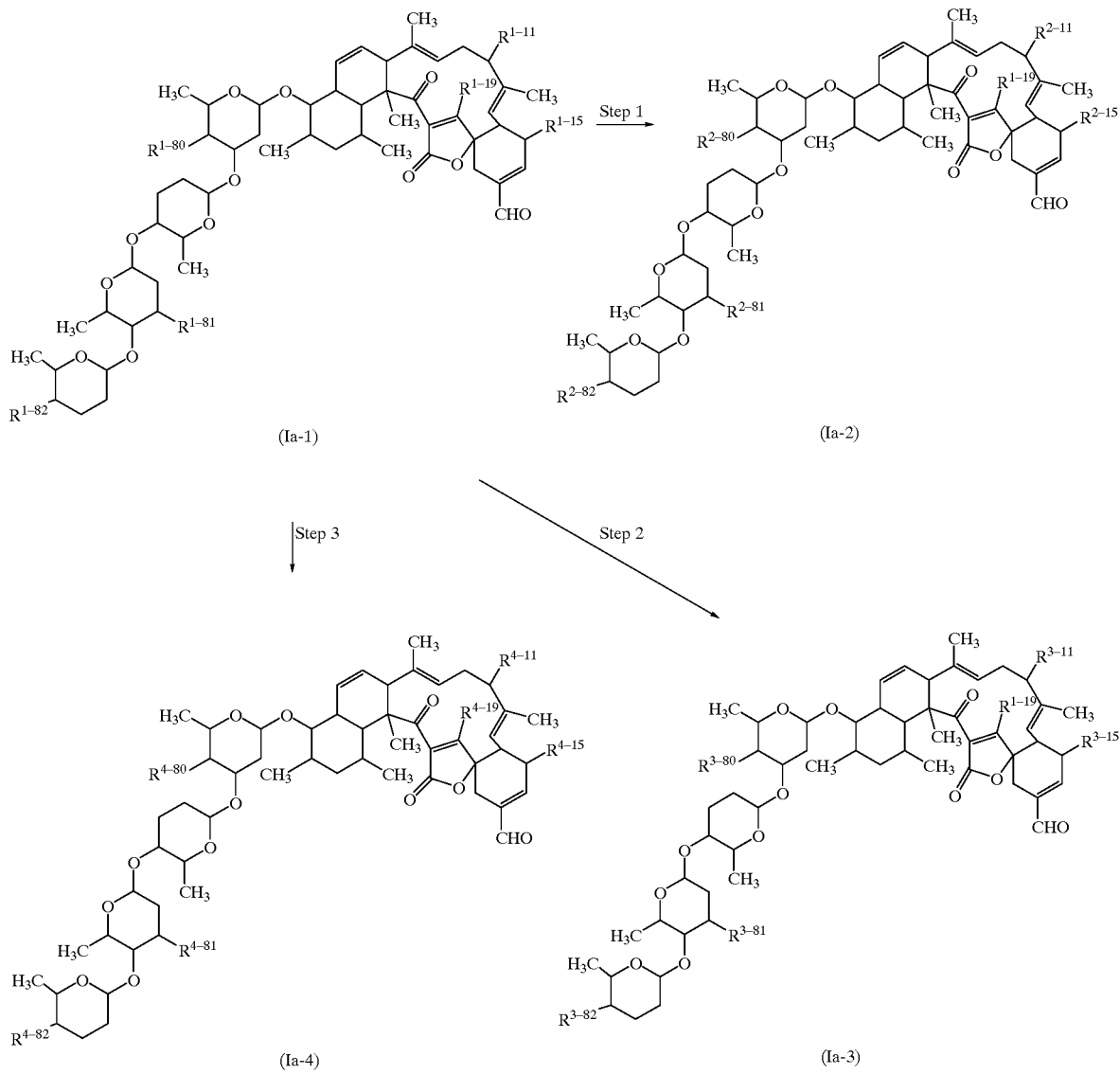

(Ia-1)

(Ia-2)

(Ia-4)

(Ia-3)

(In the formulas, at least one group selected from the group consisting of $R^{1-11}$, $R^{1-15}$, $R^{1-19}$, $R^{1-80}$, $R^{1-81}$, and $R^{1-82}$ represents a hydroxyl group, at least one group selected from the group consisting of $R^{2-11}$, $R^{2-15}$, $R^{2-80}$, $R^{2-81}$, and $R^{2-82}$ represents a group represented by $-\text{OSi}(R^{86})(R^{87})(R^{88})$ ($R^{86}$, $R^{87}$ and $R^{88}$ have the same meanings as the above defined $R^{20}$, $R^{21}$ and $R^{22}$, respectively), at least one group selected from the group consisting of $R^{3-11}$, $R^{3-15}$, $R^{3-80}$, $R^{3-81}$, and $R^{3-82}$ represents an acyloxy group (the acyloxy group has the same meaning as that defined above), at least one group selected from the group consisting of $R^{4-11}$, $R^{4-15}$, $R^{4-19}$, $R^{4-80}$, $R^{4-81}$, and $R^{4-82}$ represents a substituted or unsubstituted lower alkoxyl group, a substituted or unsubstituted aralkyloxy group, or a substituted or unsubstituted aryloxy group, $R^{1-11}$, $R^{2-11}$, $R^{3-11}$, and $R^{4-11}$ among the remaining substituents have the same meaning as the aforementioned $R^{11a}$, $R^{1-15}$, $R^{1-80}$, $R^{1-81}$, $R^{1-82}$, $R^{2-15}$, $R^{2-80}$, $R^{2-81}$, $R^{2-82}$, $R^{3-15}$, $R^{3-80}$, $R^{3-81}$, $R^{3-82}$, $R^{4-15}$, $R^{4-19}$, $R^{4-80}$, $R^{4-81}$ and $R^{4-82}$ have the same meaning as the aforementioned $R^{15a}$, and $R^{1-19}$ and $R^{4-19}$ have the same meaning as the aforementioned $R^{19a}$.)

<Step 1>

A compound of formula (Ia-2) can be synthesized by silylating the hydroxyl group of a compound of formula (Ia-1) using a suitable silylation reagent. As the silylation reagent, any of silylation reagents usually used for silylation of a hydroxyl group may be used. For example, the compound can be synthesized by allowing a compound of formula (Ia-1) to react with 1 to 100 equivalents of a silylation agent such as that of formula $(R^{86})(R^{87})(R^{88})$SiHal, $(R^{86})(R^{87})(R^{88})\text{SiOSO}_2\text{CF}_3$ (in the formulas, Hal represents a halogen atom having the same meaning as that defined above, and $R^{86}$, $R^{87}$, and $R^{88}$ have the same meanings as the above defined $R^{20}$, $R^{21}$ and $R^{22}$, respectively) or the like in an inert solvent such as acetonitrile, tetrahydrofuran, ether, dioxane, dimethylformamide, dimethyl sulfoxide, chloroform, or dichloromethane in the presence of 1 to 100 equivalents of a base such as imidazole, pyridine, triethylamine, ethyldiisopropylamine, N,N- dimethylaniline, or 2,6-lutidine. The reaction temperature is preferably −30° C. to 150° C., and the reaction time is usually 5 minutes to 150 hours.

<Step 2>

A compound of formula (Ia-3) can be synthesized by acylating the hydroxyl group of a compound of formula (Ia-1) using a suitable acylation agent. As the acylation agent to be used, any of acylation agents usually used for acylation of a hydroxyl group may be used. For example, the compound can be synthesized by allowing a compound of formula (Ia-1) to react with 1 to 100 equivalents of an acid anhydride or an acid halide without a solvent or in a solvent such as N,N-dimethylformamide, chloroform, or dichloromethane in the presence of 1 equivalent to a solvent amount of a base such as pyridine, triethylamine, N,N-dimethylaniline, ethyldiisopropylamine or 4-dimethylaminopyridine. The acyl groups in the aforementioned acylation agents have the same meaning as the acyl group of the aforementioned acyloxy group.

Further, a compound of formula (Ia-3) can also be synthesized by allowing a compound of formula (Ia-1) to react with 1 to 100 equivalents of a carboxylic acid in a solvent such as N,N-dimethylformamide, chloroform or dichloromethane in the presence of 1 to 100 equivalents of a base such as pyridine, triethylamine, N,N-dimethylaniline, ethyldiisopropylamine, or 4-dimethylaminopyridine and 1 to 100 equivalents of a condensing agent such as 1,3-dicyclohexylcarbodiimide, 1-ethyl-3-(3-dimethylaminopropyl)carbodiimide, or carbonyldiimidazole. The reaction temperature is preferably −30° C. to 150° C., and the reaction time is usually 5 minutes to 150 hours.

<Step 3>

A compound of formula (Ia-4) can be synthesized by alkylating the hydroxyl group of a compound of formula (Ia-1) using a suitable alkylation reagent. As the alkylation reagent, any of alkylation reagents usually used for alkylation of a hydroxyl group may be used. For example, the compound can be synthesized by allowing a compound of formula (Ia-1) to react with 1 to 50 equivalents of dimethyl sulfate, diazomethane, trimethylsilyldiazomethane, an alkyl halide, an alkoxyalkyl halide, a trialkoxytetrafluoroborate or the like in an inert solvent such as methanol, acetonitrile, tetrahydrofuran, dimethyl sulfoxide, dimethylformamide, chloroform, or dichloromethane in the presence of, if necessary, 1 to 50 equivalents of a base such as sodium hydride, silver oxide, potassium carbonate, diisopropylethylamine, pyridine, triethylamine, N,N-dimethylaniline, or 1,8-bis(dimethylamino)naphthalene. The reaction temperature is preferably −30° C. to 150° C., and the reaction time is usually 5 minutes to 150 hours.

The compound of formula (Ia-4) can also be synthesized by allowing a compound of formula (Ia-1) to react with 1 to 50 equivalents of a substituted or unsubstituted aralkyl trichloroimidate or the like in an inert solvent such as acetonitrile, tetrahydrofuran, dimethyl sulfoxide, dimethylformamide, chloroform, toluene, or dichloromethane in the presence of 0.01 to 50 equivalents of an acid such as camphorsulfonic acid or trifluoromethanesulfonic acid. The reaction temperature is preferably −30° C. to 150° C., and the reaction time is usually 5 minutes to 150 hours.

Furthermore, the compound of formula (Ia-4) can be synthesized by allowing a compound of formula (Ia-1) to react with 1 to 50 equivalents of a substituted or unsubstituted aryl alcohol or the like in an inert solvent such as acetonitrile, tetrahydrofuran, dimethyl sulfoxide, dimethylformamide, chloroform, or dichloromethane in the presence of 1 to 50 equivalents of a phosphine such as $(C_6H_5)_3P$ or $(C_4H_9)_3P$ and 1 to 50 equivalents of a regent such as diethylazodicarboxylate or 1,1'-(azodicarbonyl) dipiperazine. The reaction temperature is preferably −30° C. to 100° C., and the reaction time is usually 5 minutes to 150 hours.

Preparation Method 2

The compounds of formula (Ia-6) (in the formula, $R^{5-11}$ and $R^{5-15}$ have the same meanings as the above defined $R^{11a}$ and $R^{15a}$, $R^{5-5}$ has the same meaning as the above defined $R^{5a}$, $R^{5-19}$ has the same meaning as the above defined $R^{19a}$, and $R^{5-18a}$ has the same meaning as the above defined $R^{26}$) that correspond to the compounds of formula (Ia) wherein $R^{18a}$ is a group represented by —CH=CHR$^{89}$ ($R^{89}$ has the same meaning as the above defined $R^{26}$, and the configuration of the double bond may be either in Z or E, or a mixture thereof);

the compounds of formula (Ia-7) (in the formula, $R^{5-11}$ and $R^{5-15}$ have the same meanings as the above defined $R^{11a}$ and $R^{15a}$, $R^{5-5}$ has the same meaning as the above defined $R^{5a}$, $R^{5-19}$ has the same meaning as the above defined $R^{19a}$, and $R^{5-18b}$ has the same meaning as the above defined $R^{27}$) that correspond to the compounds of formula (Ia) wherein $R^{18a}$ is a group represented by —CH=NOR$^{90}$ ($R^{90}$ has the same meaning as the above defined $R^{27}$, and as for the syn/anti isomerism resulting from the carbon/nitrogen double bond, the compounds may be a syn-isomer or anti-isomer or a mixture thereof); and the compounds of formula (Ia-8) (in the formula, $R^{5-11}$ and $R^{5-15}$ have the same meanings as the above defined $R^{11a}$ and $R^{15a}$, $R^{5-5}$ has the same meaning as the above defined $R^{5a}$, $R^{5-19}$ has the same meaning as the above defined $R^{19a}$, $R^{5-18c}$ has the same meaning as the above defined $R^{28}$, and $X^3$ has the same meaning as the above defined $X^1$) that correspond to the compounds of formula (Ia) wherein $R^{18a}$ is a group represented by —CH($X^3R^{5-18c}$)$_2$ (in the formula, $X^3$ has the same meaning as the above defined $X^1$, and $R^{5-18c}$ has the same meaning as the above defined $R^{28}$) can be prepared from the compounds of formula (Ia-5) (in the formula, $R^{5-11}$ and $R^{5-15}$ have the same meanings as the above defined $R^{11a}$ and $R^{15a}$, $R^{5-5}$ has the same meaning as the above defined $R^{5a}$, and $R^{5-19}$ has the same meaning as the above defined $R^{19a}$) that correspond to the compounds of formula(Ia) wherein $R^{18a}$ is a formyl group according to the following method.

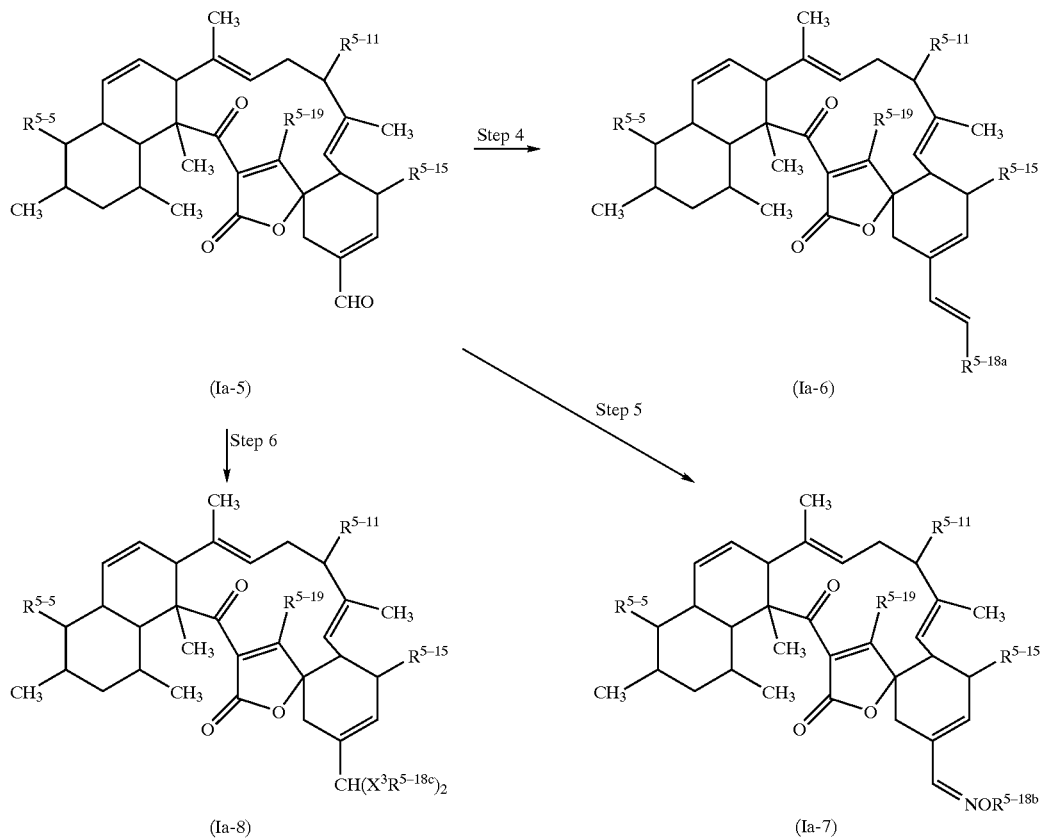

(In the formulas, $R^{5-11}$ and $R^{5-15}$ have the same meanings as the above defined $R^{11a}$ and $R^{15a}$, respectively, $R^{5-5}$ has the same meaning as the above defined $R^{5a}$, $R^{5-19}$ has the same meaning as the above defined $R^{19a}$, $R^{5-18a}$ has the same meaning as the above defined $R^{26}$, $R^{5-18b}$ has the same meaning as the above defined $R^{27}$, $R^{5-18c}$ has the same meaning as the above defined $R^{28}$, and $X^3$ has the same meaning as the above defined $X^1$.)

<Step 4>

A compound of formula (Ia-6) can be prepared by dissolving a compound of formula (Ia-5) in an inert solvent such as toluene, methanol, acetonitrile, tetrahydrofuran, ether, dioxane, dimethylformamide, dimethyl sulfoxide, chloroform or dichloromethane, and allowing the compound to react with 1 to 100 equivalents of a compound represented by the general formula $(C_6H_5)_3P=CHR^{89}$ ($R^{89}$ has the same meaning as the above defined $R^{26}$) or allowing the compound to be treated with 1 to 100 equivalents of a reagent represented by the formula $(R^{91}O)_2P(O)CH_2R^{89}$ ($R^{89}$ has the same meaning as the above defined $R^{26}$, and $R^{91}$ represents a lower alkyl group having the same meaning as that defined above) or the like in the presence of 1 to 100 equivalents of a base such as sodium hydride, sodium amide, or sodium alkoxide. The reaction temperature is preferably −78° C. to 150° C., and the reaction time is usually 5 minutes to 100 hours.

<Step 5>

A compound of formula (Ia-7) can be synthesized by adding 1 to 100 equivalents of a compound represented by the formula $H_2NOR^{90}$ ($R^{90}$ has the same meaning as the above defined $R^{27}$) to a compound of formula (Ia-5) in an inert solvent such as methanol, ethanol, acetonitrile, tetrahydrofuran, ether, dioxane, dimethylformamide, dimethyl sulfoxide, chloroform, or dichloromethane in the presence of 1 to 100 equivalents of a base such as pyridine, triethylamine, ethyldiisopropylamine, or 4-dimethylaminopyridine. The reaction temperature is preferably −50° C. to 150° C., and the reaction time is usually 5 minutes to 100 hours.

<Step 6>

A compound of formula (Ia-8) can be prepared by allowing a compound of formula (Ia-5) to react with 1 equivalent to a solvent amount of a lower alcohol compound or a lower thiol compound represented by the formula $R^{92}X^4H$ or $HX^4(CH_2)_tX^4H$ ($R^{92}$ represents a lower alkyl group having the same meaning as that defined above, $X^4$ has the same meaning as the above defined $X^1$, and t is 2 or 3) without a solvent or in an inert solvent such as acetonitrile, tetrahydrofuran, ether, dioxane, dimethylformamide, dimethyl sulfoxide, chloroform or dichloromethane. In the reaction, a catalytic amount to 100 equivalents of an acid such as hydrochloric acid, p-toluenesulfonic acid, or trifluoroborane ether complex can be added as required. The reaction temperature is preferably −60° C. to 150° C., and the reaction time is usually 5 minutes to 100 hours.

Preparation Method 3

The compounds of formula (Ia-10) (in the formula, $R^{9-11}$ and $R^{9-15}$ have the same meanings as the above defined $R^{11a}$ and $R^{15a}$, $R^{9-18}$ has the same meaning as the above defined $R^{18a}$, and $R^{9-19}$ has the same meaning as the above defined $R^{19a}$) that correspond to the compounds of formula (Ia) wherein $R^{5a}$ is, for example, a group represented by the following formula:

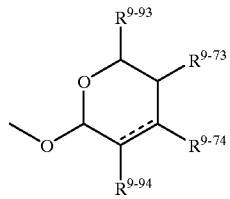

(in the formula, ---- has the same meaning as that defined above, $R^{9-93}$ has the same meaning as the above defined $R^{93}$, and $R^{9-73}$, $R^{9-74}$, and $R^{9-94}$ have the same meanings as the above defined $R^{73}$, $R^{74}$, and $R^{94}$, respectively) can be prepared from the compounds of formula (Ia-9) (in the formula, $R^{9-11}$ and $R^{9-15}$ have the same meanings as the above defined $R^{11a}$ and $R^{15a}$, $R^{9-18}$ has the same meaning as the above defined $R^{18a}$, and $R^{9-19}$ has the same meaning as the above defined $R^{19a}$) that correspond to the compounds of formula(Ia) wherein $R^{5a}$ is a hydroxyl group according to the following method.

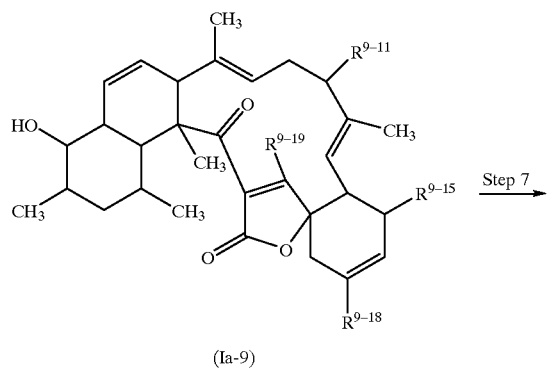

(Ia-9)

Step 7

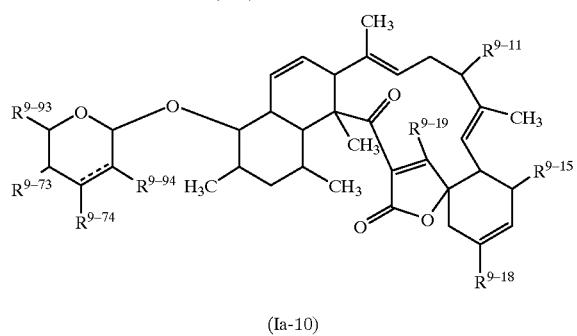

(Ia-10)

(In the formula, ---- represents a single bond or a double bond, $R^{9-11}$ and $R^{9-15}$ have the same meanings as the above defined $R^{11a}$ and $R^{15a}$, $R^{9-18}$ has the same meaning as the above defined $R^{18a}$, $R^{9-19}$ has the same meaning as the above defined $R^{19a}$, $R^{9-94}$ has the same meaning as the above defined $R^{94}$, $R^{9-74}$ has the same meaning as the above defined $R^{74}$, $R^{9-75}$ has the same meaning as the above defined $R^{75}$, and $R^{9-93}$ has the same meaning as the above defined $R^{93}$.)

<Step 7>

A compound of formula (Ia-10) can be synthesized by dissolving a compound of formula (Ia-9) in an inert solvent such as toluene, acetonitrile, tetrahydrofuran, ether, dichloromethane, or 1,2-dichloroethane and allowing the compound to react with 1 to 100 equivalents of a compound represented by the following formula:

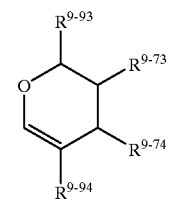

(in the formula, $R^{9-93}$ has the same meaning as the above defined $R^{9}3$, $R^{9-73}$ and $R^{9-74}$ have the same meanings as the above defined $R^{73}$ and $R^{74}$, and $R^{9-94}$ has the same meaning as the above defined $R^{94}$) in the presence of 0.01 to 100 equivalents of an acid such as camphorsulfonic acid, p-toluenesulfonic acid and triphenylphosphine hydrobromide. The reaction temperature is preferably −30° C. to 150° C., and the reaction time is usually 5 minutes to 150 hours.

Further, the compound can also be synthesized by allowing the starting material to react with 1 to 100 equivalents of an ordinary saccharide donor represented by the following formula:

(L)

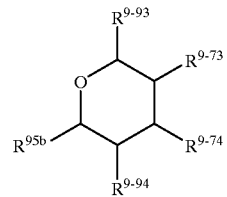

(in the formula, $R^{95b}$ represents halogen, a phenylthio group, an alkylthio group, a group represented by $CCl_3C(=NH)-O-$ or the like, $R^{9-93}$ has the same meaning as the above defined $R^{93}$, and $R^{9-73}$, $R^{9-74}$, and $R^{9-94}$ have the same meanings as the above defined $R^{73}$, $R^{74}$ and $R^{94}$, respectively) or the like in an inert solvent such as toluene, acetonitrile, tetrahydrofuran, ether, dichloromethane or 1,2-dichloroethane in the presence of 0.01 to 10 equivalents of an activating agent such as trimethylsilyl triflate, a trifluoroborane ether complex, silver perchlorate/tin chloride, silver carbonate, or methyl triflate. A drying agent such as molecular sieves may be used, if necessary. The reaction temperature is preferably −78° C. to 100° C., and the reaction time is usually 5 minutes to 150 hours.

Compounds having a substituent of formula (H), (J), or (K) can also be synthesized by repeating the above step 7. It is also possible to obtain a compound having a substituent of formula (G-2) by performing the process shown in the above step 7 using an ordinary saccharide donor represented by formula (L) wherein $R^{95}b$ has the same meaning as that defined above and $R^{9-94}$ is a substituted or unsubstituted lower alkanoyloxy group.

Isolation and purification of products obtained in the aforementioned preparation methods can be performed by a suitable combination of techniques used for ordinary organic synthesis such as filtration, extraction, washing, drying, concentration, and crystallization, as well as various kinds of chromatography techniques. Further, intermediate products can also be used in a subsequent reaction without particular purification. The compounds of the present invention represented by formula (Ia) may exist in the forms of salts, and examples thereof include those exemplified for the compounds represented by formula (I). For preparation of the salts of the compounds of formula (Ia), a compound of formula (Ia) in a free form is dissolved or suspended in a suitable solvent, a suitable acid or base is added thereto, and the produced salt can be isolated or purified, as required. If a desired salt is produced as a target product in a final step, it is also possible to isolate or purify the salt, per se. An appropriate salt can be converted into a compound in the free form, and then a suitable acid or base can be added to the free compound for conversion into a desired salt.

The compounds represented by formula (Ia) and salts thereof according to the present invention are useful as an active ingredient of medicaments such as agents for inducing apoptosis, antibacterial agents, anticancer agents, anti-Piroplasma agents, anti-parasitic agents, anti-inflammatory agents, hypolipidemic agents or the like. However, use of the compounds of the present invention is not limited to the aforementioned medicaments.

EXAMPLES

The present invention will be explained more specifically with reference to the following examples. However, the scope of the present invention is not limited to the following examples. The compound numbers in the examples correspond to the compound numbers specifically mentioned above.

Example 1

Compound 20

Compound 9 (54.4 mg, 0.0696 mmol) was dissolved in methylene chloride (2 ml), 4-dimethylaminopyridine (128.8 mg, 1.05 mmol), 1-ethyl-3-(3-dimethylamino-propyl) carbodiimide (99.0 mg, 0.517 mmol) and 2-[2-(2-methoxyethoxy)ethoxy]acetic acid (0.088 ml, 0.573 mmol) were added thereto, and then the mixture was stirred overnight. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) and $C_{18}$ column chromatography (70–100% methanol/water) to obtain Compound 20 (38.6 mg, 50%).
$^{13}$CNMR (125 MHz, $CDCl_3$) δ; 13.8, 14.4, 14.9, 16.0, 17.0, 21.9, 25.2, 30.0, 31.1, 31.3, 31.7, 36.0, 36.9, 41.2, 41.8, 43.1, 51.2, 52.7, 53.8, 54.1, 59.0, 59.1, 68.65, 68.68, 68.8, 70.5, 70.55, 70.61, 70.7, 71.0, 71.1, 71.9, 72.0, 72.7, 78.4, 78.6, 83.7, 90.7, 97.5, 100.9, 117.2, 123.6, 124.8, 126.6, 135.8, 137.5, 141.8, 144.4, 157.3, 166.2, 169.9, 170.1, 192.0, 201.0, 206.1
FAB-MS (m/z); 1101 (M−1)$^-$

Example 2

Compound 21

Compound 9 (53.2 mg, 0.0680 mmol) was dissolved in N,N-dimethylformamide (1 ml), triethylamine (0.0189 ml, 0.883 mmol) and tert-butyldimethylsilyl chloride (97.8 mg, 0.650 mmol) were added thereto, and then the mixture was stirred at room temperature for 6 days. Water was added to the reaction mixture, the mixture was extracted with chloroform, and the organic layer was washed with saturated brine and then dried over sodium sulfate. The solvent was evaporated under reduced pressure, and the residue was purified by silica gel column chromatography (chloroform) to obtain Compound 21.
$^{13}$CNMR (100 MHz, $CDCl_3$) δ; −4.9, −4.4, −4.3, −4.1, 13.3, 14.2, 15.1, 15.8, 17.0, 17.9, 18.3, 22.0, 25.4, 25.6 (3C), 26.0 (3C), 29.8, 31.2, 31.6, 35.5, 36.1, 39.4, 41.5, 42.9, 45.1, 51.3, 52.7, 53.6, 54.3, 68.6, 70.3, 76.8, 80.4, 84.2, 90.6, 99.1, 100.7, 118.9, 124.2, 124.9, 127.3, 135.1, 135.9, 140.8, 149.6, 157.3, 166.7, 192.6, 201.8, 206.7
FAB-MS (m/z); 1009 (M−1)$^-$

Example 3

Compound 22

Compound 21 (23.1 mg, 0.0229 mmol) was dissolved in tetrahydrofuran (1 ml), tetrabutylammonium fluoride (0.0458 ml, a 1 N solution in tetrahydrofuran, 0.0458 mmol) was added thereto, and then the mixture was stirred at room temperature overnight. Water was added to the reaction mixture, the mixture was extracted with chloroform, and the organic layer was washed with saturated brine and then dried over sodium sulfate. The solvent was evaporated under reduced pressure, and the residue was purified by silica gel column chromatography (0–2% methanol/chloroform) to obtain Compound 22 (13.2 mg, 64%).
$^{13}$CNMR (100 MHz, $CDCl_3$) δ; −4.8, −4.3, 13.3, 14.2, 15.2, 16.1, 17.0, 18.3, 22.1, 25.3, 26.0 (3C), 29.8, 30.7, 31.2, 35.5, 36.1, 39.5, 41.5, 43.0, 45.0, 51.4, 52.8, 53.8, 54.3, 69.3, 69.5, 76.8, 78.0, 84.0, 91.6, 96.5, 100.8, 118.3, 122.8, 124.8, 127.4, 136.4, 136.5, 141.5, 149.4, 157.3, 166.5, 192.4, 201.7, 206.8
FAB-MS (m/z); 895 (M−1)$^-$

Example 4

Compound 23

Compound 9 (23.0 mg, 0.0294 mmol) was dissolved in N,N-dimethylformamide (1 ml), triethylamine (0.0164 ml, 0.118 mmol) and tert-butyldimethylsilyl chloride (20.4 mg, 0.136 mmol) were added thereto, and then the mixture was stirred at room temperature for two days. Water was added to the reaction mixture, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 23 (20.3 mg, 77%).
$^{13}$CNMR (100 MHz, $CDCl_3$) δ; −4.3, −4.0, 13.0, 14.4, 15.1, 15.9, 17.0, 17.9, 22.0, 25.5, 25.7 (3C), 29.8, 31.1, 31.7, 34.8, 36.1, 39.3, 41.6, 43.0, 45.2, 51.3, 52.7, 53.7, 54.4, 68.6, 70.3, 76.0, 80.3, 84.2, 90.6, 99.1, 100.9, 118.9, 124.4, 125.8, 126.2, 135.1, 135.9, 140.8, 149.6, 157.3, 166.8, 192.6, 201.7, 206.6
FAB-MS (m/z); 895 (M−1)$^-$

Example 5

Compounds 24, 25 and 26

Compound 1 (33.5 mg, 0.0255mmol) was dissolved in ethanol (1 ml), pyridine (0.005 ml, 0.06mmol) and hydroxylamine (2.3 mg, 0.033 mmol) were added thereto, and the mixture was stirred at 80° C. for 12 hours. The solvent was evaporated under reduced pressure, and the residue was purified by preparative thin layer chromatography (5% methanol/chloroform) to obtain Compound 24 (5.0 mg, 16%), Compound 25 (0.7 mg, 3%) and Compound 26 (4.5 mg, 18%).
Compound 24
$^{13}$CNMR (100 MHz, $CDCl_3$) δ; 14.0, 14.3, 15.1, 16.1, 17.0, 17.6, 18.1, 18.2, 21.0, 22.0, 25.3, 26.3, 29.6, 30.8, 31.2, 31.5, 31.6, 34.6, 36.0, 38.1, 38.5, 41.6, 43.3, 45.0, 51.2, 52.8, 53.8, 54.2, 62.2, 66.7, 67.9, 68.3, 69.2, 69.3, 69.4, 73.1, 74.5, 78.1, 81.3, 84.37, 84.44, 91.5, 92.6, 96.6, 98.6, 99.2, 101.0, 118.8, 123.0, 126.1, 126.3, 129.0, 136.06, 136.10, 141.0, 151.4, 157.3, 166.8, 170.5, 201.7, 206.4
FAB-MS (m/z); 1212 (M−1)⁻
Compound 25
$^{13}$CNMR (100 MHz, CDCl$_3$) δ; 14.1, 14.3, 15.1, 16.1, 17.0, 17.6, 17.9, 21.0, 22.0, 25.3, 27.5, 29.6, 30.8, 31.2, 31.3, 31.5, 34.6, 36.0, 38.5, 41.6, 43.3, 45.0, 51.2, 52.8, 53.8, 54.2, 62.3, 66.5, 69.3, 69.4, 69.6, 72.2, 74.5, 78.0, 84.4 (2C), 91.5, 92.4, 96.5, 98.5, 101.0, 118.8, 123.1, 126.1, 126.2, 129.0, 136.00, 136.05, 141.0, 151.3, 157.3, 166.8, 170.3, 201.7, 206.4
FAB-MS (m/z); 1082 (M−1)⁻
Compound 26
$^{13}$CNMR (100 MHz, CDCl$_3$) δ; 14.4, 14.5, 15.0, 16.1, 17.0, 17.5, 21.2, 21.9, 25.3, 30.8, 31.2, 31.5, 34.3, 35.5, 36.0, 38.4, 41.7, 43.4, 45.0, 51.2, 52.8, 53.8, 54.1, 62.1, 65.6, 69.3, 69.4, 75.2, 78.0, 84.4, 85.7, 91.5, 96.6, 99.8, 101.1, 118.8, 123.3, 125.4, 126.8, 128.9, 135.8, 136.1, 141.0, 151.3, 157.3, 166.8, 170.5, 201.6, 206.2
FAB-MS (m/z); 968 (M−1)⁻

Example 6

Compound 27

Compound 1 (107.3 mg, 0.818 mmol) was dissolved in methanol (2 ml), 5.1 N sodium methoxide (0.05 ml, 0.255 mmol) was added thereto, and then the mixture was stirred for 4 hours. 0.1 N Hydrochloric acid was added to the reaction mixture, the mixture was extracted with chloroform, and the organic layer was washed with saturated brine and then dried over sodium sulfate. The solvent was evaporated under reduced pressure, and the residue was purified by silica gel column chromatography (3–10% methanol/chloroform) to obtain Compound 27 (71.5 mg, 69%).
$^{13}$CNMR (100 MHz, CDCl$_3$) δ; 14.1, 14.3, 15.1, 16.1, 17.0, 17.7, 17.8, 18.2, 18.9, 22.0, 25.3, 26.5, 27.4, 29.4, 29.75, 29.80, 30.7, 31.2, 31.4, 34.5, 36.3, 37.0, 38.5, 41.6, 43.3, 44.9, 51.2, 52.8, 53.8, 54.3, 63.9, 65.1, 67.8, 68.7, 69.28, 69.34, 69.5, 70.3, 71.8, 72.5, 75.3, 77.9, 80.8, 84.0, 84.2, 91.6, 92.0, 92.7, 96.5, 98.2, 99.2, 100.8, 118.2, 123.0, 125.9, 126.4, 136.2, 136.4, 141.5, 149.4, 157.4, 166.6, 192.4, 201.6, 206.5
FAB-MS (m/z); 1269 (M−1)⁻

Example 7

Compound 28

Compound 35 (described later, 28.4 mg, 0.0180 mmol) was dissolved in tetrahydrofuran (1 ml), tetrabutylammonium fluoride (0.180 ml, a 1 N solution in tetrahydrofuran, 0.180 mmol) was added thereto, and then the mixture was stirred overnight at room temperature. Water was added to the reaction mixture, the mixture was extracted with chloroform, and the organic layer was washed with saturated brine and then dried over sodium sulfate. The solvent was evaporated under reduced pressure, and the residue was purified by preparative thin layer chromatography (7.5% methanol/chloroform) to obtain Compound 28 (9.5 mg, 39%).
$^{13}$CNMR (100 MHz, CDCl$_3$) δ; 14.0, 14.4, 15.1, 16.1, 17.0, 17.6, 17.8, 18.1, 19.0, 21.0, 21.1, 22.0, 25.4, 26.4, 27.5, 29.1, 29.6, 29.8, 30.8, 31.2, 31.5, 34.6, 36.0, 36.2, 38.5, 41.6, 43.3, 44.9, 51.3, 52.8, 53.8, 54.3, 62.2, 65.7, 66.7, 67.8, 69.0, 69.3, 69.5, 70.1, 72.0, 73.3, 74.5, 78.0, 81.4, 84.0, 84.3, 91.6, 92.2, 92.6, 96.5, 98.5, 99.5, 100.8, 118.3, 123.0, 126.0, 126.4, 136.2, 136.5, 141.6, 149.4, 157.3, 166.6, 170.1, 170.4, 192.4, 201.5, 206.5
FAB-MS (m/z); 1353 (M−1)⁻

Example 8

Compound 29

Compound 1 (121.8 mg, 0.0928 mmol) was dissolved in methanol/acetonitrile (1/9, 4 ml), diisopropylethylamine (0.0226 ml, 0.130 mmol) and trimethylsilyldiazomethane (a 2.0 M solution in hexane, 0.065 ml, 0.130 mmol) were added thereto, and then the mixture was stirred at room temperature for 4.5 hours. The solvent was evaporated under reduced pressure, and the residue was purified by silica gel column chromatography (2–3% methanol/chloroform) to obtain Compound 29 (85.5 mg, 70%).
$^{13}$CNMR (100 MHz, CDCl$_3$) δ; 14.1, 14.5, 14.9, 15.3, 17.0, 17.5, 17.7, 18.1, 18.9, 21.0, 24.4, 25.4, 26.3, 27.4, 29.6, 29.7, 30.0, 30.9, 31.4, 31.5, 34.5, 36.0, 37.0, 38.9, 41.6, 44.6, 45.2, 50.9, 52.8, 53.8, 54.1, 62.1, 63.9, 64.4, 66.7, 67.8, 67.9, 69.1, 70.3, 70.4, 71.7, 74.5, 75.3, 78.7, 81.3, 83.8, 84.6, 91.5, 91.9, 92.6, 96.9, 98.5, 99.3, 107.8, 119.1, 121.4, 125.9, 126.6, 136.5, 138.9, 141.7, 149.2, 157.3, 168.7, 170.4, 188.8, 192.5, 198.6
FAB-MS (m/z); 1327 (M+1)⁺

Example 9

Compound 30

Compound 2 (29.4 mg, 0.0204 mmol) was dissolved in methanol/acetonitrile (1/9, 1 ml), diisopropylethylamine (0.005 ml, 0.057mmol) and trimethylsilyldiazo-methane (a 2.0 M solution in hexane, 0.0286 ml, 0.057 mmol) were added thereto, and then the mixture was stirred at room temperature for 4.5 hours. The solvent was evaporated under reduced pressure, and the residue was purified by silica gel column chromatography (2.5% methanol/chloroform) to obtain Compound 30 (15.3 mg, 51%).
$^{13}$CNMR (100 MHz, CDCl$_3$) δ; 14.1, 14.6, 14.8, 15.2, 17.1, 17.6, 17.8, 18.1, 19.0, 20.97, 21.01, 21.1, 21.2, 24.1, 24.5, 25.3, 26.4, 28.6, 29.6, 30.2, 31.4, 31.6 (2C), 34.5, 36.0, 36.1, 38.8, 41.6, 42.3, 44.6, 50.9, 52.7, 53.8, 54.0, 62.1, 64.4, 65.6, 66.8, 67.2, 67.8, 68.6, 68.9, 72.6, 73.4, 73.5, 74.5, 80.3, 81.4, 83.6, 84.6, 90.8, 92.4, 92.6, 98.5, 98.7, 99.5, 108.0, 118.4, 122.1, 125.9, 126.7, 137.4, 138.8, 141.6, 145.2, 157.3, 168.4, 170.1, 170.2, 170.4 (2C), 188.2, 192.2, 198.6
FAB-MS (m/z); 1451 (M−1)⁻, 1452 (M)⁻

Example 10

Compounds 31, 32 and 33

Compound 1 (202.9 mg, 0.155 mmol) was dissolved in N,N-dimethylformamide (4 ml), triethylamine (0.108 ml, 0.776 mmol) and tert-butyldimethylsilyl chloride (111.7 mg, 0.742 mmol) were added thereto, and then the mixture was stirred at room temperature for 6.5 hours. Water was added to the reaction mixture, the mixture was extracted with chloroform, and the organic layer was washed with saturated brine and then dried over sodium sulfate. The solvent was evaporated under reduced pressure, and the residue was purified by silica gel column chromatography (1–10% methanol/chloroform) to obtain Compound 31 (58.1 mg, 26%), Compound 32 (12.2 mg, 6%), and Compound 33 (136.2 mg, 57%).

53

Compound 31
¹³CNMR (100 MHz, CDCl₃) δ; −4.7, −4.1, 14.0, 14.3, 15.0, 16.1, 16.9, 17.5, 18.0, 18.08, 18.13, 18.8, 21.0, 22.0, 25.3, 25.8 (3C), 26.3, 28.1, 29.6, 29.8 (2C), 30.7, 31.1, 31.5, 34.6, 36.0, 37.0, 38.4, 41.6, 43.2, 44.9, 51.2, 52.8, 53.7, 54.2, 62.1, 64.0, 66.6, 67.9, 67.9, 69.3, 69.4, 70.6, 72.5, 74.4, 75.4, 76.7, 81.3, 84.0, 84.3, 91.5, 92.2, 92.6, 96.4, 98.5, 99.3, 100.8, 118.2, 122.9, 125.9, 126.4, 136.1, 136.4, 141.5, 149.4, 157.2, 166.6, 170.5, 192.4, 201.5, 206.5
FAB-MS (m/z); 1425 (M−1)⁻

Compound 32
¹³CNMR (125 MHz, CDCl₃) δ; −4.3, −4.0, 14.0, 14.4, 15.1, 15.9, 17.0, 17.6, 17.8, 17.9, 18.1, 18.9, 21.0, 22.0, 25.5, 25.6 (3C), 26.4, 27.5, 29.6, 29.8 (2C), 31.2, 31.5, 31.7, 34.6, 36.1, 37.0, 38.4, 41.6, 43.3, 45.1, 51.2, 52.7, 53.7, 54.4, 62.1, 63.9, 66.6, 67.8, 67.9, 68.6, 70.30, 70.34, 71.8, 74.5, 75.3, 80.3, 81.3, 84.2, 84.4, 90.6, 91.9, 92.6, 98.5, 99.0, 99.3, 100.8, 118.9, 124.4, 126.2 (2C), 134.9, 135.9, 140.8, 149.6, 157.3, 166.8, 170.5, 192.6, 201.7, 206.5
FAB-MS (m/z); 1425 (M−1)⁻

Compound 33
¹³CNMR (100 MHz, CDCl₃) δ; −4.7, −4.4, −4.10, −4.09, 14.0, 14.3, 15.0, 15.8, 16.9, 17.5, 17.86, 17.95, 18.0, 18.1, 18.8, 21.0, 21.9, 25.4, 25.6 (3C), 25.8 (3C), 26.3, 28.1, 29.6, 29.7 (2C), 31.1, 31.5, 31.6, 34.5, 36.0, 37.0, 38.4, 41.6, 43.2, 45.1, 51.1, 52.7, 53.6, 54.3, 62.1, 64.0, 66.6, 67.8, 67.9, 68.6, 70.3, 70.6, 72.5, 74.4, 75.4, 80.3, 81.2, 84.2, 84.3, 90.6, 92.2, 92.5, 98.5, 99.0, 99.2, 100.8, 118.9, 124.4, 126.1, 126.2, 134.8, 135.8, 140.7, 149.5, 157.2, 166.7, 170.4, 192.5, 201.6, 206.4
FAB-MS (m/z); 1539 (M−1)⁻

Example 11

Compound 34

Compound 1 (109.9 mg, 0.0838 mmol) was dissolved in N,N-dimethylformamide (2 ml), triethylamine (0.300 ml, 2.16 mmol) and tert-butyldimethylsilyl chloride (631.4 mg, 4.20 mmol) were added thereto, and then the mixture was stirred overnight at room temperature. Water was added to the reaction mixture, the mixture was extracted with chloroform, and the organic layer was washed with saturated brine and then dried over sodium sulfate. The solvent was evaporated under reduced pressure, and the residue was purified by silica gel column chromatography (1–2% methanol/chloroform) to obtain Compound 33 (83.1 mg, 64%) and Compound 34 (22.9 mg, 17%).
¹³CNMR (125 MHz, CDCl₃) δ; −4.8, −4.6, −4.4, −4.3, −4.1, −4.0, 14.0, 14.3, 15.1, 15.9, 17.0, 17.6, 17.9, 17.96, 18.0, 18.1, 18.2, 18.8, 21.0, 22.0, 25.5, 25.6 (3C), 25.7 (3C), 25.8 (3C), 26.4, 28.2, 29.4, 29.7, 29.8, 31.1, 31.5, 31.6, 34.6, 36.1, 38.4, 39.3, 41.6, 43.3, 45.1, 51.2, 52.7, 53.6, 54.4, 62.1, 64.3, 66.6, 68.0, 68.5, 68.6, 70.1, 70.3, 72.8, 74.4, 74.9, 80.3, 81.3, 84.2, 84.4, 90.6, 91.4, 92.6, 98.5, 99.0, 99.7, 100.8, 118.9, 124.4, 126.1, 126.2, 134.9, 135.9, 140.8, 149.6, 157.3, 166.8, 170.5, 192.6, 201.7, 206.5
FAB-MS (m/z); 1653 (M−1)⁻, 1654 (M)⁻

Example 12

Compound 35

Compound 33 (28.7 mg, 0.0186 mmol) was dissolved in pyridine (0.3 ml), acetic anhydride (0.05 ml) was added thereto, and then the mixture was stirred at room temperature for five days. The solvent was evaporated under reduced pressure, and the residue was purified by silica gel column chromatography (0–1% methanol/chloroform) to obtain Compound 35 (24.1 mg, 82%).

54

¹³CNMR (100 MHz, CDCl₃) δ; −4.6, −4.3, −4.0 (2C), 14.0, 14.4, 15.1, 15.9, 17.0, 17.6, 17.9, 18.0, 18.1, 18.2, 19.0, 21.0, 21.1, 22.0, 25.5, 25.6 (3C), 25.8 (3C), 26.3, 28.2, 29.1, 29.6, 29.8, 31.2, 31.5, 31.6, 34.6, 36.1 (2C), 38.4, 41.6, 43.3, 45.1, 51.2, 52.7, 53.7, 54.4, 62.1, 65.8, 66.7, 67.8, 68.6, 69.1, 70.3, 70.4, 72.7, 73.4, 74.5, 80.3, 81.3, 84.2, 84.4, 90.6, 92.48, 92.54, 98.5, 99.0, 99.5, 100.9, 118.9, 124.4, 126.2 (2C), 134.9, 135.9, 140.8, 149.6, 157.3, 166.8, 170.1, 170.4, 192.6, 201.7, 206.5
FAB-MS (m/z); 1581 (M−1)⁻

Example 13

Compound 36

Compound 33 (30.7 mg, 0.0199 mmol) was dissolved in methanol (1 ml), 5.1 N sodium methoxide (0.02 ml, 0.102 mmol) was added thereto, and then the mixture was stirred for 4 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (2.5% methanol/chloroform) to obtain Compound 36 (21.7 mg, 73%).
¹³CNMR (100 MHz, CDCl₃) δ; −4.6, −4.3, −4.0 (2C), 14.1, 14.3, 15.1, 15.9, 17.0, 17.87, 17.92, 18.0, 18.16, 18.20, 18.8, 22.0, 25.5, 25.6 (3C), 25.8 (3C), 26.4, 28.1, 29.3, 29.8 (2C), 31.15, 31.25, 31.6, 34.5, 36.1, 37.0, 38.4, 41.6, 43.3, 45.1, 51.2, 52.7, 53.6, 54.4, 64.1, 65.1, 67.9, 68.6, 68.7, 69.1, 70.3, 70.6, 72.5, 72.7, 75.5, 80.3, 80.7, 84.2 (2C), 90.6, 92.3, 92.6, 98.2, 99.1, 99.2, 100.8, 118.9, 124.4, 126.2 (2C), 134.9, 135.9, 140.8, 149.6, 157.3, 166.8, 192.6, 201.7, 206.5
FAB-MS (m/z); 1497 (M−1)⁻

Example 14

Compound 37

Compound 1 (98.4 mg, 0.075 mmol) was dissolved in chloroform (5 ml), methyltriphenylphosphoranilidene acetate (140.7 mg, 0.421 mmol) was added thereto, and then the mixture was refluxed by heating for 2 hours. The solvent was evaporated under reduced pressure, and the residue was triturated with ether. The resulting product was purified by silica gel column chromatography (2–3% methanol/chloroform) to obtain Compound 37 (22.8 mg, 22%).
¹³CNMR (100 MHz, CDCl₃) δ; 14.0, 14.3, 15.1, 16.1, 17.0, 17.5, 17.7, 18.1, 18.9, 21.0, 22.1, 25.3, 26.4, 27.4, 29.6, 29.7, 30.8, 31.2, 31.6, 32.2, 34.6, 36.0, 37.0, 38.5, 41.6, 43.3, 44.9, 51.3, 51.7, 52.8, 53.8, 54.2, 62.2, 62.6, 63.9, 66.7, 67.8, 67.9, 69.2, 69.5, 70.3, 71.7, 74.5, 75.3, 78.0, 81.3, 84.3, 84.4, 91.4, 91.9, 92.6, 96.5, 98.5, 99.3, 100.8, 118.0, 118.7, 123.1, 126.1, 126.3, 130.5, 136.0, 138.7, 141.1, 145.1, 157.3, 167.1, 170.4, 201.7, 206.3
FAB-MS (m/z); 1367 (M−1)⁻

Example 15

Compound 38

Compound 29 (28.8 mg, 0.0217 mmol) was dissolved in ethanol (2 ml) and the solution was refluxed by heating for two days with stirring. The solvent was evaporated under reduced pressure, and the residue was purified by preparative thin layer chromatography (5% methanol/chloroform) to obtain Compound 38 (13.7 mg, 45%).
¹³CNMR (100 MHz, CDCl₃) δ; 14.1, 14.6, 14.9, 15.18, 15.21, 15.3, 17.0, 17.6, 17.7, 18.1, 18.9, 21.0, 24.3, 25.4, 26.4, 27.5, 29.6, 29.8, 30.9, 31.3, 31.5, 31.6, 34.6, 36.0, 37.1, 38.9, 41.7, 44.7, 45.3, 50.9, 52.8, 53.8, 54.1, 61.9, 62.1 (2C), 64.0, 64.1, 66.8, 67.8, 67.9, 69.0, 70.30, 70.34, 71.8, 74.5, 75.3, 78.8, 81.4, 84.6, 84.8, 91.3, 91.9, 92.6, 97.0, 98.5, 99.3, 103.1, 107.7, 120.1, 121.6, 125.9, 126.8, 127.8, 132.4, 138.7, 140.7, 157.3, 169.1, 170.4, 189.7, 198.7
FAB-MS (m/z); 1400 (M)⁻

Example 16

Compound 39

Compound 33 (74.3 mg, 0.0482 mmol) was dissolved in a dichloromethane (2 ml), 1,8-bis(dimethylamino) naphthalene (55.9 mg, 0.261 mmol) and trimethyl tetrafluoroborate (39.8 mg, 0.269 mmol) were added thereto, and then the mixture was stirred at room temperature for 11 hours. Water was added thereto, the mixture was extracted with chloroform, and the organic layer was washed with saturated brine and then dried over sodium sulfate. Then, the solvent was evaporated under reduced pressure, and the residue was purified by preparative thin layer chromatography (5% methanol/chloroform) to obtain Compound 39 (36.4 mg, 48%).
$^{13}$CNMR (100 MHz, CDCl$_3$) δ; −4.6, −4.3, −4.2, −4.0, 14.1, 14.3, 14.7, 15.5, 17.1, 17.5, 17.9, 18.0, 18.1, 18.2, 18.9, 21.0, 24.4, 25.2, 25.7 (3C), 25.8 (3C), 26.3, 28.2, 29.5, 29.6, 29.7, 31.4, 31.5, 31.7, 34.4, 34.5, 35.9, 38.8, 41.6, 44.6, 45.6, 50.7, 52.7, 53.6, 53.7, 57.5, 62.1, 64.2, 66.7, 67.9, 68.8, 68.9, 70.3, 70.6, 72.7, 72.8, 74.6, 74.7, 81.2, 82.0, 84.0, 84.7, 90.7, 91.6, 92.6, 98.5, 99.4, 100.5, 107.5, 120.3, 123.4, 125.9, 126.6, 136.2, 138.7, 140.6, 149.8, 157.3, 168.9, 170.4, 189.5, 192.7, 198.3
FAB-MS (m/z); 1567 (M−1)⁻

Example 17

Compounds 40 and 41

Compound 1 (49.2 mg, 0.0375 mmol) was dissolved in dichloromethane (1 ml), N,N-diisopropylethylamine (0.117 ml, 0.675 mmol) and the chloromethyl methyl ether (0.0340 ml, 0.448 mmol) were added thereto, and then the mixture was stirred overnight at room temperature. Water was added thereto, the mixture was extracted with chloroform, and the organic layer was washed with saturated brine and then dried over sodium sulfate. Then, the solvent was evaporated under reduced pressure, and the residue was purified by preparative thin layer chromatography (5% methanol/chloroform) to obtain Compound 40 (16.6 mg, 33%) and Compound 41 (5.5 mg, 10%).
Compound 40
$^{13}$CNMR (125 MHz, CDCl$_3$) δ; 14.0, 14.4, 15.1, 16.1, 17.0, 17.5, 18.06, 18.11, 18.9, 21.0, 22.0, 24.6, 25.3, 26.4, 29.4, 29.6, 29.8, 30.7, 31.2, 31.6, 34.6, 36.0, 37.0, 38.5, 41.6, 43.3, 44.9, 51.2, 52.8, 53.8, 54.3, 55.6, 62.2, 63.9, 66.7, 67.8, 67.9, 68.7, 69.3, 69.5, 74.4, 75.2, 76.7, 78.0, 81.3, 84.0, 84.3, 91.6, 91.9, 92.6, 95.2, 96.5, 98.6, 99.4, 100.8, 118.2, 122.9, 126.0, 126.4, 136.2, 136.5, 141.6, 149.4, 157.3, 166.6, 170.5, 192.4, 201.6, 206.5
FAB-MS (m/z); 1355 (M−1)⁻
Compound 41
FAB-MS (m/z); 1399 (M−1)⁻

Example 18

Compounds 42, 43 and 44

Compound 1 (44.7 mg, 0.0341 mmol) was dissolved in dichloromethane (1 ml), N,N-diisopropylethylamine (0.119 ml, 0.681 mmol) and chloromethyl n-octyl ether (0.0659 ml, 0.444 mmol) were added thereto, and then the mixture was stirred at room temperature for 6.5 hours. Water was added thereto, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 42 (8.0 mg, 15%), Compound 43 (39.2 mg, 66%) and Compound 44 (5.8 mg, 11%).
Compound 42
$^{13}$CNMR (100 MHz, CDCl$_3$) δ; 14.0, 14.1 (2C), 14.4, 15.1, 16.1, 17.0, 17.6, 18.05, 18.14, 19.0, 21.0, 22.0, 22.7 (2C), 24.6, 25.4, 26.2, 26.3, 26.4, 29.1, 29.3 (2C), 29.46, 29.50, 29.6, 29.7 (2C), 29.8, 30.8, 31.2, 31.6, 31.9 (2C), 34.6, 36.1, 36.3, 38.5, 41.6, 43.3, 45.0, 51.3, 52.8, 53.8, 54.3, 62.2, 66.7, 67.9, 68.3, 68.49, 68.54, 68.8, 68.9, 69.3, 69.5, 74.4, 74.5, 77.2, 77.9, 81.4, 84.0, 84.4, 91.4, 91.6, 92.6, 93.8, 94.8, 96.5, 98.6, 99.8, 100.8, 118.3, 123.0, 126.0, 126.4, 136.2, 136.5, 141.6, 149.4, 157.3, 166.6, 170.4, 192.4, 201.6, 206.5
FAB-MS (m/z); 1595 (M−1)⁻
Compound 43
$^{13}$CNMR (100 MHz, CDCl$_3$) δ; 14.0, 14.1 (3C), 14.4, 15.1, 16.2, 17.0, 17.5, 18.0, 18.1, 19.0, 21.0, 22.0, 22.7 (3C), 24.6, 25.4, 26.20, 26.22, 26.27, 26.33, 29.1, 29.26, 29.28, 29.29, 29.42, 29.45, 29.48, 29.60, 29.69, 29.74, 29.8, 31.1, 31.4, 31.5, 31.78, 31.84, 31.90, 31.92, 34.6, 36.2, 36.3, 38.4, 41.6, 43.3, 51.2, 52.7, 53.8, 54.3, 62.2, 66.7, 67.9, 68.3, 68.47, 68.53, 68.7, 68.8, 68.9, 74.4, 74.5, 76.7, 77.3, 77.6, 77.8, 81.3, 84.2, 84.4, 90.7, 91.4, 92.4, 92.6, 93.8, 95.3, 96.9, 97.7, 98.5, 99.7, 100.9, 118.3, 123.5, 126.0, 126.4, 135.8, 136.2, 140.6, 149.0, 157.3, 166.6, 170.4, 192.5, 201.6, 206.5
FAB-MS (m/z); 1737 (M−1)⁻
Compound 44
$^{13}$CNMR (100 MHz, CDCl$_3$) δ; 14.0, 14.1 (2C), 14.4, 15.1, 16.2, 17.0, 17.6, 18.08, 18.11, 18.9, 21.0, 22.0, 22.7 (2C), 24.6, 25.4, 26.27, 26.35 (2C), 29.28, 29.31, 29.4, 29.46, 29.49, 29.6, 29.7, 29.8 (2C), 31.2, 31.4, 31.6, 31.9 (2C), 34.6, 36.2, 37.0, 38.4, 41.5, 43.3 (2C), 51.2, 52.4, 53.8, 54.3, 62.2, 64.0, 66.7, 67.8, 67.9, 68.4, 68.7, 68.8, 74.5, 75.2, 76.6, 77.6, 77.9, 81.3, 84.2, 84.4, 90.7, 91.4, 92.0, 92.6, 93.9, 96.9, 97.7, 98.6, 99.4, 100.9, 118.3, 123.4, 126.0, 126.4, 135.8, 136.2, 140.6, 149.0, 157.3, 170.5, 192.5, 201.6, 206.5, 216.1
FAB-MS (m/z); 1595 (M−1)⁻

Example 19

Compound 45

Compound 1 (20.0 mg, 0.0152 mmol) was dissolved in methanol (2 ml) and the solution was left to stand at room temperature for four days. The solvent was evaporated under reduced pressure to obtain Compound 45 (20.7 mg, 100%).
$^{13}$CNMR (125 MHz, CDCl$_3$) δ; 14.0, 14.3, 15.0, 16.1, 17.0, 17.5, 17.7, 18.1, 18.9, 21.0, 21.9, 25.3, 26.3, 27.4, 29.6, 29.7, 30.8, 31.1, 31.2, 31.5, 34.6, 36.0, 37.0, 38.5, 41.6, 43.2, 45.0, 51.2, 52.8, 53.6, 53.8, 53.8, 54.1, 62.1, 63.9, 66.7, 67.8, 67.9, 69.2, 69.3, 70.3, 71.7, 74.4, 75.2, 78.0, 81.3, 84.4, 84.9, 91.4, 91.9, 92.6, 96.5, 98.5, 99.3, 101.0, 104.8, 119.1, 123.0, 126.1, 126.3, 128.9, 131.4, 136.0, 140.5, 157.3, 167.0, 170.4, 201.8, 206.4
FAB-MS (m/z); 1357 (M−1)⁻

Example 20

Compound 46

Compound 23 (63.1 mg, 0.0704 mmol) was dissolved in dichloromethane (3 ml), 4-dimethylaminopyridine (38.1 mg, 0.312 mmol), 1-ethyl-3-(3-dimethylaminopropyl) carbodiimide (31.5 mg, 0.164 mmol) and 2-[2-(2-methoxyethoxy)ethoxy]acetic acid (0.0227 ml, 0.148 mmol) were added thereto, and then the mixture was stirred for 1.5 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (3% methanol/chloroform) to obtain Compound 46 (34.4 mg, 46%).
$^{13}$CNMR (100 MHz, CDCl$_3$) δ; −4.4, −4.1, 13.8, 14.3, 14.9, 15.8, 17.0, 17.9, 21.9, 25.5, 25.6 (3C), 29.7, 31.0, 31.6, 31.7, 36.1, 36.8, 41.2, 43.1, 45.1, 51.2, 52.7, 53.6, 54.2, 59.1, 68.6 (2C), 70.3, 70.55, 70.63, 71.0, 71.9, 78.7, 80.3, 84.2, 90.6, 99.0, 101.0, 118.8, 124.6 (2C), 126.9, 134.8, 135.8, 140.8, 149.5, 157.3, 166.7, 170.0, 192.6, 201.4, 206.0
FAB-MS (m/z); 1055 (M−1)$^-$

Example 21

Compound 47

Compound 46 (30.5 mg, 0.0289 mmol) was dissolved in tetrahydrofuran (1 ml), tetrabutylammonium fluoride (0.130 ml, a 1 N solution in tetrahydrofuran, 0.130 mmol) was added thereto, and then the mixture was stirred at room temperature for 25 minutes. Water was added thereto, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 47 (25.0 mg, 92%).
$^{13}$CNMR (100 MHz, CDCl$_3$) δ; 13.7, 14.4, 15.0, 16.1, 17.0, 22.1, 25.3, 30.0, 30.8, 31.3, 31.8, 36.0, 37.2, 41.5, 43.3, 45.0, 51.3, 52.8, 53.6, 53.8, 59.1, 68.6, 69.2, 69.7, 70.6 (2C), 71.0, 71.9, 78.0, 78.9, 83.8, 96.5, 99.2, 101.0, 118.8, 122.5, 124.5, 127.3, 136.2, 136.8, 140.8, 149.5, 157.3, 168.1, 170.0, 192.6, 200.7, 204.4
FAB-MS (m/z); 941 (M−1)$^-$

Example 22

Compound 48

Compound 1 (49.3 mg, 0.0375 mmol) was dissolved in dichloromethane (1 ml), 1,2-ethanedithiol (0.0095 ml, 0.11 mmol) and a trifluoroborane diethyl ether complex (0.0069 ml, 0.056 mmol) were added thereto, and then the mixture was stirred at room temperature for 40 minutes. Hexane was added to the system, and the precipitate was collected by filtration, and purified by preparative thin layer chromatography (5% methanol/chloroform) to obtain Compound 48 (9.9 mg, 31%).
$^{13}$CNMR (100 MHz, CDCl$_3$) δ; 13.0, 14.3, 15.0, 16.1, 17.0, 22.2, 25.3, 30.8, 31.2, 31.4, 34.8, 36.0, 39.4, 39.9, 40.0, 41.7, 42.9, 45.2, 51.4, 52.8, 53.8, 54.1, 57.5, 69.2, 69.7, 76.0, 78.1, 85.1, 91.4, 96.5, 101.2, 119.0, 123.1, 125.9, 126.1, 128.1, 133.2, 136.1, 140.7, 157.3, 166.9, 201.8, 206.5
FAB-MS (m/z); 857 (M−1)$^-$

Example 23

Compound 49

Compound 10 (42.6 mg, 0.0517 mmol) and 4-methoxybenzyl trichloroacetimidate (126.8 mg, 0.449 mmol) were dissolved in dichloromethane (2 ml), trifluoromethanesulfonic acid (0.0005 ml, 0.00 5 mmol) was added thereto, and then the mixture was stirred at room temperature for 3 hours. Saturated aqueous sodium hydrogencarbonate was added to the reaction solution, and the mixture was extracted with chloroform. The organic layer was washed with saturated brine and then dried over sodium sulfate. The solvent was evaporated under reduced pressure and the residue was purified by preparative thin layer chromatography (3% methanol/chloroform) to obtain Compound 49 (26.5 mg, 54%).
$^{13}$CNMR (100 MHz, CDCl$_3$) δ; 13.4, 14.4, 15.0, 16.0, 17.1, 20.9, 22.0, 25.2, 30.1, 30.8, 31.2, 31.5, 36.0, 38.3, 41.4, 41.9, 43.1, 51.4, 52.7, 53.8, 54.3, 55.3, 68.7, 70.3, 71.9, 78.8, 82.6, 83.8, 90.7, 97.8, 100.8, 113.8 (2C), 117.5, 123.3, 125.1, 126.8, 129.1 (2C), 131.0, 136.1, 137.3, 141.4, 145.3, 157.3, 159.1, 166.2, 170.4, 192.1, 201.4, 206.7
FAB-MS (m/z); 943 (M−1)$^-$

Example 24

Compound 50

Compound 51 (described later, 10.7 mg, 0.0118 mmol) was dissolved in methanol/dichloromethane (1/1, 2 ml), 5.1 N sodium methoxide (0.010 ml, 0.51 mmol) was added thereto, and then the mixture was stirred for 4 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 50 (3.9 mg, 38%).
FAB-MS(m/z); 865 (M−1)$^-$

Example 25

Compound 51

Compound 10 (50.0 mg, 0.0607 mmol) was dissolved in dichloromethane (1 ml), 3,4-dihydro-2H-pyran (0.0066 ml, 0.0723 mmol) and p-toluenesulfonic acid monohydrate (0.6 mg, 0.003 mmol) were added thereto, and then the mixture was stirred overnight at room temperature. Saturated aqueous sodium hydrogen-carbonate was added thereto, and the mixture was extracted with chloroform. The organic layer was washed with saturated brine and then dried over sodium sulfate. The solvent was evaporated under reduced pressure and the residue was purified by preparative thin layer chromatography (5% methanol/chloroform) to obtain Compound 51 (31.9 mg, 58%).
FAB-MS(m/z); 907(M−1)$^-$

Example 26

Compound 52

Compound 59 (described later, 31.2 mg, 0.0301 mmol) was dissolved in methanol/dichloromethane (1/1, 2 ml), 5.1 N sodium methoxide (0.030 ml, 0.153 mmol) was added thereto, and the mixture was stirred for 3 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 52 (9.2 mg, 34%).
$^{13}$CNMR (125 MHz, CDCl$_3$) δ; 13.9, 14.4, 15.0, 16.1, 17.0, 17.7, 22.0, 25.3, 29.8, 30.8, 31.2, 34.4, 36.0, 37.8, 38.5, 41.6, 43.3, 44.9, 51.3, 52.8, 53.8, 54.2, 68.4, 69.3, 69.5 (2C), 78.0, 78.2, 83.9, 84.0, 91.6, 96.5, 99.6, 100.9, 118.3, 123.0, 126.0, 126.2, 136.1, 136.4, 141.5, 149.4, 157.3, 166.6, 192.4, 201.5, 206.5
FAB-MS (m/z); 911 (M−1)⁻

Example 27

Compound 53

Compound 58 (described later, 34.7 mg, 0.0317 mmol) was dissolved in methanol/dichloromethane (1/1, 2 ml), 5.1 N sodium methoxide (0.030 ml, 0.153 mmol) was added thereto, and then the mixture was stirred for 1.5 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (10% methanol/chloroform) to obtain Compound 53 (3.6 mg, 12%).
$^{13}$CNMR (125 MHz, CDCl$_3$) δ; 13.3, 14.1, 15.0, 16.1, 17.0, 22.0, 25.3, 29.2, 29.8, 30.7, 31.5, 33.0, 36.0, 37.9, 41.1, 43.3, 44.9, 51.2, 52.8, 53.8, 54.0, 64.2, 65.8, 69.3, 69.5, 69.7, 70.3, 77.0, 77.9, 84.0, 91.6, 92.7, 96.5, 100.8, 118.3, 123.2, 125.9, 126.0, 135.8, 136.4, 141.5, 149.4, 157.3, 166.6, 192.4, 201.5, 206.4
FAB-MS (m/z); 927 (M−1)⁻

Example 28

Compound 54

Compound 10 (30.7 mg, 0.0373 mmol), molecular sieves 4A (45 mg) and 2,3,4,6-tetra-O-benzyl-α-D-glucopyranosyl trichloroacetimidate (44.9 mg, 0.0656 mmol) were added in dichloromethane (0.4 ml) for 4 hours. Trimethylsilyl trifluoromethanesulfonate (0.0014 ml, 0.0075 mmol) was added thereto with ice cooling and then the mixture was stirred overnight at a temperature below 5° C. Triethylamine (0.010 ml) was added to the reaction solution, the mixture was filtered through Celite, and the solvent was evaporated from the filtrate under reduced pressure, and the residue was purified by preparative thin layer chromatography (1% methanol/chloroform) to obtain Compound 54 (9.6 mg, 19%).
$^{13}$CNMR (100 MHz, CDCl$_3$) δ; 14.4, 14.5, 15.1, 16.1, 17.1, 20.9, 22.1, 25.2, 30.1, 30.9, 31.4, 34.5, 36.0, 38.4, 41.6, 41.9, 43.2, 51.3, 52.8, 53.8, 54.3, 68.7, 69.2, 72.0, 73.5, 74.9, 75.0, 75.4, 75.7, 78.3, 78.8, 82.6, 83.8, 85.1, 85.2, 90.7, 97.8, 100.9, 104.6, 117.5, 123.3, 125.7, 126.4, (127.57, 127.60, 127.7, 127.8, 128.0, 128.35, 128.40, 128.44) (20C), 136.1, 137.3, 138.1, 138.2, 138.5, 138.7, 141.5, 145.3, 157.3, 166.3, 170.4, 192.1, 197.3, 201.4
FAB-MS (m/z); 1345 (M−1)⁻

Example 29

Compound 55

Compound 56 (described later, 12.6 mg, 0.0102 mmol) was dissolved in methanol/dichloromethane (1/1, 2 ml), 5.1 N sodium methoxide (0.010 ml, 0.051 mmol) was added thereto, and then the mixture was stirred for 2.5 hours. 0.2 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 55 (6.0 mg, 49%).
$^{13}$CNMR (100 MHz, CDCl$_3$) δ; 13.3, 14.1, 15.1, 16.1, 17.0, 22.0, 25.4, 29.2, 29.8, 30.7, 31.4, 35.9, 36.0, 37.9, 41.1, 43.2, 45.0, 51.3, 52.8, 53.8, 54.1, 68.9, 69.3, 69.5, 71.5, 72.0, 73.5, 75.2, 76.8, 77.3, 78.0, 78.6, 84.0, 91.6, 92.4, 96.5, 100.8, 118.3, 122.9, 125.7, 126.2, (127.6, 127.65, 127.73, 127.9, 128.1, 128.37, 128.40, 128.44)(15C), 136.2, 136.5, 138.2, 138.5, 138.8, 141.5, 149.4, 157.3, 166.6, 192.4, 201.6, 206.5
FAB-MS (m/z); 1197 (M−1)⁻

Example 30

Compound 56

Compound 10 (47.6 mg, 0.0578 mmol) was dissolved in dichloromethane (2 ml), 3,4,6-tri-O-benzyl-D-glucal (272.8 mg, 0.655 mmol) and triphenylphosphine hydrobromide (184.6 mg, 0.538 mmol) were added thereto, and then the mixture was stirred at room temperature for 6 days. Then, saturated aqueous sodium hydrogen-carbonate was added thereto, the mixture was extracted with chloroform. The organic layer was washed with saturated brine and then dried over sodium sulfate. The solvent was evaporated under reduced pressure and the residue was purified by preparative thin layer chromatography (2% methanol/chloroform) to obtain Compound 56 (18.9 mg, 26%).
$^{13}$CNMR (100 MHz, CDCl$_3$) δ; 13.3, 14.2, 15.0, 16.0, 17.1, 20.9, 22.0, 25.2, 29.2, 30.1, 31.4 (2C), 35.8, 36.0, 37.8, 41.1, 42.0, 43.2, 51.3, 52.7, 53.8, 54.1, 68.7, 68.9, 71.5, 71.86, 71.92, 73.4, 75.1, 76.9, 77.9, 78.6, 78.8, 83.8, 90.7, 92.5, 97.8, 100.8, 117.5, 123.5, 125.6, 126.3, (127.59, 127.63, 127.7, 127.8, 128.1, 128.37, 128.41) (15C), 135.8, 137.3, 138.2, 138.5, 138.8, 141.5, 145.3, 157.3, 166.2, 170.4, 192.1, 201.5, 206.5
FAB-MS (m/z); 1239 (M−1)⁻

Example 31

Compound 57

Compound 10 (42.8 mg, 0.0519 mmol) was dissolved in dichloromethane (2 ml), 3,4,6-tri-O-acetyl-D-glucal (88.5 mg, 0.325 mmol) and triphenylphosphine hydrobromide (90.0 mg, 0.262 mmol) were added thereto, and the mixture was stirred overnight at room temperature. Saturated aqueous sodium hydrogencarbonate was added thereto, and the mixture was then extracted with chloroform. The organic layer was washed with saturated brine and dried over sodium sulfate. The solvent was evaporated under reduced pressure and the residue was purified by preparative thin layer chromatography (3% methanol/chloroform) to obtain Compound 57 (6.7 mg, 12%).
$^{13}$CNMR (100 MHz, CDCl$_3$) δ; 13.3, 14.2, 15.0, 16.0, 17.1, 20.8, 20.9, 21.0, 22.0, 22.9, 25.2, 29.3, 30.1, 31.4, 31.5, 35.2, 36.0, 37.8, 41.1, 42.0, 43.3, 51.3, 52.7, 53.8, 54.0, 62.3, 68.5, 68.7, 69.25, 69.30, 71.8, 77.6, 78.8, 83.8, 90.7, 92.2, 97.9, 100.9, 117.5, 123.9, 126.0 (2C), 135.3, 137.3, 141.5, 145.3, 157.3, 166.2, 169.9, 170.2, 170.3, 170.8, 192.0, 201.3, 206.4
FAB-MS (m/z); 1095 (M−1)⁻

Example 32

Compound 58

Compound 10 (48.5 mg, 0.0589 mmol) was dissolved in dichloromethane (2 ml), 3,4,6-tri-O-acetyl-D-galactal (151.2 mg, 0.555 mmol) and triphenylphosphine hydrobromide (97.0 mg, 0.283 mmol) were added thereto, and then the mixture was stirred overnight at room temperature. Saturated aqueous sodium hydrogen-carbonate was added thereto, and the mixture was extracted with chloroform. The organic layer was washed with saturated brine and then dried over sodium sulfate. The solvent was evaporated under reduced pressure and the residue was purified by preparative thin layer chromatography (5% methanol/chloroform) to obtain Compound 58 (6.7 mg, 10%).
$^{13}$CNMR (100 MHz, CDCl$_3$) δ; 13.3, 14.3, 15.0, 16.1, 17.1, 20.7, 20.8, 20.9, 22.0, 22.9, 25.2, 29.2, 30.1, 31.4, 31.5, 32.1, 36.0, 37.8, 41.1, 42.0, 43.3, 51.3, 52.8, 53.8, 54.1, 62.6, 66.8, 68.4, 68.7, 71.5, 71.9, 77.4, 78.7, 83.8, 90.8, 92.4, 97.8, 100.9, 117.5, 123.8, 125.7, 126.2, 135.5, 137.3, 141.5, 145.3, 157.3, 166.2, 170.1, 170.36, 170.40, 170.6, 192.1, 201.3, 206.4
FAB-MS (m/z); 1095 (M−1)$^-$ Example 33

Compound 59

Compound 10 (20.9 mg, 0.0254 mmol) was dissolved in dichloromethane (1 ml), 3,4-di-O-acetyl-6-deoxy-L-glucal (0.0291 ml, 0.152 mmol) and triphenylphosphine hydrobromide (34.5 mg, 0.100 mmol) were added thereto, and then the mixture was stirred at room temperature for 2 nights. Saturated aqueous sodium hydrogen-carbonate was added thereto, and the mixture was extracted with chloroform. The organic layer was washed with saturated brine and then dried over sodium sulfate. The solvent was evaporated under reduced pressure and the residue was purified by preparative thin layer chromatography (5% methanol/chloroform) to obtain Compound 59 (17.4 mg, 66%).
$^{13}$CNMR (125 MHz, CDCl$_3$) δ; 14.0, 14.4, 15.0, 16.0, 17.0, 17.5, 20.89, 20.93, 21.1, 21.9, 25.2, 30.0, 31.1, 31.4, 34.3, 35.4, 36.0, 38.4, 41.6, 41.9, 43.3, 51.2, 52.7, 53.8, 54.2, 66.4, 68.7, 69.3, 71.9, 74.8, 78.7, 83.8, 84.5, 90.7, 97.8, 99.0, 100.8, 117.5, 123.6, 126.2, 126.8, 135.7, 137.3, 141.5, 145.3, 157.3, 166.2, 170.25, 170.29, 170.4, 192.1, 201.3, 206.4
FAB-MS (m/z); 1037 (M−1)$^-$ Example 34

Compound 60

Compound 63 (described later, 108.2 mg, 0.0289 mmol) was dissolved in tetrahydrofuran (3 ml), tetrabutylammonium fluoride (0.103 ml, a 1 N solution in tetrahydrofuran, 0.103 mmol) was added thereto, and then the mixture was stirred at room temperature for 4.5 hours. Water was added thereto, and the mixture was extracted with chloroform. The organic layer was washed with saturated brine and then dried over sodium sulfate. The solvent was evaporated under reduced pressure and the residue was purified by preparative thin layer chromatography (5% methanol/chloroform) to obtain Compound 60 (57.7 mg, 60%).
$^{13}$CNMR (100 MHz, CDCl$_3$) δ; 14.2, 14.4, 15.0, 16.1, 17.1, 18.0, 20.9, 22.0, 25.2, 30.0, 31.0, 31.4, 34.7, 36.0, 38.3, 41.7, 41.9, 43.4, 51.3, 52.7, 53.8, 54.3, 68.4, 68.7, 69.7, 71.9, 78.7, 83.8, 84.9, 90.7, 96.6, 97.8, 100.8, 117.5, 123.5, 126.0 (2C), 126.4, 133.4, 135.8, 137.3, 141.5, 145.3, 157.3, 166.2, 170.4, 192.1, 201.4, 206.5
FAB-MS (m/z); 935 (M−1)$^-$ Example 35

Compound 61

Compound 10 (41.2 mg, 0.0500 mmol) was dissolved in dichloromethane (2 ml), 3,4-di-O-acetyl-6-deoxy-L-glucal (0.0576 ml, 0.300 mmol) and camphorsulfonic acid (21.3 mg, 0.0917mmol) were added thereto, and the mixture was stirred at room temperature for two nights. Saturated aqueous sodium hydrogencarbonate was added thereto, and the mixture was extracted with chloroform. The organic layer was washed with saturated brine and then dried over sodium sulfate. The solvent was evaporated under reduced pressure and the residue was purified by preparative thin layer chromatography (2.5% methanol/chloroform) to obtain Compound 61 (12.4 mg, 25%).
$^{13}$CNMR (100 MHz, CDCl$_3$) δ; 14.2, 14.4, 15.0, 16.1, 17.1, 18.0, 20.9, 21.1, 22.0, 25.2, 30.1, 31.0, 31.5, 34.7, 36.0, 38.3, 41.7, 41.9, 43.4, 51.3, 52.7, 53.8, 54.3, 65.3, 68.7, 70.9, 71.9, 78.7, 83.8, 85.1, 90.7, 96.6, 97.8, 100.9, 117.5, 123.5, 126.0, 126.1, 127.5, 129.8, 135.8, 137.3, 141.5, 145.3, 157.3, 166.2, 170.4, 170.6, 192.1, 201.3, 206.5
FAB-MS (m/z); 977 (M−1)$^-$ Example 36

Compound 62

Compound 63 (described later, 31.4 mg, 0.0299 mmol) was dissolved in methanol/dichloromethane (1/1, 2 ml), 5.1 N sodium methoxide (0.010 ml, 0.51 mmol) was added thereto, and then the mixture was stirred for 4 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 62 (3.9 mg, 32%).
$^{13}$CNMR (100 MHz, CDCl$_3$) δ; 5.1 (3C), 6.8 (3C), 14.2, 14.4, 15.0, 16.1, 17.0, 18.1, 22.0, 25.3, 29.8, 30.8, 31.1, 34.7, 36.0, 38.4, 41.7, 43.4, 44.9, 51.3, 52.8, 53.8, 54.2, 68.2 (2C), 69.3, 70.2, 78.0, 84.0, 84.7, 91.6, 96.5, 96.7, 100.9, 118.3, 122.9, 125.3, 125.9, 126.3, 134.7, 136.3, 136.4, 141.5, 149.4, 157.3, 166.6, 192.4, 200.5, 206.2
FAB-MS (m/z); 1007 (M−1)$^-$ Example 37

Compound 63

Compound 10 (46.7 mg, 0.0567 mmol) was dissolved in dichloromethane (1 ml), 3,4-di-O-triethylsilyl-6-deoxy-L-glucal (106.3 mg, 0.297 mmol) and a trifluoroborane diethyl ether complex (0.0014 ml, 0.0114 mmol) were added thereto, and then the mixture was stirred for 1.5 hours with ice cooling. Saturated aqueous sodium hydrogencarbonate was added thereto, and the mixture was extracted with chloroform. The organic layer was washed with saturated brine and then dried over sodium sulfate. The solvent was evaporated under reduced pressure and the residue was purified by preparative thin layer chromatography (1% methanol/chloroform) to obtain Compound 63 (56.9 mg, 96%).
$^{13}$CNMR (100 MHz, CDCl$_3$) δ; 5.1 (3C), 6.8 (3C), 14.2, 14.4, 15.0, 16.0, 17.1, 18.1, 20.9, 22.0, 25.2, 30.0, 31.0, 31.4, 34.7, 36.0, 38.3, 41.7, 41.9, 43.3, 51.3, 52.7, 53.8, 54.3, 68.2, 68.7, 70.2, 71.9, 78.7, 83.8, 84.7, 90.7, 96.7, 97.8, 100.8, 117.5, 123.4, 125.3, 125.8, 126.2, 134.6, 135.9, 137.3, 141.4, 145.3, 157.3, 166.2, 170.3, 192.0, 201.4, 206.5
FAB-MS (m/z); 1049 (M−1)$^-$ Example 38

Compound 64

Compound 10 (51.7 mg, 0.0627 mmol) was dissolved in dichloromethane (1 ml), 3,4,6-tri-O-triethylsilyl-D-glucal (318.2 mg, 0.652 mmol) and a trifluoroborane diethyl ether complex (0.0025 ml, 0.020 mmol) were added thereto with ice cooling, and then the mixture was stirred for five days at room temperature. Saturated aqueous sodium hydrogencarbonate was added thereto, and the mixture was extracted with chloroform. The organic layer was washed with saturated brine and then dried over sodium sulfate. The solvent was evaporated under reduced pressure, and the residue was purified by preparative thin layer chromatography (2% methanol/chloroform) to obtain Compound 64 (52.5 mg, 71%).

$^{13}$CNMR (100 MHz, CDCl$_3$) δ; 4.5 (2C), 5.1 (2C), 5.8 (2C), 6.6 (2C), 6.78 (2C), 6.82 (2C), 13.6, 14.3, 15.0, 16.0, 17.1, 20.9, 22.0, 25.2, 30.1, 30.3, 31.1, 31.5, 36.0, 37.8, 41.4, 41.9, 43.3, 51.4, 52.7, 53.8, 54.2, 61.4, 63.4, 68.7, 71.9, 72.6, 78.7, 79.0, 83.8, 90.7, 90.8, 97.8, 100.8, 117.5, 123.3, 124.9, 125.6, 126.8, 134.9, 136.0, 137.3, 141.5, 145.3, 157.3, 166.2, 170.3, 192.1, 201.4, 206.6

FAB-MS (m/z); 1179 (M−1)$^-$

Example 39

Compound 65

Compound 2 (428.9 mg, 0.298 mmol) was dissolved in acetone (40 ml), 0.2 N hydrochloric acid (20 ml) was added thereto, and then the mixture was stirred at room temperature for 6 days. Acetone was evaporated under reduced pressure, and the mixture was extracted with chloroform. The organic layer was washed with water and dried over sodium sulfate. The solvent was evaporated under reduced pressure, and the residue was purified by silica gel column chromatography (2% methanol/chloroform) and preparative thin layer chromatography (2% methanol/chloroform) to obtain Compound 65 (18.1 mg, 5%).

$^{13}$CNMR (100 MHz, CDCl$_3$) δ; 14.0, 14.4, 15.1, 16.0, 17.1, 17.6, 18.1, 18.2, 20.9, 21.0, 21.2, 22.0, 25.2, 26.3, 29.6, 30.1, 31.1, 31.4, 31.5, 34.6, 36.0, 36.1, 38.4, 41.6, 41.9, 43.3, 51.2, 52.8, 53.8, 54.3, 62.2, 66.7, 67.8, 68.7, 70.2, 71.3, 71.9, 72.3, 74.5, 78.7, 81.4, 83.8, 84.3, 90.7, 92.5, 97.7, 98.5, 99.2, 100.8, 117.5, 123.5, 126.0, 126.4, 135.8, 137.3, 141.5, 145.3, 157.3, 166.3, 170.4 (2C), 171.4, 192.1, 201.4, 206.5

FAB-MS (m/z); 1281 (M−1)$^-$

Example 40

Compound 66

Compound 10 (47.8 mg, 0.0580 mmol), molecular sieves 4A (90 mg) and 2,3,4,6-tetra-O-acetyl-α-D-glucopyranosyl trichloroacetimidate (62.6 mg, 0.127 mmol) were stirred in dichloromethane (0.4 ml) for 4 hours. To the solution was added trimethylsilyl trifluoromethanesulfonate (0.0022 ml, 0.011 mmol) with ice cooling, and then the mixture was stirred overnight at a temperature below 5° C. Triethylamine (0.010 ml) was added to the reaction solution and the mixture was filtered through Celite. The solvent was evaporated from the filtrate under reduced pressure, and the residue was purified by preparative thin layer chromatography (5% methanol/chloroform) to obtain Compound 66 (30.2 mg, 66%).

$^{13}$CNMR (100 MHz, CDCl$_3$) δ; 13.7, 14.3, 15.0, 16.0, 17.1, 20.79, 20.81 (2C), 20.9, 21.9, 22.4, 25.2, 30.0, 31.1, 31.4, 34.0, 36.0, 37.7, 41.6, 41.9, 43.6, 51.4, 52.7, 53.8, 54.0, 63.2, 67.4, 68.2, 68.7, 70.3, 71.9, 73.8, 78.2, 78.7, 83.8, 90.7, 97.2, 97.8, 100.9, 117.5, 121.9, 123.6, 125.5, 126.5, 135.6, 137.3, 141.5, 145.3, 157.3, 166.2, 169.1, 169.6, 170.4, 170.7, 192.0, 201.2, 206.4

FAB-MS (m/z); 1153 (M−1)$^-$

Example 41

Compound 67

Compound 60 (24.1 mg, 0.0257 mmol) was dissolved in methanol/methylene chloride (1/1, 2 ml), 5.1 N sodium methoxide (0.010 ml, 0.51 mmol) was added thereto, and then the mixture was stirred for 5 hours. 0.1 N Hydrochloric acid was added to the reaction solution, the mixture was extracted with chloroform, and the organic layer was washed with saturated brine and then dried over sodium sulfate. The solvent was evaporated under reduced pressure, and the residue was purified by preparative thin layer chromatography (5% methanol/chloroform) to obtain Compound 67 (17.0 mg, 74%).

$^{13}$CNMR (100 MHz, CDCl$_3$) δ; 14.2, 14.4, 15.0, 16.1, 17.0, 18.0, 22.0, 25.3, 29.8, 30.8, 31.1, 34.7, 36.0, 38.4, 41.7, 43.4, 44.9, 51.3, 52.8, 53.8, 54.3, 68.4, 69.3, 69.5, 69.7, 78.0, 84.0, 85.0, 91.6, 96.5, 96.6, 100.9, 118.3, 123.0, 126.1 (2C), 126.5, 133.4, 136.2, 136.5, 141.5, 149.4, 157.3, 166.6, 192.4, 201.5, 206.5

FAB-MS (m/z); 893 (M−1)$^-$

Example 42

Compound 68

Compound 10 (54.1 mg, 0.0656 mmol) and 3-iodobenzyl trichloroacetimidate (153.8 mg, 0.406 mmol) were dissolved in toluene (2 ml), trifluoromethanesulfonic acid (0.0054 ml, 0.061 mmol) was added thereto, and then the mixture was stirred at room temperature for 3 hours. Triethylamine (0.05 ml) was added to the reaction solution, and the solvent was evaporated under reduced pressure. The residue was purified by preparative thin layer chromatography (2.5% methanol/chloroform) to obtain Compound 68 (1.2 mg, 2%).

$^{13}$CNMR (100 MHz, CDCl) δ; 13.4, 14.4, 15.1, 16.1, 17.1, 20.9, 22.0, 25.2, 30.1, 30.7, 31.2, 31.5, 36.0, 38.3, 41.3, 42.0, 43.1, 51.4, 52.8, 53.9, 54.2, 68.7, 69.5, 71.9, 78.8, 83.0, 83.8, 90.8, 97.8, 100.9, 117.5, 123.4, 125.4, 126.5, 126.6, 130.1, 136.0, 136.4, 136.5, 136.7, 137.3, 141.3, 141.5, 145.3, 157.3, 166.2, 170.4, 192.1, 201.4, 206.7

FAB-MS (m/z); 1039 (M−1)$^-$

Test Example 1

Apoptosis Inducing Activity for HeLa Cells and HeLa/bcl-2 Cells

Apoptosis inducing activity of the medicaments of the present invention was determined by measuring enzymatic activity of caspase activated in the process of apoptosis induction as described below,. HeLa cells or HeLa cells into which the bcl-2 gene was introduced (HeLa/bcl-2 cells) contained in DME medium containing 10% fetal calf serum (NISSUI PHARMACEUTICAL CO., LTD., referred to as "Medium A" hereinafter in the example) were placed in each well of 96-well microtiter plates in an amount of 3×10$^4$ cell. The cells on the plates were cultured in a carbon dioxide gas incubator at 37° C. for 12 hours, then a test compound appropriately diluted with Medium A was added to each well in an amount of 10 μl, and the cells were further cultured in a carbon dioxide gas incubator at 37° C. for 6 hours. After the culture supernatant was removed, the cells were lysed, and to the cell lysate was added a fluorescent substrate of caspase, Ac-DEVD-AMC (Peptide Laboratory). Then, the caspase activity was determined by measuring AMC (7-amino-4-methylcoumarin) released as a result of degradation of Ac-DEVD-AMC by caspase remained in the cell lysate through measurement of fluorescence intensity at 460 nm. The results are shown in Table 2.

TABLE 2

Apoptosis inducing activity for HeLa cells and HeLa/bcl-2 cells

| Compound No. | Rate of Caspase Activation(%, Drug concentration: 5 μM) | |
|---|---|---|
| | HeLa cell | HeLa/bcl-2 cell |
| No drug | 100 | 100 |
| 22 | 243 | 1078 |
| 28 | 148 | 2304 |
| 29 | 169 | 1639 |
| 31 | 97 | 3372 |
| 40 | 147 | 1300 |
| 41 | 146 | 343 |
| 49 | 185 | 1450 |
| 55 | 106 | 448 |
| 58 | 96 | 350 |
| 61 | 213 | 370 |

Test Example 2

Anti-Fas Antibody-dependent Apoptosis Inducing Activity for HeLa/bcl-2 Cells

In HeLa/bcl-2 cells into which the bcl-2 gene is introduced, apoptosis is suppressed by the bcl-2 gene. For this reason, they acquire resistance to apoptosis induced by various anticancer agents or anti-Fas antibodies. Test compounds were examined in their eliminating effect on the apoptosis resistance of HeLa/bcl-2 by simultaneously adding an anti-Fas antibody and each test compound to HeLa/bcl-2 cells and detecting enzymatic activity of caspase that was activated in the process of apoptosis induction as described below. HeLa/bcl-2 cells in Medium A were placed in each well of a 96-well microtiter plate in an amount of $3\times10^4$ cells. The plate was incubated in a carbon dioxide gas incubator at 37° C. for 12 hours, then each test compound appropriately diluted with Medium A (10 μl) and an anti-Fas monoclonal antibody (CH11, 10 ng) were simultaneously added to each well, and the plate was further incubated in a carbon dioxide gas incubator at 37° C. for 6 hours. After the culture supernatant was removed, the cells were lysed, and caspase activity was measured in the same manner as in Test Example 1. The results are shown in Table 3. The enzymatic activity of caspase, which was not increased by an anti-Fas antibody alone, was increased by the treatment with the anti-Fas antibody together with the test compound. These results clearly indicate that anti-Fas-dependent apoptosis was induced by direct or indirect inhibitory action of the test compounds against the function of the product of the bcl-2 gene introduced into HeLa/bcl-2.

TABLE 3

Anti-Fas antibody-dependent apoptosis inducing activity for HeLa/bcl-2 cells

| Compound No. | Rate of Caspase Activation (%, Drug concentration: 5 μM) HeLa/bcl-2 cell |
|---|---|
| Anti-Fas antibody | 100 |
| 1 | 964 |
| 22 | 444 |
| 28 | 1124 |
| 29 | 1303 |

TABLE 3-continued

Anti-Fas antibody-dependent apoptosis inducing activity for HeLa/bcl-2 cells

| Compound No. | Rate of Caspase Activation (%, Drug concentration: 5 μM) HeLa/bcl-2 cell |
|---|---|
| 31 | 1051 |
| 49 | 477 |
| 51 | 460 |
| 57 | 446 |
| 60 | 526 |
| 61 | 452 |
| 65 | 659 |

Test Example 3

Cytotoxic Activity for HeLa/bcl-2 Cells

HeLa/bcl-2 cells in Medium A were placed in each well of a 96-well microtiter plate in an amount of $3\times10^4$ cells. The plate was incubated in a carbon dioxide gas incubator at 37° C. for 12 hours, then 10 μl of each test compound appropriately diluted with Medium A was added to each well, and the incubation was further continued in a carbon dioxide gas incubator at 37° C. After 24 hours, the number of surviving cells was counted by the XTT staining and compared with the number of surviving cells without treatment by a test drug to calculate $IC_{50}$ (μM) for growth shown in Table 4.

TABLE 4

Cytotoxic activity for HeLa/bcl-2 cells

| Compound No. | Growth Inhibition ($IC_{50}$, μM) HeLa/bcl-2 cell |
|---|---|
| 22 | 1.8 |
| 28 | 1.3 |
| 29 | 1.5 |
| 31 | 1.0 |
| 40 | 0.75 |

Test Example 4

Growth Inhibition Test for Hormone-dependent Human Breast Cancer MCF-7 Cell Strain Cells were placed in each well of a 96-well microplate (Nunc, #167008) in an amount of 4000 cells per well, and the cells were pre-cultured in RPMI 1640 medium containing 5% fetal calf serum (FCS) for 24 hours in a 5% carbon dioxide gas incubator at 37° C. Then, a solution of each test compound in dimethyl sulfoxide (DMSO) prepared at a concentration of 10 mmol/L was serially diluted with the culture medium and added to each well (final volume: 100 μL/well). The cells were then further cultured for 72 hours in a 5% carbon dioxide gas incubator at 37° C. Five hours before completion of the culture, 4,5-dimethylthiazol-2-yl)-2,5-diphenyltetrazolium bromide (Sigma, abbreviated as "MTT" hereinafter) prepared at a concentration of 6 mg/mL with the culture medium was added in an amount of 10 μL per well. After the completion of culture, the medium was sucked, DMSO was added to each well in an amount of 150 μL per well and the mixture was vigorously stirred by using a plate mixer to completely dissolve the crystals of MTT-formazan. Then, difference of absorbance at 550 nm and 630 nm was determined by using a microplate reader (M-Spmax250, Wako Pure Chemicals). Inhibitory activity on the cell growth was calculated as 50% growth inhibitory concentration ($IC_{50}$) based on a 4-parameter logistic calibration curve by using the formula of the analysis software (SOFTmax-J Ver.2.1) equipped with microplate reader. The results are shown in Table 5.

TABLE 5

Cell growth inhibitory activity

| Compound No. | MCF-7 cell $IC_{50}$ (μM) |
|---|---|
| 20 | 10.86 |
| 27 | 0.98 |
| 29 | 0.125 |
| 31 | 0.14 |
| 37 | 5.11 |
| 38 | 1.22 |
| 39 | 0.81 |
| 40 | 0.24 |
| 49 | 1.59 |
| 51 | 1.36 |
| 56 | 0.63 |
| 57 | 1.65 |
| 59 | 0.98 |
| 61 | 1.45 |
| 63 | 0.72 |
| 65 | 0.52 |
| 66 | 1.40 |

Test Example 5

Antibacterial Activity

Antibacterial activity was determined by the agar dilution method using a medium prepared by dissolving 3 g of Bacto trypton (Difco), 3 g of meat extract, 1 g of yeast extract, 1 g of glucose, and 16 g of agar in 1 L of water (pH 7). The antibacterial activities of typical compounds are shown in Table 6 as minimum growth inhibitory concentrations (MIC)

TABLE 6

Antibacterial activity

| Compound No. | Bacterial Name and MIC (μg/ml) | | |
|---|---|---|---|
|  | BS | EH | SA |
| 22 | — | 21 | 42 |
| 24 | 2.9 | >92 | >92 |
| 25 | >83 | — | — |
| 26 | 125 | — | — |
| 29 | 5.2 | — | — |
| 37 | 0.42 | — | — |
| 38 | 12.5 | — | — |
| 40 | 0.09 | >91.7 | >91.7 |
| 49 | >58.3 | 29.0 | 15.0 |
| 51 | 6.25 | 1.56 | 1.56 |
| 53 | 16.7 | — | — |
| 59 | 16.7 | >66.7 | >66.7 |
| 60 | >83.3 | — | — |
| 61 | 10.4 | — | — |
| 63 | >91.7 | — | — |
| 65 | 2.34 | — | — |
| 66 | >60.0 | 60.0 | 60.0 |

—: Inactive
BS: *Bacillus Subtilis* ATCC10707
EH: *Enterococcus hirae* ATCC10541
SA: *Staphylococcus aureus* ATCC6538P Industrial Applicability The medicament of the present invention comprising the compound represented by formula (I) or a physiologically acceptable salt thereof as an active ingredient has an action for inducing apoptosis, and is useful for preventive and/or theraputic treatment of various kinds of diseases such as cancers and AIDS. The compound represented by formula (Ia) and a salt thereof can be used as an active ingredient of a medicament such as an anticancer agent or an antibacterial agent.

What is claimed is:

1. A method for inducing apoptosis which comprises administering to a subject in need thereof, as an active ingredient, an effective amount to induce apoptosis of a tetrocarcin derivative represented by the following general formula (I) or a physiologically acceptable salt thereof:

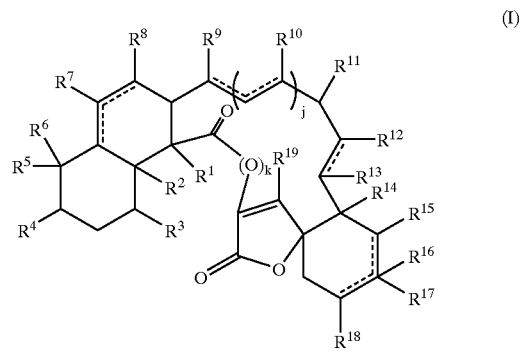

wherein ---- represents a single bond or a double bond provided that two adjacent bonds are not simultaneously double bonds;

j and k represent 0 or 1;

$R^1$, $R^2$, $R^3$, $R^7$, $R^8$, $R^{10}$, and $R^{14}$ independently represent a hydrogen atom, a substituted or unsubstituted lower alkyl group, a formyl group or a carboxyl group;

$R^4$, $R^{12}$, $R^{13}$, and $R^{15}$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O($CH_2$)$_m$]$_p$Si($R^{20}$)($R^{21}$)($R^{22}$) (in the formula, m and p independently represent an integer of from 0 to 8, and $R^{20}$, $R^{21}$, and $R^{22}$ independently represent a lower alkyl group or a substituted or unsubstituted aryl group);

$R^{16}$, $R^{17}$, and $R^{18}$ independently represent a hydrogen atom, a hydroxyl group, a substituted or unsubstituted lower alkyl group, a substituted or unsubstituted lower alkanoyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, a group represented by —[O($CH_2$)$_m$]$_p$Si($R^{20}$)($R^{21}$)($R^{22}$) (in the formula, m, p, $R^{20}$, $R^{21}$, and $R^{22}$ have the same meanings as those defined above), a substituted or unsubstituted lower alkoxyalkyl group, a formyl group, a carboxyl group, a substituted or unsubstituted lower alkoxycarbonyl group, a substituted or unsubstituted lower alkanoyloxyalkyl group, a group represented by —(CH$_2$)$_r$OSi(R$^{23}$)(R$^{24}$)(R$^{25}$) (in the formula, r represents an integer of from 1 to 8, R$^{23}$, R$^{24}$, and R$^{25}$ independently represent a lower alkyl group or a substituted or unsubstituted aryl group), a group represented by —CH=CHR$^{26}$ (in the formula, R$^{26}$ represents a substituted or unsubstituted lower alkoxycarbonyl group), a group represented by —CH=NOR$^{27}$ (in the formula, R$^{27}$ represents a hydrogen atom or a substituted or unsubstituted lower alkyl group), or —CH(X$^1$R$^{28}$)$_2$ (in the formula, X$^1$ represents an oxygen atom or a sulfur atom, and R$^{28}$ represents a lower alkyl group or two of R$^{28}$ are combined together to represent —(CH$_2$)$_2$— or —(CH$_2$)$_3$—), or R$^{16}$ and R$^{17}$ are combined together to represent an oxygen atom;

R$^{11}$ represents a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, R$^{20}$, R$^{21}$, and R$^{22}$ have the same meanings as those defined above), or a group represented by the following formula (A):

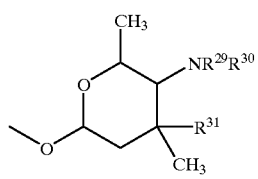

(A)

(in the formula, R$^{29}$ represents a hydrogen atom or a lower alkyl group, R$^{30}$ represents a hydrogen atom, a substituted or unsubstituted lower alkyl group, a substituted or unsubstituted lower alkanoyl group, or a substituted or unsubstituted lower alkoxycarbonyl group, and R$^{31}$ represents a nitro group, a nitroso group, a hydroxyl group, or an amino group);

R$^{19}$ represents a hydroxyl group, a substituted or unsubstituted lower alkoxyl group, or a substituted or unsubstituted lower alkanoyloxy group;

R$^5$ and R$^6$ are combined together to represent an oxygen atom or R$^5$ and R$^6$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted aroyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, R$^{20}$, R$^{21}$, and R$^{22}$ have the same meanings as those defined above), or when R$^5$ represents a hydrogen atom, R$^6$ may be a group selected from the group consisting of the groups represented by the following formulas (B), (B-2), (C-1), (C-2), (D), and (E):

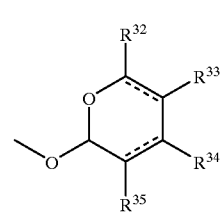

(B)

(in the formula, ---- represents a single bond or a double bond, R$^{32}$ represents a hydrogen atom, a formyl group, or a group represented by —CH$_2$R$^{32a}$, and R$^{33}$, R$^{34}$, R$^{35}$, and R$^{32a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20a}$)(R$^{21a}$)(R$^{22a}$) (in the formula, R$^{20a}$, R$^{21a}$, and R$^{22a}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

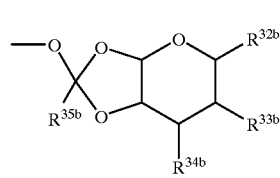

(B-2)

(in the formula, R$^{35b}$ represents a substituted or unsubstituted lower alkyl group, R$^{32b}$ represents a hydrogen atom, a formyl group, or a group represented by —CH$_2$R$^{32c}$, and R$^{33b}$, R$^{34b}$, and R$^{32c}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20a1}$)(R$^{21a1}$)(R$^{22a1}$) (in the formula, R$^{20a1}$, R$^{21a1}$, and R$^{22a1}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

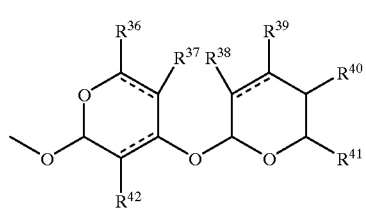

(C-1)

(in the formula, ---- represents a single bond or a double bond, $R^{36}$ represents a hydrogen atom, a formyl group, or a group represented by —CH$_2$R$^{36a}$, $R^{41}$ represents a hydrogen atom or a group represented by —CH$_2$R$^{41a}$, and $R^{37}$, $R^{38}$, $R^{39}$, $R^{40}$, $R^{41a}$, $R^{42}$, and $R^{36a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20b}$)(R$^{21b}$)(R$^{22b}$) (in the formula, R$^{20b}$, R$^{21b}$, and R$^{22b}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

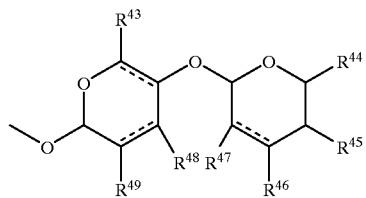

(C-2)

(in the formula, ---- represents a single bond or a double bond, $R^{43}$ represents a hydrogen atom, a formyl group or a group represented by —CH$_2$R$^{43a}$, $R^{44}$ represents a hydrogen atom or a group represented by —CH$_2$R$^{44a}$, and $R^{44a}$, $R^{45}$, $R^{46}$, $R^{47}$, $R^{48}$, $R^{49}$, and $R^{43a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20c}$)(R$^{21c}$)(R$^{22c}$) (in the formula, R$^{20c}$, R$^{21c}$, and R$^{22c}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

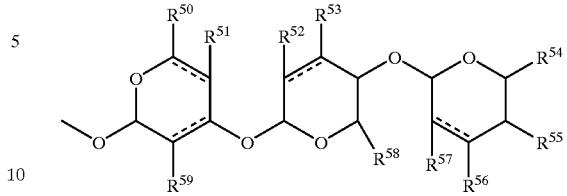

(D)

(in the formula, ---- represents a single bond or a double bond, $R^{50}$ represents a hydrogen atom, a formyl group or a group represented by —CH$_2$R$^{50a}$, $R^{58}$ represents a hydrogen atom or a group represented by —CH$_2$R$^{58a}$, $R^{54}$ represents a hydrogen atom or a group represented by —CH$_2$R$^{54a}$, and $R^{51}$, $R^{52}$, $R^{53}$, $R^{54a}$, $R^{55}$, $R^{56}$, $R^{57}$, $R^{58a}$, $R^{59}$, and $R^{50a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20d}$)(R$^{21d}$)(R$^{22d}$) (in the formula, R$^{20d}$, R$^{21d}$, and R$^{22d}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)); and

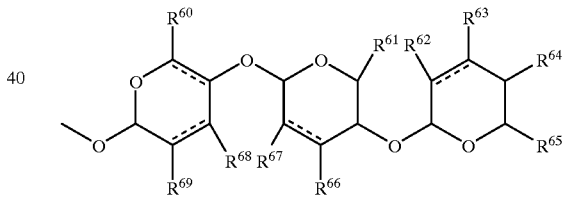

(E)

(in the formula, ---- represents a single bond or a double bond, $R^{60}$ represents a hydrogen atom, a formyl group or a group represented by —CH$_2$R$^{60a}$, $R^{61}$ represents a hydrogen atom or a group represented by —CH$_2$R$^{61a}$, $R^{65}$ represents a hydrogen atom or a group represented by —CH$_2$R$^{65a}$, and $R^{61a}$, $R^{62}$, $R^{63}$, $R^{64}$, $R^{65a}$, $R^{66}$, $R^{67}$, $R^{68}$, $R^{69}$, and $R^{60a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20e}$)(R$^{21e}$)(R$^{22e}$) (in the formula, R$^{20e}$, R$^{21e}$, and R$^{22e}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)).

2. A method for preventive and/or therapeutic treatment of a disease resulting from increased expression of a Bcl-2 family protein, comprising administering a preventively and/or therapeutically effective amount of a tetrocarcin derivative or a physiologically acceptable salt thereof to a mammal, the tetrocarcin derivative or physiologically acceptable salt thereof represented by the following general formula (I) or a physiologically acceptable salt thereof:

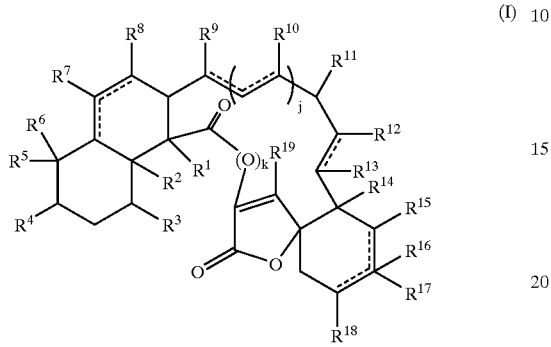
(I)

wherein ---- represents a single bond or a double bond provided that two adjacent bonds are not simultaneously double bonds;

j and k represent 0 or 1;

$R^1$, $R^2$, $R^3$, $R^7$, $R^8$, $R^9$, $R^{10}$, and $R^{14}$ independently represent a hydrogen atom, a substituted or unsubstituted lower alkyl group, a formyl group or a carboxyl group;

$R^4$, $R^{12}$, $R^{13}$, and $R^{15}$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m and p independently represent an integer of from 0 to 8, and $R^{20}$, $R^{21}$, and $R^{22}$ independently represent a lower alkyl group or a substituted or unsubstituted aryl group);

$R^{16}$, $R^{17}$, and $R^{18}$ independently represent a hydrogen atom, a hydroxyl group, a substituted or unsubstituted lower alkyl group, a substituted or unsubstituted lower alkanoyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), a substituted or unsubstituted lower alkoxyalkyl group, a formyl group, a carboxyl group, a substituted or unsubstituted lower alkoxycarbonyl group, a substituted or unsubstituted lower alkanoyloxyalkyl group, a group represented by —(CH$_2$)$_r$OSi(R$^{23}$)(R$^{24}$)(R$^{25}$) (in the formula, r represents an integer of from 1 to 8, $R^{23}$, $R^{24}$, and $R^{25}$ independently represent a lower alkyl group or a substituted or unsubstituted aryl group), a group represented by —CH=CHR$^{26}$ (in the formula, $R^{26}$ represents a substituted or unsubstituted lower alkoxycarbonyl group), a group represented by —CH=NOR$^{27}$ (in the formula, $R^{27}$ represents a hydrogen atom or a substituted or unsubstituted lower alkyl group), or —CH(X$^1$R$^{28}$)$_2$ (in the formula, X$^1$ represents an oxygen atom or a sulfur atom, and $R^{28}$ represents a lower alkyl group or two of $R^{28}$ are combined together to represent —(CH$_2$)$_2$— or —(CH$_2$)$_3$—), or $R^{16}$ and $R^{17}$ are combined together to represent an oxygen atom;

$R^{11}$ represents a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), or a group represented by the following formula (A):

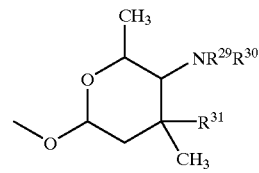
(A)

(in the formula, $R^{29}$ represents a hydrogen atom or a lower alkyl group, $R^{30}$ represents a hydrogen atom, a substituted or unsubstituted lower alkyl group, a substituted or unsubstituted lower alkanoyl group, or a substituted or unsubstituted lower alkoxycarbonyl group, and $R^{31}$ represents a nitro group, a nitroso group, a hydroxyl group, or an amino group);

$R^{19}$ represents a hydroxyl group, a substituted or unsubstituted lower alkoxyl group, or a substituted or unsubstituted lower alkanoyloxy group;

$R^5$ and $R^6$ are combined together to represent an oxygen atom or $R^5$ and $R^6$ independently represent a hydrogen atom, a hydroxyl group, a substituted or unsubstituted lower alkyl group, a substituted or unsubstituted lower alkanoyloxy group, a substituted or unsubstituted aralkyloxy group, a substituted or unsubstituted aroyloxy group, a substituted or unsubstituted lower alkoxyl group, a substituted or unsubstituted aryloxy group, a substituted or unsubstituted lower alkoxycarbonyloxy group, a substituted or unsubstituted lower alkenoyloxy group, a substituted or unsubstituted aroyloxy group, a substituted or unsubstituted arylsulfonyloxy group, a substituted or unsubstituted aroyloxyalkyl group, or a group represented by —[O(CH$_2$)$_m$]$_p$Si(R$^{20}$)(R$^{21}$)(R$^{22}$) (in the formula, m, p, $R^{20}$, $R^{21}$, and $R^{22}$ have the same meanings as those defined above), or when $R^5$ represents a hydrogen atom, $R^6$ may be a group selected from the group consisting of the groups represented by the following formulas (B), (B-2), (C-1), (C-2), (D), and (E):

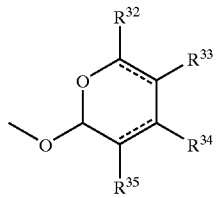
(B)

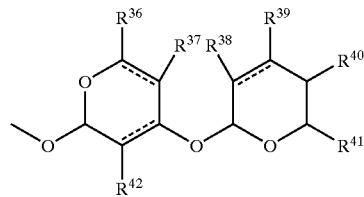
(C-1)

(in the formula, ---- represents a single bond or a double bond, $R^{32}$ represents a hydrogen atom, a formyl group, or a group represented by —CH$_2$R$^{32a}$, and $R^{33}$, $R^{34}$, $R^{35}$, and $R^{32a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20a}$)(R$^{21a}$)(R$^{22a}$) (in the formula, $R^{20a}$, $R^{21a}$, and $R^{22a}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

(in the formula, ---- represents a single bond or a double bond, $R^{36}$ represents a hydrogen atom, a formyl group, or a group represented by —CH$_2$R$^{36a}$, $R^{41}$ represents a hydrogen atom or a group represented by —CH$_2$R$^{41a}$, and $R^{37}$, $R^{38}$, $R^{39}$, $R^{40}$, $R^{41a}$, $R^{42}$, and $R^{36a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20b}$)(R$^{21b}$)(R$^{22b}$) (in the formula, $R^{20b}$, $R^{21b}$, and $R^{22b}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

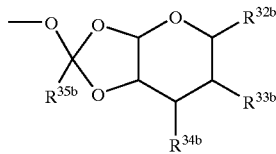
(B-2)

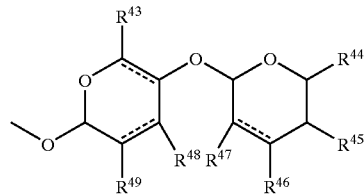
(C-2)

(in the formula, $R^{35b}$ represents a substituted or unsubstituted lower alkyl group, $R^{32b}$ represents a hydrogen atom, a formyl group, or a group represented by —CH$_2$R$^{32c}$, and $R^{33b}$, $R^{34b}$, and $R^{32c}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20a1}$)(R$^{21a1}$)(R$^{22a1}$) (in the formula, $R^{20a1}$, $R^{21a1}$, and $R^{22a1}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group or a substituted or unsubstituted aralkylamino group);

(in the formula, ---- represents a single bond or a double bond, $R^{43}$ represents a hydrogen atom, a formyl group or a group represented by —CH$_2$R$^{43a}$, $R^{44}$ represents a hydrogen atom or a group represented by —CH$_2$R$^{44a}$, and $R^{44a}$, $R^{45}$, $R^{46}$, $R^{47}$, $R^{48}$, $R^{49}$, and $R^{43a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20c}$)(R$^{21c}$)(R$^{22c}$) (in the formula, $R^{20c}$, $R^{21c}$, and $R^{22c}$ have the same meanings as the above defined $R^{20}$, $R^{21}$, and $R^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, or a substituted or unsubstituted aralkylamino group);

(D)

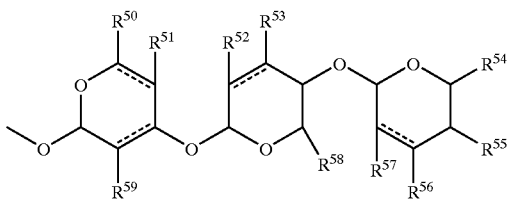

(in the formula, ---- represents a single bond or a double bond, $R^{50}$ represents a hydrogen atom, a formyl group or a group represented by —CH$_2$R$^{50a}$, $R^{58}$ represents a hydrogen atom or a group represented by —CH$_2$R$^{58a}$, $R^{54}$ represents a hydrogen atom or a group represented by —CH$_2$R$^{54a}$, and $R^{51}$, $R^{52}$, $R^{53}$, $R^{54a}$, $R^{55}$, $R^{56}$, $R^{57}$, $R^{58a}$, $R^{59}$, and $R^{50a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20d}$)(R$^{21d}$)(R$^{22d}$) (in the formula, R$^{20d}$, R$^{21d}$, and R$^{22d}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)); and (E)

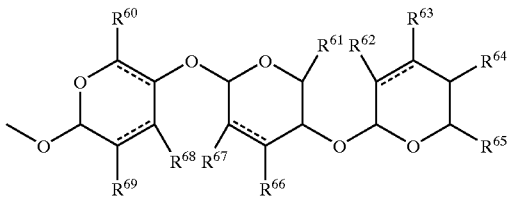

(in the formula, ---- represents a single bond or a double bond, $R^{60}$ represents a hydrogen atom, a formyl group or a group represented by —CH$_2$R$^{60a}$, $R^{61}$ represents a hydrogen atom or a group represented by —CH$_2$R$^{61a}$, $R^{65}$ represents a hydrogen atom or a group represented by —CH$_2$R$^{65a}$, and $R^{61a}$, $R^{62}$, $R^{63}$, $R^{64}$, $R^{65a}$, $R^{66}$, $R^{67}$, $R^{68}$, $R^{69}$, and $R^{60a}$ independently represent a hydrogen atom, a hydroxyl group, a substituted or unsubstituted lower alkyl group, a substituted or unsubstituted lower alkoxyl group, a substituted or unsubstituted aralkyloxy group, a substituted or unsubstituted aroyloxy group, a substituted or unsubstituted lower alkenoyloxy group, a substituted or unsubstituted lower alkanoyloxy group, a substituted or unsubstituted aryloxy group, —OSi(R$^{20e}$)(R$^{21e}$)(R$^{22e}$) (in the formula, R$^{20e}$, R$^{21e}$, and R$^{22e}$ have the same meanings as the above defined R$^{20}$, R$^{21}$, and R$^{22}$, respectively), a substituted or unsubstituted heteroaroylamino group, a substituted or unsubstituted lower alkylamino group, a substituted or unsubstituted lower alkanoylamino group, a substituted or unsubstituted arylamino group, a substituted or unsubstituted aroylamino group, a substituted or unsubstituted aralkylamino group, or a group represented by the aforementioned formula (B)).

3. The method for preventive and/or therapeutic treatment according to claim 2, wherein the disease is selected from the group consisting of AIDS, ARC (AIDS related condition), osteoarthritis, an autoimmune disease, collagenosis, and arteriosclerosis.

4. The method for preventive and/or therapeutic treatment according to claim 2, wherein the treatment comprises therapeutic treatment.

5. The method for preventive and/or therapeutic treatment according to claim 2, wherein the treatment comprises preventive treatment.

6. The method for preventive and/or therapeutic treatment according to claim 3, wherein the treatment comprises therapeutic treatment.

7. The method for preventive and/or therapeutic treatment according to claim 3, wherein the treatment comprises preventive treatment.

8. A tetrocarcin derivative represented by the following formula (Ia) or a salt thereof:

(Ia)

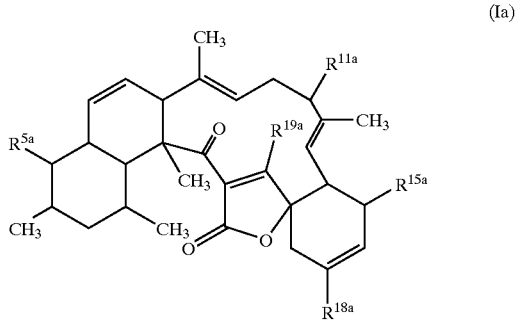

wherein $R^{15a}$ represents a hydroxyl group, —OSi(R$^{70}$)(R$^{71}$)(R$^{72}$) (in the formula, R$^{70}$, R$^{71}$, and R$^{72}$ independently represent a lower alkyl group or a substituted or unsubstituted aryl group), a substituted or unsubstituted lower alkoxyl group, a substituted or unsubstituted aralkyloxy group, a substituted or unsubstituted aryloxy group, a substituted or unsubstituted lower alkanoyloxy group, a substituted or unsubstituted lower alkenoyloxy group or a substituted or unsubstituted aroyloxy group;

$R^{11a}$ represents any one of the substituents defined for the aforementioned $R^{15a}$, or a group represented by the following formula (F):

(F)

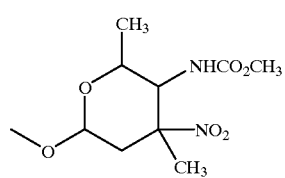

$R^{5a}$ represents any one of the substituents defined for the aforementioned $R^{15a}$, or a group selected from the group consisting of a group represented by the following formula (G):

(G)

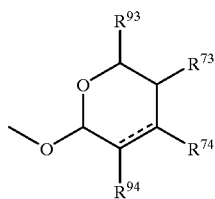

(in the formula, ---- represents a single bond or a double bond, $R^{93}$ represents a hydrogen atom or a group represented by $-CH_2R^{93a}$, and $R^{73}$, $R^{74}$, $R^{94}$, and $R^{93a}$ independently represent a hydrogen atom or any one of the substituents defined for the aforementioned $R^{15a}$), a group represented by the following formula (G-2):

(G-2)

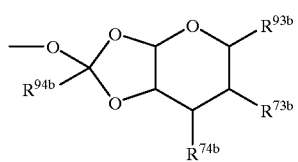

(in the formula, $R^{94b}$ represents a substituted or unsubstituted lower alkyl group, $R^{93b}$ represents a hydrogen atom or a group represented by $-CH_2R^{93c}$, and $R^{73b}$, $R^{74b}$ and $R^{93c}$ independently represent a hydrogen atom or any one of the substituents defined for the aforementioned $R^{15a}$), a group represented by the following formula (H):

(H)

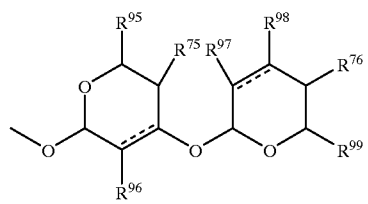

(in the formula, ---- represents a single bond or a double bond, $R^{95}$ represents a hydrogen atom or a group represented by $-CH_2R^{95a}$, $R^{99}$ represents a hydrogen atom or a group represented by $-CH_2R^{99a}$, and $R^{95a}$, $R^{75}$, $R^{96}$, $R^{97}$, $R^{98}$, $R^{76}$ and $R^{99a}$ independently represent a hydrogen atom or any one of the substituents defined for the aforementioned $R^{15a}$), a group represented by the following formula (J):

(J)

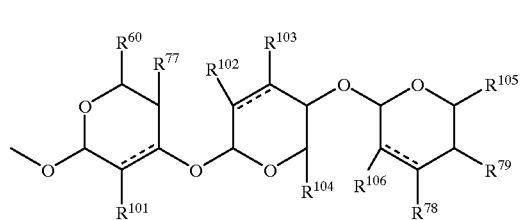

(in the formula, ---- represents a single bond or a double bond, $R^{100}$ represents a hydrogen atom or a group represented by $-CH_2R^{100a}$, $R^{104}$ represents a hydrogen atom or a group represented by $-CH_2R^{104a}$, $R^{105}$ represents a hydrogen atom or a group represented by $-CH_2R^{105a}$, and $R^{100a}$, $R^{77}$, $R^{101}$, $R^{102}$, $R^{103}$, $R^{104a}$, $R^{105a}$, $R^{78}$, $R^{79}$, and $R^{106}$ independently represent a hydrogen atom or any one of the substituents defined for the aforementioned $R^{15a}$), and a group represented by the following formula (K):

(K)

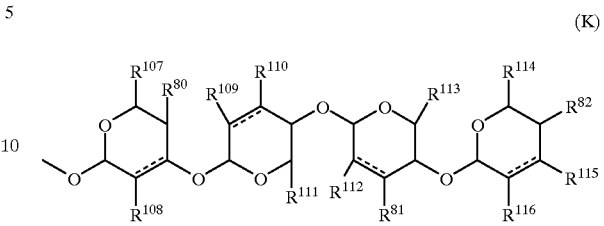

(in the formula, ---- represents a single bond or a double bond, $R^{107}$ represents a hydrogen atom or a group represented by $-CH_2R^{107a}$, $R^{111}$ represents a hydrogen atom or a group represented by $-CH_2R^{111a}$, $R^{113}$ represents a hydrogen atom or a group represented by $-CH_2R^{113a}$, $R^{114}$ represents a hydrogen atom or a group represented by $-CH_2R^{114a}$, and $R^{107a}$, $R^{80}$, $R^{108}$, $R^{109}$, $R^{110}$, $R^{111a}$, $R^{113a}$, $R^{81}$, $R^{112}$, $R^{114a}$, $R^{82}$, $R^{115}$, and $R^{116}$ independently represent a hydrogen atom or any one of the substituents defined for the aforementioned $R^{15a}$);

$R^{18a}$ represents a formyl group, a group represented by $-CH=CHR^{83}$ (in the formula, $R^{83}$ represents any one of the substituents defined for the above $R^{26}$), a group represented by $-CH=NOR^{84}$ (in the formula, $R^{84}$ represents any one of the substituents defined for the above $R^{27}$), or a group represented by $-CH(X^2R^{85})_2$ (in the formula, $X^2$ represents any one of the substituents defined for the above $X^1$, and $R^{85}$ represents any one of the substituents defined for the above $R^{28}$); and $R^{19a}$ represents a hydroxyl group or a substituted or unsubstituted lower alkoxyl group: provided that:

the aforementioned derivative wherein $R^{15a}$, $R^{11a}$, and $R^{5a}$ represent a hydroxyl group, $R^{18a}$ represents a formyl group, and $R^{19a}$ represents a methoxy group is excluded;

the aforementioned derivative wherein $R^{15a}$ and $R^{5a}$ independently represent a hydroxyl group or a lower alkanoyloxy group, $R^{11a}$ represents a hydroxyl group, a lower alkanoyloxy group, or a group represented by formula (F), $R^{18a}$ represents a formyl group, and $R^{19a}$ represents a hydroxyl group is excluded;

a compound represented by the following formula (Ib):

(Ib)

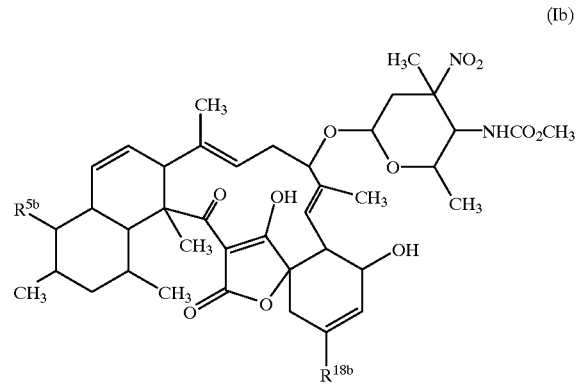

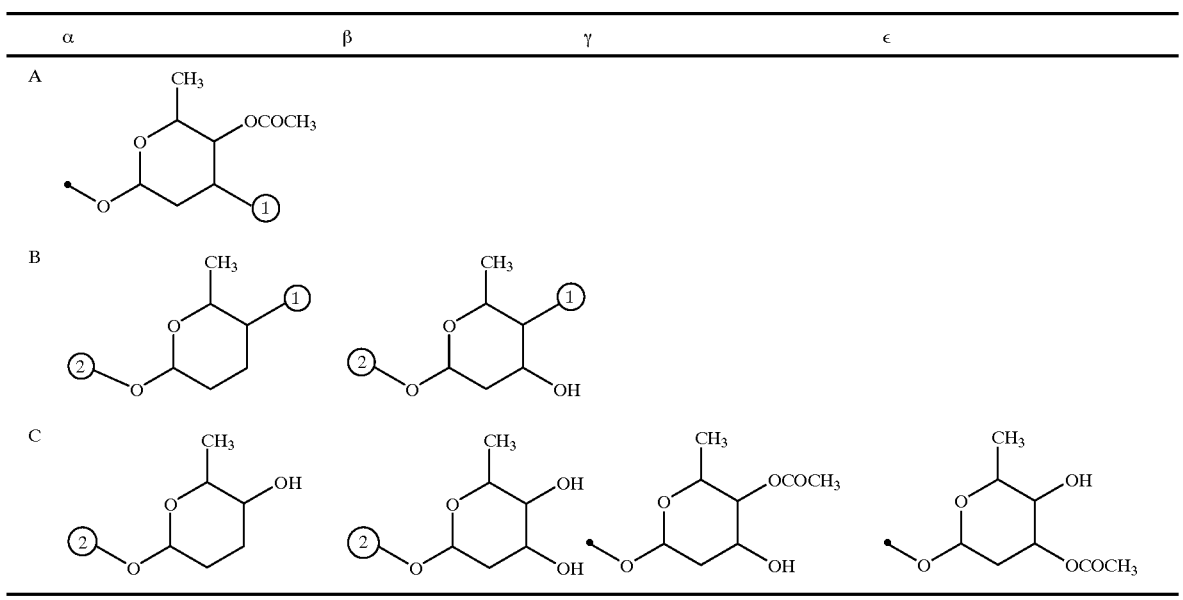

(in the formula,

R⁵b represents a group represented by Aα-Bα-Bβ-Cα (Aα substitutes for $R^{5b}$ at •, Aα-Bα means that ① of Aα and ② of Bα are bound to each other, and in the other definitions, ① and ② are bound to each other in the same manner) and $R^{18b}$ represents a formyl group;

$R^{5b}$ represents a group represented by Aα-Bα-Cβ and $R^{18b}$ represents a formyl group;

$R^{5b}$ represents a group represented by Cγ (Cγ substitutes for $R^{5b}$ at •) and $R^{18b}$ represents a formyl group;

$R^{5b}$ represents a group represented by Cε (Cε substitutes for $R^{5b}$ at •) and $R^{18b}$ represents a formyl group;

$R^{5b}$ represents a group represented by Aα-Cα and $R^{18b}$ represents a formyl group;

$R^{5b}$ represents a group represented by Aα-Bβ-Cβ and $R^{18b}$ represents a formyl group; or $R^{5b}$ represents a group represented by Aα-Bβ-Bβ-Cα and $R^{18b}$ represents a formyl group) is excluded; and a compound represented by the following formula (Ic):

(in the formula, $R^{15c}$, $R^{81c}$, and $R^{82c}$ represents an acetoxy group and $R^{19c}$ represents a hydroxyl group, or $R^{15c}$, $R^{19c}$, $R^{81c}$, and $R^{82c}$ represent a methoxy group) is excluded.

9. A medicament composition comprising the tetrocarcin derivative according to claim 8 or a physiologically acceptable salt thereof as an active ingredient.

10. A method for inducing apoptosis which comprises administering to a subject in need thereof an effective amount to induce apoptosis of the tetrocarcin derivative according to claim 8 or a physiologically acceptable salt thereof as an active ingredient.

11. A method for preventive and/or therapeutic treatment of a disease resulting from increased expression of a Bcl-2 family protein, comprising administering a preventively and/or therapeutically effective amount of the tetrocarcin derivative according to claim 8 or a physiologically acceptable salt thereof to a mammal.

12. The method for preventive and/or therapeutic treatment according to claim 11, wherein the disease resulting from increased expression of a Bcl-2 family protein is selected from the group consisting of a cancer, AIDS, ARC (AIDS related condition), osteoarthritis, an autoimmune disease, collagenosis, and arteriosclerosis.

13. The method for preventive and/or therapeutic treatment according to claim 11, wherein the treatment comprises therapeutic treatment.

14. The method for preventive and/or therapeutic treatment according to claim 11, wherein the treatment comprises preventive treatment.

15. The method for preventive and/or therapeutic treatment according to claim 12, wherein the treatment comprises therapeutic treatment.

16. The method for preventive and/or therapeutic treatment according to claim 12, wherein the treatment comprises preventive treatment.

* * * * *

UNITED STATES PATENT AND TRADEMARK OFFICE
CERTIFICATE OF CORRECTION

PATENT NO.    : 6,548,536 B2
DATED         : April 15, 2003
INVENTOR(S)   : M. Hara et al.

Page 1 of 1

It is certified that error appears in the above-identified patent and that said Letters Patent is hereby corrected as shown below:

<u>Column 68,</u>
Line 34, after "$R^8$" should read -- $R^9$ --.

<u>Column 79,</u>
Line 51, the formula:

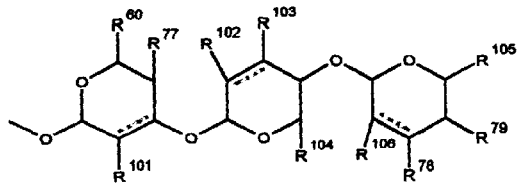

should be:

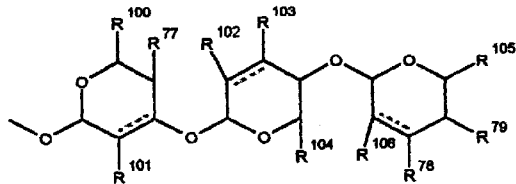

<u>Column 81,</u>
Line 28, "$R^5b$" should be -- $R^{5b}$ --.

Signed and Sealed this

Third Day of February, 2004

JON W. DUDAS
*Acting Director of the United States Patent and Trademark Office*